United States Patent
Refaeli et al.

(10) Patent No.: US 12,370,217 B2
(45) Date of Patent: Jul. 29, 2025

(54) COMPOSITIONS AND METHODS FOR TREATING T CELL EXHAUSTION

(71) Applicant: HTYR Acquistion LLC, Philadelphia, PA (US)

(72) Inventors: Yosef Refaeli, Denver, CO (US); Brian C. Turner, Denver, CO (US); Thomas R. Payne, Aurora, CO (US)

(73) Assignee: HTYR Acquisition LLC, Philadelphia, PA (US)

(*) Notice: Subject to any disclaimer, the term of this patent is extended or adjusted under 35 U.S.C. 154(b) by 777 days.

(21) Appl. No.: 17/610,592

(22) PCT Filed: May 13, 2020

(86) PCT No.: PCT/US2020/032702
§ 371 (c)(1),
(2) Date: Nov. 11, 2021

(87) PCT Pub. No.: WO2020/232141
PCT Pub. Date: Nov. 19, 2020

(65) Prior Publication Data
US 2022/0233595 A1  Jul. 28, 2022

Related U.S. Application Data

(60) Provisional application No. 62/847,701, filed on May 14, 2019.

(51) Int. Cl.
| | | |
|---|---|---|
| *A61K 35/17* | (2025.01) | |
| *A61K 35/15* | (2025.01) | |
| *A61K 35/18* | (2015.01) | |
| *A61K 39/00* | (2006.01) | |
| *A61K 39/04* | (2006.01) | |
| *A61K 39/12* | (2006.01) | |
| *A61K 39/39* | (2006.01) | |
| *A61K 40/10* | (2025.01) | |
| *A61K 40/42* | (2025.01) | |
| *A61P 35/00* | (2006.01) | |

(52) U.S. Cl.
CPC .............. *A61K 35/18* (2013.01); *A61K 35/17* (2013.01); *A61K 39/00* (2013.01); *A61K 39/001152* (2018.08); *A61K 39/04* (2013.01); *A61K 39/12* (2013.01); *A61K 39/39* (2013.01); *A61K 40/10* (2025.01); *A61K 40/4242* (2025.01); *A61P 35/00* (2018.01); *A61K 2239/31* (2023.05); *C12N 2740/16334* (2013.01)

(58) Field of Classification Search
None
See application file for complete search history.

(56) References Cited

U.S. PATENT DOCUMENTS

| | | |
|---|---|---|
| 4,900,322 A | 2/1990 | Adams |
| 4,963,489 A | 10/1990 | Naughton et al. |
| 5,289,858 A | 3/1994 | Grabenkort |
| 5,476,996 A | 12/1995 | Wilson et al. |
| 5,652,122 A | 7/1997 | Frankel et al. |
| 5,670,617 A | 9/1997 | Frankel et al. |
| 5,674,980 A | 10/1997 | Frankel et al. |
| 5,698,767 A | 12/1997 | Wilson et al. |
| 5,747,641 A | 5/1998 | Frankel et al. |
| 5,804,604 A | 9/1998 | Frankel et al. |
| 5,811,301 A | 9/1998 | Cameron |
| 5,824,837 A | 10/1998 | Chen et al. |
| 5,843,728 A | 12/1998 | Seed et al. |
| 5,847,082 A | 12/1998 | Rother et al. |
| 5,849,288 A | 12/1998 | Reisner |
| 5,851,828 A | 12/1998 | Seed et al. |
| 5,912,170 A | 6/1999 | Seed et al. |
| 6,004,811 A | 12/1999 | Seed et al. |
| 6,040,177 A | 3/2000 | Riddell et al. |
| 6,284,240 B1 | 9/2001 | Seed et al. |
| 6,358,739 B1 | 3/2002 | Baetge et al. |
| 6,392,013 B1 | 5/2002 | Seed et al. |
| 6,410,014 B1 | 6/2002 | Seed et al. |
| 6,451,558 B1 | 9/2002 | Cooke et al. |
| 6,451,601 B1 | 9/2002 | Baetge et al. |
| 6,645,501 B2 | 11/2003 | Dowdy |
| 6,753,162 B1 | 6/2004 | Seed et al. |
| 7,135,287 B1 | 11/2006 | Lonberg et al. |
| 7,311,920 B1 | 12/2007 | Devico et al. |
| 7,582,745 B2 | 9/2009 | Sah et al. |
| 7,767,453 B2 | 8/2010 | Zhang |
| 8,034,334 B2 | 10/2011 | Dudley et al. |

(Continued)

FOREIGN PATENT DOCUMENTS

| | | |
|---|---|---|
| AU | 2762802 A1 | 5/2002 |
| AU | 2006304392 A1 | 4/2007 |

(Continued)

OTHER PUBLICATIONS

Green et al. Autonomous Functional Domains of Chemically Synthesized Human Immunodeficiency Virus Tat Trans-Activator Protein. Cell, vol. 55, 1179-1188, Dec. 23, 1988.*

Dreau et al. Human Papilloma Virus in Melanoma Biopsy Specimens and Its Relation to Melanoma Progression. Annals of Surgery. vol. 231, No. 5, 664-671. (Year: 2000).*

Liermann et al. Evaluation of commercial herpes simplex virus IgG and IgM enzyme immunoassays. Journal of Virological Methods 199 (2014) 29-34.*

(Continued)

*Primary Examiner* — Nianxiang Zou
(74) *Attorney, Agent, or Firm* — Fox Rothschild LLP

(57) ABSTRACT

Provided herein are compositions and methods for treating T cell exhaustion in a subject, by administering a PTD-MYC fusion protein (e.g., an HIV TAT-MYC fusion protein) or immune cells treated with a PTD-MYC fusion protein. Kits for use in practicing the methods are also provided herein.

9 Claims, 14 Drawing Sheets
Specification includes a Sequence Listing.

(56) References Cited

U.S. PATENT DOCUMENTS

| | | | |
|---|---|---|---|
| 8,211,422 B2 | 7/2012 | Eshhar et al. | |
| 8,481,492 B2 | 7/2013 | Edenhofer et al. | |
| 8,637,307 B2 | 1/2014 | June et al. | |
| 8,697,854 B2 | 4/2014 | Schendel et al. | |
| 8,784,825 B2 | 7/2014 | Refaeli et al. | |
| 8,828,723 B2 | 9/2014 | Refaeli et al. | |
| 8,986,702 B2 | 3/2015 | Refaeli et al. | |
| 9,150,831 B2 | 10/2015 | Cambier et al. | |
| 9,169,462 B2 | 10/2015 | Refaeli et al. | |
| 9,365,825 B2 | 6/2016 | Turner et al. | |
| 9,775,897 B2 | 10/2017 | Refaeli et al. | |
| 9,789,135 B2 * | 10/2017 | Turner | A61P 35/02 |
| 10,087,420 B2 | 10/2018 | Turner et al. | |
| 10,149,898 B2 | 12/2018 | Refaeli et al. | |
| 10,442,853 B2 | 10/2019 | Refaeli et al. | |
| 10,760,055 B2 | 9/2020 | Cambier et al. | |
| 10,864,259 B2 | 12/2020 | Refaeli et al. | |
| 11,116,796 B2 | 9/2021 | Turner et al. | |
| 11,369,678 B2 | 6/2022 | Refaeli et al. | |
| 2001/0049393 A1 | 12/2001 | Coller et al. | |
| 2002/0055478 A1 | 5/2002 | Faris et al. | |
| 2002/0076787 A1 | 6/2002 | Baetge et al. | |
| 2002/0098166 A1 | 7/2002 | Havemann et al. | |
| 2002/0155502 A1 | 10/2002 | Balint et al. | |
| 2003/0072794 A1 | 4/2003 | Boulikas | |
| 2003/0138859 A1 | 7/2003 | Barbera-Guillem et al. | |
| 2003/0220286 A1 | 11/2003 | Abruzzese et al. | |
| 2004/0224402 A1 | 11/2004 | Bonyhadi et al. | |
| 2005/0220705 A1 | 10/2005 | Brooks et al. | |
| 2005/0281816 A1 | 12/2005 | Lamping et al. | |
| 2006/0068369 A1 | 3/2006 | Coelho et al. | |
| 2006/0068469 A1 | 3/2006 | Payne et al. | |
| 2006/0115898 A1 | 6/2006 | Zhang et al. | |
| 2006/0154331 A1 | 7/2006 | Avidan et al. | |
| 2006/0156422 A1 | 7/2006 | Dalrymple et al. | |
| 2006/0222657 A1 | 10/2006 | Dowdy et al. | |
| 2007/0011753 A1 | 1/2007 | Ito et al. | |
| 2007/0047583 A1 | 3/2007 | Assa et al. | |
| 2007/0067854 A1 | 3/2007 | Habu et al. | |
| 2007/0082397 A1 | 4/2007 | Hasson et al. | |
| 2007/0093420 A1 | 4/2007 | Yeomans et al. | |
| 2007/0098715 A1 | 5/2007 | Ettenberg et al. | |
| 2007/0116691 A1 | 5/2007 | Cambier et al. | |
| 2007/0130628 A1 | 6/2007 | Brown | |
| 2007/0248618 A1 | 10/2007 | Cohen | |
| 2008/0050396 A1 | 2/2008 | Andersen et al. | |
| 2009/0291094 A1 | 11/2009 | Refaeli et al. | |
| 2010/0047217 A1 | 2/2010 | Refaeli et al. | |
| 2010/0055129 A1 | 3/2010 | Refaeli et al. | |
| 2010/0233804 A1 | 9/2010 | Zhou et al. | |
| 2010/0279351 A1 | 11/2010 | Refaeli | |
| 2010/0297763 A1 | 11/2010 | Cambier et al. | |
| 2011/0218210 A1 | 9/2011 | Refaeli et al. | |
| 2012/0003189 A1 | 1/2012 | Pelus et al. | |
| 2012/0027792 A1 | 2/2012 | Pavlakis et al. | |
| 2012/0244133 A1 | 9/2012 | Rosenberg et al. | |
| 2012/0251563 A1 | 10/2012 | Nicchitta et al. | |
| 2013/0177586 A1 | 7/2013 | Refaeli et al. | |
| 2014/0109246 A1 | 4/2014 | Jimeno et al. | |
| 2014/0255369 A1 | 9/2014 | Turner et al. | |
| 2014/0273212 A1 * | 9/2014 | Turner | C07K 14/4747 435/405 |
| 2014/0356392 A1 | 12/2014 | Refaeli et al. | |
| 2015/0164950 A1 | 6/2015 | Turner et al. | |
| 2015/0218515 A1 | 8/2015 | Altrichter et al. | |
| 2017/0044500 A1 | 2/2017 | Cooper et al. | |
| 2018/0036396 A1 | 2/2018 | Refaeli et al. | |
| 2019/0060434 A1 | 2/2019 | Refaeli et al. | |
| 2020/0215188 A1 | 7/2020 | Refaeli et al. | |
| 2021/0121550 A1 | 4/2021 | Refaeli et al. | |

FOREIGN PATENT DOCUMENTS

| | | |
|---|---|---|
| CA | 2584738 A1 | 4/2006 |
| CA | 2626525 A1 | 4/2007 |
| CN | 1206044 | 1/1999 |
| CN | 1357620 A | 7/2002 |
| CN | 1659187 | 8/2005 |
| CN | 101045914 A | 10/2007 |
| CN | 101330830 A | 12/2008 |
| CN | 102027105 A | 4/2011 |
| CN | 102083960 A | 6/2011 |
| CN | 102083970 | 6/2011 |
| CN | 103998604 | 8/2014 |
| CN | 104353066 A | 2/2015 |
| CN | 104640551 | 5/2015 |
| EP | 0 367 76 A2 | 9/1981 |
| EP | 0 213 469 A2 | 3/1987 |
| EP | 1 103 615 A1 | 5/2001 |
| EP | 1 357 184 | 10/2003 |
| EP | 1 792 627 | 6/2007 |
| GB | 2 387 599 | 10/2003 |
| JP | 2000-175692 | 6/2000 |
| JP | 2000-189157 | 7/2000 |
| JP | 2001-501909 | 2/2001 |
| JP | 2001-518300 | 10/2001 |
| JP | 2002-541786 A | 12/2002 |
| JP | 2003-513672 A | 4/2003 |
| JP | 2003-514565 | 4/2003 |
| JP | 2003-265189 | 9/2003 |
| JP | 2004-519245 A | 7/2004 |
| JP | 2005-523012 | 8/2005 |
| JP | 2005-525085 | 8/2005 |
| JP | 2005-232148 | 9/2005 |
| JP | 2005-527211 | 9/2005 |
| JP | 2006-519781 A | 8/2006 |
| JP | 2009-511081 A | 3/2009 |
| JP | 2011-528567 A | 11/2011 |
| JP | 2012-501347 A | 1/2012 |
| JP | 2014-527980 A | 10/2014 |
| JP | 2015-524415 A | 8/2015 |
| JP | 6167130 B2 | 8/2015 |
| JP | 2015-525209 A | 9/2015 |
| JP | 2016-510996 A | 4/2016 |
| JP | 2017-513498 | 6/2017 |
| JP | 6484293 B2 | 3/2019 |
| JP | 6655050 B2 | 2/2020 |
| WO | WO-86/03780 A1 | 7/1986 |
| WO | WO-92/15322 | 9/1992 |
| WO | WO-94/04686 | 3/1994 |
| WO | WO-94/19465 | 9/1994 |
| WO | WO-95/14078 | 5/1995 |
| WO | WO-98/10058 | 3/1998 |
| WO | WO-98/52614 | 11/1998 |
| WO | WO-99/16884 | 4/1999 |
| WO | WO-99/45962 | 9/1999 |
| WO | WO-99/53023 | 10/1999 |
| WO | WO-99/53028 | 10/1999 |
| WO | WO-00/09669 | 2/2000 |
| WO | WO-00/61617 A2 | 10/2000 |
| WO | WO-00/62067 | 10/2000 |
| WO | WO-01/34824 A2 | 5/2001 |
| WO | WO-01/38548 | 5/2001 |
| WO | WO-02/057436 | 7/2002 |
| WO | WO-02/074968 A1 | 9/2002 |
| WO | WO-03/008630 | 1/2003 |
| WO | WO-03/020763 | 3/2003 |
| WO | WO-03/033701 | 4/2003 |
| WO | WO-03/038057 | 5/2003 |
| WO | WO-03/039462 | 5/2003 |
| WO | WO-03/057171 A2 | 7/2003 |
| WO | WO-03/089580 | 10/2003 |
| WO | WO-03/089630 | 10/2003 |
| WO | WO-03/094849 | 11/2003 |
| WO | WO-03/097675 | 11/2003 |
| WO | WO-2004/033685 A1 | 4/2004 |
| WO | WO-2004/035535 | 4/2004 |
| WO | WO-2004/044004 A2 | 5/2004 |
| WO | WO-2004/050885 | 6/2004 |
| WO | WO-2004/050895 A2 | 6/2004 |

(56) References Cited

FOREIGN PATENT DOCUMENTS

| | | |
|---|---|---|
| WO | WO-2004/074322 A1 | 9/2004 |
| WO | WO-2004/084805 | 10/2004 |
| WO | WO-2005/014785 | 2/2005 |
| WO | WO-2005/049073 A2 | 6/2005 |
| WO | WO-2005/084158 | 9/2005 |
| WO | WO-2005/113595 A2 | 12/2005 |
| WO | WO-2005/114215 A2 | 12/2005 |
| WO | WO-2006/000830 A2 | 1/2006 |
| WO | WO-2006/032876 | 3/2006 |
| WO | WO-2006/116512 | 11/2006 |
| WO | WO-2006/125962 A2 | 11/2006 |
| WO | WO-2007/047583 A2 | 4/2007 |
| WO | WO-2007/067183 | 6/2007 |
| WO | WO-2008/038002 A2 | 4/2008 |
| WO | WO-2008/039818 A2 | 4/2008 |
| WO | WO-2008/112922 | 9/2008 |
| WO | WO-2009/059304 | 5/2009 |
| WO | WO-2009/139930 A2 | 11/2009 |
| WO | WO-2010/011644 | 1/2010 |
| WO | WO-2010/025421 A2 | 3/2010 |
| WO | WO-2011/100477 A2 | 8/2011 |
| WO | WO-2012/055170 | 5/2012 |
| WO | WO-2013/039889 A1 | 3/2013 |
| WO | WO-2013/166321 A1 | 11/2013 |
| WO | WO-2014/018863 A1 | 1/2014 |
| WO | WO-2014/039908 A1 | 3/2014 |
| WO | WO-2014/083173 A1 | 6/2014 |
| WO | WO-2014/133567 A1 | 9/2014 |
| WO | WO-2014/133568 A1 | 9/2014 |
| WO | WO-2014/164606 A1 | 10/2014 |
| WO | WO-2016/105542 A2 | 6/2016 |
| WO | WO-2017/059319 A2 | 4/2017 |
| WO | WO-2017/123978 A1 | 7/2017 |
| WO | WO-2018/104909 A2 | 6/2018 |
| WO | 2019028098 A1 | 2/2019 |

OTHER PUBLICATIONS

Velu et al. Role of PD-1 co-inhibitory pathway in HIV infection and potential therapeutic options. Velu et al. Retrovirology (2015) 12:14.*
Caron, et al., "Intracellular Delivery of a Tat-eGFP Fusion Protein into Muscle Cells." Molecular Therapy, Mar. 2001, vol. 3, No. 3, pp. 310-318.
Chandran, et al., "Tumor-Specific Effector CD8 T Cells That Can Establish Immunological Memory in Humans after Adoptive Transfer Are Marked by Expression of IL7 Receptor and c-myc." Cancer Res. Aug. 15, 2015, vol. 75, No. 16, pp. 3216-3226.
Deleeuw, et al., "CD25 Identifies a Subset of CD4 FoxP3-TIL That Are Exhausted Yet Prognostically Favorable in Human Ovarian Cancer." Cancer Immunol. Res. Mar. 1, 2015, vol. 3, No. 3, pp. 245-253.
Non-Final Office Action on U.S. Appl. No. 16/598,690 dtd Mar. 1, 2022.
Non-Final Office Action on U.S. Appl. No. 16/635,383 dtd Feb. 18, 2022.
Vives, et al., "A Truncated HIV-1 Tat Protein Basic Domain Rapidly Translocates through the Plasma Membrane and Accumulates in the Cell Nucleus." Journal of Biol. Chemistry. Jun. 20, 1997, vol. 272, No. 25, pp. 16010-16017.
Wold et al., "Antibody Therapeutics in Oncology", Immunotherapy, Mar. 2016, pp. 1-18, vol. 2, No. 1.
"Myc proto-oncogene protein [*Homo sapiens*]", NCBI Protein Database, NCBI, retrieved Jul. 24, 2017 from URL: https://www.ncbi.nih.gov/protein/71774083?report=genbank&log$=protalign&blast_rank=1&RID=RC7XFBOS014 (4 pages).
"Stem Cell", Wikipedia, 2008, retrieved Nov. 13 from URL: http// en.wikipedia.org/wiki/Stem_cell (11 pages).
Altman et al., "Phenotypic Analysis of Antigen-Specific T Lymphocytes", Science, vol. 274, 1996, pp. 94-96 (4 pages).
Amino Acid, NCBI, 2018 (8 pages).
Andersen et al., "Parallel detection of antigen-specific T cell responses by combinatiorial encoding of MHC multimers", Nature Protocols, vol. 7, No. 5, 2012, pp. 891-902, DOI: 10.1038/nprot.2012.037 (12 pages).
U.S. Appl. No. 12/048,148, filed Mar. 13, 2008 (50 pages).
U.S. Appl. No. 12/506,894, filed Jul. 21, 2009 (59 pages).
Aubry et al., "N-Myc Shares Cellular Functions with c-Myc", DNA and Cell Biology, vol. 19, No. 6, Jun. 2000, pp. 353-364 (12 pages).
Austrian Search Report and Written Opinion SG 201101367-9 dated Mar. 23, 2012 (17 pages).
Baum, Christopher, "Insertional Mutagenesis in Gene Therapy and Stem Cell Biology", Current Opinion in Hematology, vol. 14, Jul. 2007, pp. 337-342 (6 pages).
Beerens et al., "Protein Transduction Domains and their Utility in Gene Therapy", Current Gene Therapy, vol. 3, No. 5, 2003, pp. 486-494 (9 pages).
Benassayag et al., "Human c-Myc Isoforms Differentially Regulate Cell Growth and Apoptosis in *Drosophila melanogaster*," Molecular and Cellular Biology, vol. 25, No. 22, 2005, pp. 9897-9909 (14 pages).
Berkson et al., "Pilot Screening Programme for Small Molecule Activators of p53", International Journal of Cancer, vol. 115, 2005, pp. 701-710, DOI: 10.1002/ijc.20968 (10 pages).
Bird et al., "Expansion of Human and Murine Hematopoietic Stem and Progenitor Cells Ex Vivo without Genetic Modification Using MYC and Bcl-2 Fusion Proteins", PLoS One, vol. 9, No. 8, e105525, 2014, pp. 1-20, DOI: 10.1371/journal.pone.0105525 (20 pages).
Bissonnette et al., "Apoptotic cell death induced by c-myc is inhibited by bcl-2", Nature, vol. 359, Oct. 8, 1992, pp. 552-554 (3 pages).
Bouchard et al., "Control of cell proliferation by Myc", Trends in Cell Biology, vol. 8, 1998, pp. 202-206 (5 pages).
Bunting et al., "Restoration of lymphocyte function in Janus kinase 3-deficient mice by retroviral-mediated gene transfer," Nature Medicine, vol. 4, No. 1, 1998, pp. 58-64 (7 pages).
Buske et al., "Deregulated expression of HOXB4 enhances the primitive growth activity of human hematopoietic cells", Blood, vol. 100, No. 3, Aug. 1, 2002, pp. 862-868 (7 pages).
Capecchi, Mario R., "Altering the Genome by Homologous Recombination", Science, vol. 244, No. 4910, Jun. 16, 1989, pp. 1288-1292 (5 pages).
Caron et al., "Endosome disruption enhances the functional nuclear delivery of Tat-fusion proteins", Biochemical and Biophysical Research Communications, vol. 319, No. 1, Jun. 18, 2004, pp. 12-20 (9 pages).
Carotta et al., "Directed differentiation and mass cultivation of pure erythroid progenitors from mouse embryonic stem cells", Blood, vol. 104, No. 6, Sep. 15, 2004, pp. 1873-1880, DOI: 10.1182/blood-2004-02-0570 (8 pages).
Chadwick et al., "Notch Signaling Induces Apoptosis in Primary Human CD34+ Hematopoietic Progenitor Cells", Stem Cells, vol. 25, 2007, pp. 203-210, DOI: 10.1634/stemcells.2005-0303 (10 pages).
Chandran et al., "Tumor-Specific Effector CD8+ T Cells That Can Establish Immunological Memory in Humans after Adoptive Transfer are Marked by Expression of IL7 Receptor and c-myc", Cancer Research, vol. 75, No. 16, 2015, pp. 3216-3226, DOI: 10.1158/0008-5472.CAN-15-0584 (12 pages).
Chang et al., "Phenotypic expression in *E. coli* of a DNA sequence coding for mouse dihydrofolate reductase", Nature, vol. 275, Oct. 19, 1978, pp. 617-624 (8 pages).
Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845 (8 pages).
Cheng et al., "BCL-2, BCL-XL, Sequester BH3 Domain-Only Molecules Preventing BAX- and BAK-Mediated Mitochondrial Apoptosis", Molecular Cell, vol. 8, Sep. 2001, pp. 705-711 (7 pages).

(56) References Cited

OTHER PUBLICATIONS

Chi et al., "Physical Stability of Proteins in Aqueous Solution: Mechanism and Driving Forces in Nonnative Protein Aggregation," Pharmaceutical Research, vol. 20, No. 9, Sep. 2003, pp. 1325-1336 (2 pages).
Chin et al., "Essential role for oncogenic Ras in tumour maintenance", Nature, vol. 400, Jul. 29, 1999, pp. 468-472 (5 pages).
Choi et al., "Myc protein is stabilized by suppression of a novel E3 ligase complex in cancer cells", Genes & Development, vol. 24, 2010, pp. 1236-1241, DOI: 10.1101/gad.1920310 (6 pages).
Choi et al., "Status Epilepticus-Induced Somatostatinergic Hilar Interneuron Degeneration Is Regulated by Striatal Enriched Protein Tyrosine Phosphatase", Journal of Neuroscience, vol. 27, No. 11, Mar. 14, 2007, pp. 2999-3009, DOI: 10.1523/JNEUROSCI.4913-06.2007 (11 pages).
Cleland et al., "The Development of Stable Protein Formulations: A Close Look at Protein Aggregation, Deamidation, and Oxidation," Critical Reviews in Therapeutic Drug Carrier Systems, vol. 10, No. 4, Jan. 1, 1993, pp. 307-377 (75 pages).
Coeytaux et al., "The Cationic Amphipathic alpha-Helix of HIV-1 Viral Protein R (Vpr) Binds to Nucleic Acids, Permeabilizes Membranes, and Efficiently Transfects Cells", The Journal of Biological Chemistry, vol. 278, No. 20, May 16, 2003, pp. 18110-18116 (8 pages).
Coller et al., "Expression analysis with oligonucleotide microarrays reveals that MYC regulates genes involved in growth, cell cycle, signaling, and adhesion", Proceedings of the National Academy of Sciences USA, vol. 97, No. 7, 2000, pp. 3260-3265 (6 pages).
Communication pursuant to Rules 161(2) and 162 EPC for EP 17876016.1 dated Jul. 9, 2019 (3 pages).
Conti, et al., "Gene Therapy Using Neural Stem Cells", Methods in Molecular Biology, vol. 198, 2002, pp. 233-244, XP009120658 (12 pages).
Coppola et al., "Constitutive c-myc oncogene expression blocks mouse erythroleukaemia cell differentiation but not commitment", Nature, vol. 320, Apr. 24, 1986, pp. 760-763 (4 pages).
Corrected Notice of Allowability for U.S. Appl. No. 15/179,735 dated Jun. 15, 2018 (2 pages).
Corrected Notice of Allowability for U.S. Appl. No. 15/179,735 dated Jun. 8, 2018 (2 pages).
Corrected Notice of Allowability for U.S. Appl. No. 16/042,904 dated Mar. 6, 2020 (4 pages).
Corrected Notice of Allowance for U.S. Appl. No. 15/643,133 dated Jun. 8, 2020 (2 pages).
Corrected Notice of Allowance for U.S. Appl. No. 15/717,675 dated Jan. 10, 2020 (2 pages).
Corrected Notice of Allowance for U.S. Appl. No. 15/717,675 dated Nov. 6, 2019 (4 pages).
Corrected Notice of Allowance for U.S. Appl. No. 16/042,904 dated Jan. 29, 2020 (2 pages).
Corrected Notice of Allowance for U.S. Appl. No. 16/042,904 dated Jun. 2, 2020 (4 pages).
Corrected Notice of Allowance for U.S. Appl. No. 16/042,904 dated Jun. 22, 2020 (4 pages).
Corrected Notice of Allowance for U.S. Appl. No. 16/261,207 dated Feb. 1, 2021 (4 pages).
D'Alessandro et al., "Red blood cell storage: the story so far", Blood transfusion = Trasfusione del sangue, vol. 8, 2010, pp. 82-88, DOI: 10.2450/2009.0122-09 (7 pages).
Dang et al., "Identification of the Human c-myc Protein Nuclear Translocation Signal", Molecular and Cellular Biology, vol. 8, No. 10, Oct. 1988, pp. 4048-4054 (7 pages).
Dang et al., "Nuclear and Nucleolar Targeting Sequences of c-erb-A, c-myb, N-myc, p53, HSP70, and HIV tat Proteins", Journal of Biological Chemistry, vol. 264, No. 30, Oct. 25, 1989, pp. 18019-18023 (5 pages).
Dang, Chi V., "c-Myc Target Genes Involved in Cell Growth, Apoptosis, and Metabolism", Molecular and Cellular Biology, vol. 19, No. 1, Jan. 1999, pp. 1-11 (11 pages).

Daugas et al., "Erythrocytes: Death of a mummy", Cell Death and Differentiation, vol. 8, No. 12, 2001, pp. 1131-1133 (3 pages).
De Boer et al., "The tac promoter: A functional hybrid derived from the trp and lac promoters", Proceedings of the National Academy of Sciences USA, Biochemistry, vol. 80, 1983, pp. 21-25 (5 pages).
De Korte, D. "New additive solutions for red cells", ISBT Science Series, vol. 11, Suppl. 1, 2016, pp. 165-170 (6 pages).
Decision of Rejection for CN 200580031545.8 dated Jul. 3, 2012, English Translation Only (11 pages).
Decision of Rejection for CN 201380048261.4 dated Apr. 16, 2019 (15 pages).
Decision of Rejection for JP 2008-536713 dated Aug. 5, 2013, English Translation Only (2 pages).
Decision of Rejection for JP 2011-520133 dated Nov. 26, 2014 (9 pages).
Decision of Rejection for JP 2011-525258 date Dec. 3, 2014 (11 pages).
Decision of Rejection for JP 2014-108137 dated Jun. 2, 2016 (25 pages).
Decision of Rejection for JP 2018-153567 dated Mar. 18, 2020 (7 pages).
Delgado et al., "Myc Roles in Hematopoiesis and Leukemia", Genes and Cancer, vol. 1, No. 6, 2010, pp. 605-616, DOI: 10.1177/1947601910377495 (12 pages).
Deocampo, et al., "Cooperation of bcl-2 and myc in the neoplastic transformation of normal rat liver epithelial cells is related to the down-regulation of gap junction-mediated intercellular communication", Carcinogenesis, vol. 21, No. 8, 2000, pp. 1501-1506 (6 pages).
Derossi et al., "Trojan peptides: the penetratin system for intracellular delivery", Cell Biology, vol. 8, Feb. 1998, pp. 84-87 (4 pages).
Dmitrovsky et al., "A Transfected c-myc Oncogene Inhibits Mouse Erytholeukemic Differentiation", Current Topics in Microbiology and Immunology, vol. 132, 1986 (4 pages).
Domashenko et al., "TAT-mediated transduction of NF-Ya peptide induces the ex vivo proliferation and egraftment potential of human hematopoietic progenitor cells," Blood, vol. 116, No. 15, Oct. 14, 2010, pp. 2676-2683 (9 pages).
Domen et al., "The Role of Apoptosis in the Regulation of Hematopoietic Stem Cells: Overexpression of BCL-2 Increase Both Their Number and Repopulation Potential", Journal of Experimental Medicine, vol. 191, No. 2, 2000, pp. 253-263 (11 pages).
Dudley et al., "Adoptive Cell Transfer Therapy Following Non-Myeloablative but Lymphodepleting Chemotherapy for the Treatment of Patients with Refractory Metastatic Melanoma", Journal of Clinical Oncology, vol. 23, No. 10, Apr. 1, 2005, pp. 2346-2357, DOI: 10.1200/JCO.2005.00.240 (12 pages).
Dvorak et al., "Cytochemical Localization of Peroxidase Activity in the Developing Erythrocyte", American Journal of Pathology, vol. 67, No. 2, 1972, pp. 303-326 (24 pages).
Eilers et al., "Chimaeras of Myc oncoprotein and steroid receptors cause hormone-dependent transformation of cells", Nature, vol. 340, No. 6228, Jul. 6, 1989, pp. 66-68 (3 pages).
Eischen et al., "Apoptosis Triggered by Myc-Induced Suppression of Bcl-XL or Bcl-2 Is Bypassed during Lymphomagenesis", Molecular and Cellular Biology, vol. 21, No. 15, Aug. 2001, pp. 5063-5070, DOI: 10.1128/MCB.21.15.5063-5070.2001 (9 pages).
Elliot et al., "Intercellular Trafficking and Protein Delivery by a Herpesvirus Structural Protein", Cell, vol. 88, Jan. 24, 1997, pp. 223-233 (11 pages).
Esdar et al., "Differentiation-associated apoptosis of neural stem cells is effected by Bcl-2 overexpression: impact on cell lineage determination" European Journal of Cell Biology, vol. 80, No. 8, Aug. 2001, pp. 539-553 (15 pages).
Examination Report for AU 2018247295 dated Dec. 6, 2019 (2 pages).
Examination Report for CA 2626525 dated Apr. 17, 2013 (4 pages).
Examination Report for CA 2626525 dated Apr. 8, 2014 (4 pages).
Examination Report for CA 2626525 dated Jul. 4, 2018 (3 pages).
Examination Report for CA 2626525 dated Jun. 13, 2017 (3 pages).
Examination Report for CA 2626525 dated Jun. 6, 2016 (3 pages).
Examination Report for CA 2626525 dated May 8, 2015 (3 pages).
Examination Report for CA 2680613 dated Nov. 21, 2013 (3 pages).

(56) References Cited

OTHER PUBLICATIONS

Examination Report for CA 2680613 dated Nov. 28, 2014 (4 pages).
Examination Report for CA 2723114 dated Apr. 21, 2015 (4 pages).
Examination Report for CA 2723114 dated Jul. 7, 2016 (3 pages).
Examination Report for CA 2731767 dated Jul. 25, 2012 (3 pages).
Examination Report for CA 2731767 dated Oct. 5, 2015 (3 pages).
Examination Report for CA 2731767 dated Sep. 5, 2014 (2 pages).
Examination Report for CA 2735522 dated Nov. 16, 2015 (4 pages).
Examination Report for CA 2735522 dated Oct. 2, 2014 (2 pages).
Examination Report for CA 2735522 dated Sep. 10, 2012 (3 pages).
Examination Report for CA 2879667 dated Jun. 18, 2019 (4 pages).
Examination Report for CA 2879667 dated May 25, 2020 (4 pages).
Examination Report for CA 2905285 dated Jan. 30, 2020 (5 pages).
Examination Report for CA 2905296 dated Feb. 11, 2021 (7 pages).
Examination Report for CA 2905296 dated Jan. 31, 2020 (4 pages).
Examination Report for CA 3035209 dated Feb. 3, 2020 (4 pages).
Examination Report for CA 3035209 dated Feb. 4, 2021 (4 pages).
Examination Report for CA 3065947 dated Nov. 4, 2020 (4 pages).
Examination Report for CA 3065947 dated Oct. 13, 2021 (4 pages).
Examination Report for EP 06826025.6 dated Sep. 22, 2009 (1 page).
Examination Report for EP 08743862.8 dated Sep. 23, 2010 (6 pages).
Examination Report for EP 08743862.8 dated on May 14, 2010 (6 pages).
Examination Report for EP 09747016.5 dated Apr. 9, 2013 (6 pages).
Examination Report for EP 09747016.5 dated Jul. 26, 2016 (5 pages).
Examination Report for EP 09747016.5 dated Jun. 12, 2017 (6 pages).
Examination Report for EP 09747016.5 dated Mar. 19, 2015 (5 pages).
Examination Report for EP 09747016.5 dated May 15, 2018 (7 pages).
Examination Report for EP 09810692.5 dated Mar. 28, 2012 (3 pages).
Examination Report for EP 09810692.5 dated Oct. 22, 2014 (3 pages).
Examination Report for EP 12187097.6 dated Jan. 22, 2015 (6 pages).
Examination Report for EP 13820331.0 dated Apr. 24, 2018 (4 pages).
Examination Report for EP 13820331.0 dated Jul. 29, 2019 (3 pages).
Examination Report for EP 14778538.0 dated Apr. 16, 2018 (4 pages).
Examination Report for EP 14779483.8 dated Apr. 28, 2021 (3 pages).
Examination Report for EP 14779483.8 dated Aug. 11, 2020 (3 pages).
Examination Report for EP 14779483.8 dated Jan. 14, 2019 (4 pages).
Examination Report for EP 14779483.8 dated Jun. 28, 2019 (4 pages).
Examination Report for EP 14779483.8 dated Jun. 29, 2018 (4 pages).
Examination Report for EP 14779483.8 dated Oct. 16, 2017 (4 pages).
Examination Report for EP 17876016.1 dated Apr. 12, 2021 (5 pages).
Examination Report for EP 17920607.3 dated Aug. 26, 2020 (5 pages).
Examination Report for EP 18154875.1 dated Sep. 6, 2019 (4 pages).
Examination Report for IN 2048/DELNP/2011 dated Sep. 15, 2016 (9 pages).
Examination Report for IN 3332/DELNP/2008 dated Aug. 23, 2013 (6 pages).
Examination Report for IN 634/DELNP/2011 dated Jun. 8, 2017 (10 pages).
Examination Report for IN 6624/DELNP/2014 dated Sep. 27, 2018 (4 pages).
Examination Report for IN 9033/DELNP/2010 dated May 19, 2017 (11 pages).
Examination Report for IN 9205/DELNP/2015 dated Nov. 28, 2019 (8 pages).
Examination Report for IN 9206/DELNP/2015 dated Dec. 26, 2019 (6 pages).
Examination Report No. 1 for AU 2009285547 dated Jul. 25, 2011 (2 pages).
Examination Report No. 1 for AU 2013292330 dated Sep. 6, 2017 (3 pages).
Examination Report No. 1 for AU 2014202016 dated May 12, 2015 (3 pages).
Examination Report No. 1 for AU 2014249200 dated Mar. 15, 2019 (4 pages).
Examination Report No. 1 for AU 2016203892 dated Apr. 12, 2017 (3 pages).
Extended European Search Report for EP 06826025.6 dated Aug. 13, 2009 (8 pages).
Extended European Search Report for EP 09747016.5 dated May 30, 2012 (8 pages).
Extended European Search Report for EP 09800871.7 dated Jun. 24, 2011 (5 pages).
Extended European Search Report for EP 09810692.5 dated Jul. 11, 2011 (5 pages).
Extended European Search Report for EP 12187077.8 dated Mar. 25, 2013 (7 pages).
Extended European Search Report for EP 12187097.6 dated Mar. 27, 2013 (8 pages).
Extended European Search Report for EP 13188850.0 dated May 27, 2014 (8 pages).
Extended European Search Report for EP 13820331.0 dated Oct. 10, 2016 (9 pages).
Extended European Search Report for EP 14778538.0 dated Sep. 29, 2016 (17 pages).
Extended European Search Report for EP 14779483.8 dated Dec. 23, 2016 (5 pages).
Extended European Search Report for EP 15175802.6 dated Dec. 14, 2015 (7 pages).
Extended European Search Report for EP 17876016.1 dated Jun. 26, 2020 (7 pages).
Extended European Search Report for EP 18154875.1 dated Apr. 24, 2018 (8 pages).
Extended European Search Report for EP 18841366.0 dated Mar. 16, 2021 (7 pages).
Extended European Search Report for EP 20212922.7 dated May 26, 2021 (7 pages).
Extended European Search Report for EP 21170329.3 dated Oct. 22, 2021 (10 pages).
Extended Search Report for EP 17920607.3 dated Dec. 11, 2019 (7 pages).
Extended Search Report for EP 19157513.3 dated Apr. 1, 2019 (13 pages).
Fanidi et al., "Cooperative interaction between c-myc and bcl-2 proto-oncogenes", Nature, vol. 359, Oct. 8, 1992, pp. 554-556 (3 pages).
Felsher et al., "Reversible Tumorigenesis by MYC in Hematopoietic Lineages", Molecular Cell, vol. 4, Aug. 1999, pp. 199-207 (9 pages).
Fifth Office Action for CN 200980126312.4 dated Jan. 22, 2014, English Translation Only (3 pages).
Final Office Action for U.S. Appl. No. 11/583,970 dated Apr. 9, 2014 (20 pages).
Final Office Action for U.S. Appl. No. 11/583,970 dated Nov. 17, 2011 (16 pages).
Final Office Action for U.S. Appl. No. 11/583,970 dated Nov. 26, 2008 (14 pages).
Final Office Action for U.S. Appl. No. 11/583,970 dated Nov. 4, 2009 (10 pages).

(56) References Cited

OTHER PUBLICATIONS

Final Office Action for U.S. Appl. No. 12/048,148 dated Feb. 15, 2013 (17 pages).
Final Office Action for U.S. Appl. No. 12/467,957 dated Feb. 28, 2011 (8 pages).
Final Office Action for U.S. Appl. No. 12/467,957 dated Sep. 17, 2014 (9 pages).
Final Office Action for U.S. Appl. No. 12/506,894 dated Oct. 9, 2014 (15 pages).
Final Office Action for U.S. Appl. No. 12/550,166 dated May 11, 2012 (12 pages).
Final Office Action for U.S. Appl. No. 12/701,383 dated Nov. 13, 2014 (18 pages).
Final Office Action for U.S. Appl. No. 12/701,383 dated Nov. 16, 2011 (14 pages).
Final Office Action for U.S. Appl. No. 13/795,659 dated Jul. 11, 2014 (16 pages).
Final Office Action for U.S. Appl. No. 13/795,659 dated Mar. 26, 2015 (18 pages).
Final Office Action for U.S. Appl. No. 13/797,648 dated Apr. 1, 2015 (12 pages).
Final Office Action for U.S. Appl. No. 13/797,648 dated Feb. 8, 2017 (18 pages).
Final Office Action for U.S. Appl. No. 14/461,105 dated Sep. 15, 2016 (6 pages).
Final Office Action for U.S. Appl. No. 14/509,870 dated Feb. 3, 2017 (16 pages).
Final Office Action for U.S. Appl. No. 14/873,296 dated Jan. 24, 2018 (17 pages).
Final Office Action for U.S. Appl. No. 15/244,138 dated Jun. 4, 2018 (15 pages).
Final Office Action for U.S. Appl. No. 15/244,138 dated Mar. 14, 2019 (14 pages).
Final Office Action for U.S. Appl. No. 15/668,451 dated May 24, 2018 (10 pages).
Final Office Action for U.S. Appl. No. 15/717,675 dated Jun. 27, 2019 (10 pages).
Final Office Action for U.S. Appl. No. 16/042,904 dated Nov. 1, 2019 (10 pages).
Final Office Action for U.S. Appl. No. 16/184,086 dated Jun. 9, 2020 (7 pages).
Final Office Action for U.S. Appl. No. 16/901,956 dated Aug. 6, 2021 (10 pages).
Final Office Action Response for U.S. Appl. No. 11/583,970 dated Feb. 4, 2010 (10 pages).
Final Office Action Response for U.S. Appl. No. 11/583,970 dated Jan. 28, 2009 (15 pages).
Final Rejection for KR 10-2009-7021320 dated May 29, 2013 (6 pages).
Final Rejection for KR 10-2010-7028384 dated Mar. 28, 2017 (6 pages).
First Office Action and Search Report for CN 201780082261.4 dated Jul. 28, 2020 (15 pages).
First Office Action for CN 200680045545.8 dated Dec. 31, 2010, English Translation Only (8 pages).
First Office Action for CN 200880015602.7 dated Jan. 31, 2012 (16 pages).
First Office Action for CN 200980126312.4 dated Jan. 30, 2012 (14 pages).
First Office Action for CN 200980127166.7 dated Dec. 5, 2012 (4 pages).
First Office Action for CN 201380048261.4 dated May 24, 2018 (17 pages).
First Office Action for CN 201410168106.2 dated Sep. 16, 2015 (9 pages).
First Office Action for CN 201410479685.2 dated Nov. 17, 2015 (12 pages).
First Office Action for CN 201480026147.6 dated Oct. 25, 2016 (13 pages).
First Office Action for CN 201480026500.0 dated Aug. 10, 2017 (22 pages).
First Office Action for CN 201510760532X dated May 11, 2018 (13 pages).
First Office Action for CN 201780052978.4 dated Sep. 23, 2021 (10 pages).
First Office Action for CN 201810243366.X dated Jan. 25, 2021 (11 pages).
Foreign Search Report and Written Opinion issued for SG Appl. Ser. No. 10201707390V dated Oct. 13, 2021 (9 pages).
Fourth Office Action for CN 200880015602.7 dated Nov. 11, 2013, English Translation Only (6 pages).
Fourth Office Action for CN 201410168106.2 dated Jun. 22, 2017 (8 pages).
Futaki, Chemistry and Biology (Kagaku to Seibutsu), vol. 43, No. 10, Oct. 1, 2005, pp. 649-653.
Gandarillas et al., "c-Myc promotes differentiation of human epidermal stem cells", Genes & Development, vol. 11, 1997, pp. 2869-2882 (15 pages).
Gauss et al., "DEAE-dextran enhances electroporation of mammalian cells", Nucleic Acids Research, vol. 20, No. 24, 1992, pp. 6739-6740 (2 pages).
Goeddel et al., "Direct expression in *Escherichia coli* of a DNA sequence coding for human growth hormone", Nature, vol. 281, Oct. 18, 1979, pp. 544-548 (5 pages).
Goeddel et al., "Synthesis of human fibroblast interferon by *E. coli*", Nucleic Acids Research, vol. 8, No. 18, Aug. 12, 1980, pp. 4057-4074 (18 pages).
Gross et al., "BCL-2 family members and the mitochondria in apaptosis", Genes & Development, vol. 13, No. 15, Aug. 1999, pp. 1899-1911 (14 pages).
Grumont et al., "The Mitogen-Induced Increase in T Cell Size Involves PKC and NFAT Activation of Rel/NF-kappaB-Dependent c-myc Expression", Immunity, vol. 21, Jul. 2004, pp. 19-30 (12 pages).
Guzman et al., "Preferential induction of apoptosis for primary human leukemic stem cells", Proceedings of the National Academy of Sciences, vol. 99, No. 25, Dec. 10, 2002, pp. 16220-16225, DOI: 10.1073/pnas.252462599 (6 pages).
Habib et al., "Myc Stimulates B lymphocyte differentiation and amplifies calcium signaling", The Journal of Cell Biology, vol. 179, No. 4, 2007, pp. 717-731, DOI: 10.1083/jcb.200704173 (11 pages).
Hann et al., "Proteins Encoded by the Human c-myc Oncogene: Differential Expression in Neoplastic Cells", Molecular and Cellular Biology, vol. 4, No. 11, Nov. 1984, pp. 2486-2497 (12 pages).
Henikoff et al., "Amino acid substitution matrices from protein blocks", Proceedings of the National Academy of Sciences USA, vol. 89, Nov. 1992, pp. 10915-10919 (5 pages).
Hiramatsu et al., "Complete reconstitution of human lymphocytes from cord blood CD34+ cells using the NOD/SCID/gamma-c-null mice model", Blood, vol. 102, No. 3, Aug. 1, 2003, pp. 873-880 (8 pages).
Hirose et al., "Immortalization of Erythroblasts by c-MYC and BCL-XL Enables Large-Scale Erythrocyte Production from Human Pluripotent Stem Cells", Stem Cell Reports, vol. 1, Dec. 17, 2013, pp. 99-508 (10 pages).
Ho et al., "Synthetic Protein Transduction Domains: Enhanced Transduction Potential in Vitro and in Vivo", Cancer Research, vol. 61, Jan. 15, 2001, pp. 474-477 (5 pages).
Hoffman, Ronald, "Progress in the development of systems for in vitro expansion of human hematopoietic stem cells", Current Opinion in Hematology, vol. 6, No. 3, 1999, pp. 184 (14 pages).
Horton et al., "Continuous MLL-ENL Expression Is Necessary to Establish a 'Hox Code' and Maintain Immortalization of Hematopoietic Progenitor Cells", Cancer Research, vol. 65, No. 20, Oct. 15, 2005, pp. 9245-9252, DOI: 10.1158/0008-5472.CAN-05-1691 (9 pages).
Hoshimaru et al., "Differentiation of the immortalized adult neuronal progenitor cell line HC2S2 into neurons by regulatable suppression of the v-myc oncogene", Proceedings of the National Academy of Sciences USA, Neurobiology, vol. No. 4, Feb. 1996, pp. 1518-1523 (6 pages).
Howard et al., "Transplantation of apoptosis-resistant embryonic stem cells into the injured rat spinal cord", Somatosensory and

(56) References Cited

OTHER PUBLICATIONS

Motor Research, vol. 22, No. 1/2, Mar./Jun. 2005, pp. 37-44, DOI: 10.1080/08990220500084909 (9 pages).
Huang et al., "Dynamic Regulation of c-Myc proto-oncogene expression during lymphocyte development revealed by a GFP-c-Myc knock-in mouse", European Journal of Immunology, vol. 38, No. 2, 2008, pp. 342-349, DOI: 10.1002/eji.200737972 (8 pages).
Huang et al., "Negative Control of the Myc Protein by the Stress-Responsive Kinase Pak2", Molecular and Cellular Biology, vol. 24, No. 4, Feb. 2004, pp. 1582-1594, DOI: 10.1128/MCB.24.4.1582-1594.2004 (13 pages).
Huettner et al., "Reversibility of acute B-cell leukaemia induced by BCR-ABL1", Nature Genetics, vol. 24, Jan. 2000, pp. 57-60 (4 pages).
International Preliminary Report on Patentability, Ch. I, for PCT/US09/55443 dated Mar. 1, 2011 (6 pages).
International Preliminary Report on Patentability, Ch. I, for PCT/US2006/040379 dated Apr. 23, 2008 (5 pages).
International Preliminary Report on Patentability, Ch. I, for PCT/US2008/056896 dated Sep. 15, 2009 (4 pages).
International Preliminary Report on Patentability, Ch. I, for PCT/US2008/082263 dated May 4, 2010 (6 pages).
International Preliminary Report on Patentability, Ch. I, for PCT/US2009/003105 dated Nov. 17, 2010 (6 pages).
International Preliminary Report on Patentability, Ch. I, for PCT/US2009/051242 dated Jan. 25, 2011 (6 pages).
International Preliminary Report on Patentability, Ch. I, for PCT/US2009/055443 dated Mar. 1, 2011 (6 pages).
International Preliminary Report on Patentability, Ch. I, for PCT/US2013/051384 dated Jan. 29, 2015 (10 pages).
International Preliminary Report on Patentability, Ch. I, for PCT/US2014/022971 dated Sep. 24, 2015 (8 pages).
International Preliminary Report on Patentability, Ch. I, for PCT/US2014/022977 dated Sep. 15, 2015 (9 pages).
International Preliminary Report on Patentability, Ch. I, for PCT/US2017/045336 dated Feb. 13, 2020 (8 pages).
International Preliminary Report on Patentability, Ch. I, for PCT/US2017/064206 dated Jun. 13, 2019 (13 pages).
International Preliminary Report on Patentability, Ch. I, for PCT/US2019/062200 dated Jun. 3, 2021 (9 pages).
International Preliminary Report on Patentability, Ch. I, for PCT/US2020/027070 dated Oct. 21, 2021 (9 pages).
International Search Report and Written Opinion for PCT/US17/45336 dated Nov. 3, 2017 (15 pages).
International Search Report and Written Opinion for PCT/US2006/040379 dated Sep. 24, 2007 (7 pages).
International Search Report and Written Opinion for PCT/US2008/056896 dated Aug. 14, 2008 (5 pages).
International Search Report and Written Opinion for PCT/US2008/082263 dated Jun. 25, 2009 (8 pages).
International Search Report and Written Opinion for PCT/US2009/003105 dated Jan. 15, 2010 (9 pages).
International Search Report and Written Opinion for PCT/US2009/051242 dated Feb. 19, 2010 (9 pages).
International Search Report and Written Opinion for PCT/US2009/055443 dated Jun. 30, 2010 (11 pages).
International Search Report and Written Opinion for PCT/US2013/051384 dated Nov. 13, 2013 (15 pages).
International Search Report and Written Opinion for PCT/US2014/022971 dated Aug. 13, 2014 (12 pages).
International Search Report and Written Opinion for PCT/US2014/022977 dated Aug. 28, 2014 (13 pages).
International Search Report and Written Opinion for PCT/US2017/064206 dated Mar. 19, 2018 (17 pages).
International Search Report and Written Opinion for PCT/US2018/044740 dated Oct. 16, 2018 (13 pages).
International Search Report and Written Opinion for PCT/US2019/062200 dated Jan. 16, 2020 (13 pages).
International Search Report and Written Opinion for PCT/US2020/027070 dated Sep. 18, 2020 (13 pages).
International Search Report and Written Opinion for PCT/US2020/032702 dated Nov. 18, 2020 (16 pages).
Invitation for EP 09810692.5 dated Feb. 25, 2014 (3 pages).
Invitation for EP 15175802.6 dated Jan. 31, 2017 (4 pages).
Invitation to Pay Additional Fees and, Where Applicable, Protest Fee for PCT/US2014/22971 dated May 27, 2014 (2 pages).
Invitation to Pay Additional Fees and, Where Applicable, Protest Fee, for PCT/US2020/027070 dated Jul. 21, 2020 (2 pages).
Iritani et al., "c-Myc enhances protein synthesis and cell size during B lymphocyte development", Proceedings of the National Academy of Sciences, vol. 96, No. 23, Nov. 9, 1999, pp. 13180-13185 (6 pages).
Iritani et al., "Modulation of T-lymphocyte development, growth and cell size by the Myc antagonist and transcriptional repressor Mad1", The EMBO Journal, vol. 21, No. 18, 2002, pp. 4820-4830 (11 pages).
Jadlowsky et al., "Dominant negative mutant Cyclin T1 proteins inhibit HIV transcription by specifically degrading Tat", Retrovirology, vol. 5, No. 63, 2008, DOI: 10.1186/1742-4690-5-63 (12 pages).
Jayapal et al., "Down-regulation of Myc Is Essential for Terminal Erythroid Maturation", Journal of Biological Chemistry, vol. 285, No. 51, Dec. 17, 2010, pp. 40252-40265, DOI: 10.1074/jbc.M110.181073 (14 pages).
Johnson et al., "Lymphomas with concurrent BCL2 and MYC translocations: the critical factors associated with survival", Blood, vol. 114, No. 11, Sep. 10, 2009, pp. 2273-2279 (7 pages).
Ju et al., "Anti-apoptotic therapy with a Tat fusion protein against excitotoxic insults in vitro and in vivo", Experimental Neurology, vol. 210, No. 2, 2008, pp. 602-607, DOI: 10.1016/j.expneurol.2007.12.008 (6 pages).
Kaptein et al., "Anti-IgM-mediated Regulation of c-myc and Its Possible Relationship to Apoptosis", The Journal of Biological Chemistry, vol. 271, No. 31, Aug. 2, 1996, pp. 18875-18884 (11 pages).
Karon et al., "Temporal sequence of major biochemical events during Blood Bank storage of packed red blood cells", Blood Transfusion, vol. 10, 2012, pp. 453-461, DOI: 10.2450/2012.0099-11 (9 pages).
Kashio et al., "A Protein Derived From the Fusion of TAT Peptide and FNK, a Bcl-XL Derivative, Prevents Cochlear Hair Cell Death From Aminoglycoside Ototoxicity In Vivo", Journal of Neuroscience Research, vol. 85, No. 7, 2007, pp. 1403-1412, DOI: 10.1002/jnr.21260 (10 pages).
Kelso et al., "Survival of the Myeloid Progenitor Cell Line FDC-P1 is Prolonged by Interferon-gamma or Interleukin-4", Growth Factors, vol. 6, No. 3, 1992, pp. 233-242 (10 pages).
Kitada et al., "Reversal of Chemoresistance of Lymphoma Cells by Antisense-Mediated Reduction of bcl-2 Gene Expression", Antisense Research and Development, vol. 4, 1994, pp. 71-79 (9 pages).
Korbling et al., "Allogeneic Blood Stem Cell Transplantation: Peripheralization and Yield of Donor-Derived Primitive Hematopoietic Progenitor Cells (CD34+Thy-Idim) and Lymphoid Subsets, and Possible Predictors of Engraftment and Graft-Versus-Host Disease", Blood, vol. 86, No. 7, Oct. 1, 1995, pp. 2842-2848 (7 pages).
Krosl et al., "In vitro expansion of hematopoietic stem cells by recombinant TAT-HOXB4 protein", Nature Medicine, vol. 9, No. 11, Nov. 2003, pp. 1428-1432, DOI: 10.1038/nm951 (5 pages).
Lang et al., "Mechanisms and Significance of Erypotosis, the Suicidal Death of Erythrocytes", Blood Purification, vol. 33, 2012, pp. 125-130, DOI: 10.1159/00034163 (6 pages).
Laurenti et al., "Hematopoietic Stem Cell Function and Survival Depend on c-Myc and N-Myc Activity", Cell Stem Cell, vol. 3, 2008, pp. 611-624, DOI: 10.1016/j.stem.2008.09.005 (14 pages).
Levesque et al., "The endosteal 'osteoblastic' niche and its role in hematopoietic stem cell homing and mobilization", Leukemia, vol. 24, 2010, pp. 1979-1992, DOI: 10.1038/leu.2010.214 (14 pages).
Li et al., "Reconstitution of functional human B lymphocytes in NOD/SCID mice engrafted with ex vivo expanded CD34+ cord blood cells", Experimental Hematology, vol. 30, 2002, pp. 1036-1043 (8 pages).

(56) References Cited

OTHER PUBLICATIONS

Littlewood et al., "A modified oestrogen receptor ligand-binding domain as an improved switch for the regulation of heterologous proteins", Nucleic Acids Research, vol. 23, No. 10, 1995, pp. 1686-1690 (5 pages).
MacPherson et al., "Activity-Dependent Gene Regulation in Conditionally-Immortalized Muscle Precursor Cell Lines," Journal of Cellular Biochemistry, vol. 91, No. 4, 2004, pp. 821-839, DOI: 10.1002/jcb.10784 (19 pages).
McCarthy, Nicola, "Underground movement", Nature Reviews: Cancer, vol. 7, Nov. 2007, DOI: 10.1038/nrc2257 (1 page).
McNiece et al, "Ex-vivo expansion of hematopoietic progenitor cells: preliminary results in breast cancer", Hematology and Cell Therapy, vol. 41, No. 2, 1999, pp. 82-86 DOI: 10.1007/s00282-999-0082-y (6 pages).
Melkonyan et al., "Electroporation efficiency in mammalian cells is increased by dimethyl sulfoxide (DMSO)", Nucleic Acids Research, vol. 24, No. 21, 1996, pp. 4356-4357, DOI: 10.1093/nar/24.21.4356 (2 pages).
Merino et al., "Developmental regulation of the Bcl-2 protein and susceptibility to cell death in B lymphocytes", The EMBO Journal, vol. 13, No. 3, 1994, pp. 683-691, DOI: 10.1002/j.1460-2075.1994.tb06307.x (9 pages).
Miharada et al., "Efficient enucleation of erythroblasts differentiated in vitro from hematopoietic stem and progenitor cells", Nature Biotechnology, vol. 24, No. 10, 2006, pp. 1255-1256, DOI: 10.1038/nbt1245 (2 pages).
Miller et al., "Expansion in vitro of adult murine hematopoietic stem cells with transplantable lympho-myeloid reconstituting ability", Proceedings of the National Academy of Sciences USA, vol. 94, Dec. 1997, pp. 13648-13653, DOI: 10.1073/pnas.94.25.13648 (6 pages).
Moore et al., "In Vitro Maintenance of Highly Purified, Transplantable Hematopoietic Stem Cells", Blood, vol. 89, No. 12, 1997, pp. 4337-4347, DOI: 10.1182/blood.V89.12.4337 (12 pages).
Mooslehner et al., "Retroviral Integration Sites in Transgenic Mov Mice Frequently Map in the Vicinity of Transcribed DNA Regions", Journal of Virology, vol. 64, 1990, pp. 3056-3058, DOI: 10.1128/jvi.64.6.3056-3058.1990 (3 pages).
Muchmore et al., "X-ray and NMR structure of human Bcl-XL, an inhibitor of programmed cell death", Nature, vol. 381, May 23, 1996, pp. 335-341, DOI: 10.1038/381335a0 (7 pages).
Murphy et al., "Id2 Is Dispensable for Myc-Induced Epidermal Neoplasia", Molecular and Cellular Biology, vol. 24, No. 5, Mar. 2004, pp. 2083-2090, DOI: 10.1128/MCB.24.5.2083-2090.2004 (8 pages).
Non Final Office Action for U.S. Appl. No. 11/583,970 dated May 9, 2011 (11 pages).
Non Final Office Action for U.S. Appl. No. 12/048,148 dated Oct. 13, 2011 (10 pages).
Non Final Office Action for U.S. Appl. No. 12/962,197 dated Aug. 26, 2011 (12 pages).
Non-Final Office Action for U.S. Appl. No. 11/583,970 dated Mar. 12, 2008 (16 pages).
Non-Final Office Action for U.S. Appl. No. 11/583,970 dated Mar. 23, 2009 (12 pages).
Non-Final Office Action for U.S. Appl. No. 11/583,970 dated Sep. 20, 2013 (20 pages).
Non-Final Office Action for U.S. Appl. No. 12/048,148 dated Jan. 19, 2011 (7 pages).
Non-Final Office Action for U.S. Appl. No. 12/048,148 dated May 11, 2012 (10 pages).
Non-final Office Action for U.S. Appl. No. 12/467,957 dated Apr. 4, 2014 (14 pages).
Non-Final Office Action for U.S. Appl. No. 12/467,957 dated Oct. 13, 2010 (15 pages).
Non-Final Office Action for U.S. Appl. No. 12/506,894 dated Apr. 27, 2012 (14 pages).
Non-Final Office Action for U.S. Appl. No. 12/506,894 dated Apr. 3, 2015 (16 pages).
Non-Final Office Action for U.S. Appl. No. 12/550,166 dated Jan. 11, 2012 (8 pages).
Non-Final Office Action for U.S. Appl. No. 12/701,383 dated Apr. 28, 2011 (10 pages).
Non-Final Office Action for U.S. Appl. No. 12/701,383 dated Jun. 13, 2014 (26 pages).
Non-Final Office Action for U.S. Appl. No. 13/795,659 dated Mar. 10, 2014 (12 pages).
Non-Final Office Action for U.S. Appl. No. 13/795,659 dated Nov. 26, 2014 (13 pages).
Non-Final Office Action for U.S. Appl. No. 13/797,648 dated Apr. 3, 2014 (14 pages).
Non-Final Office Action for U.S. Appl. No. 13/797,648 dated Apr. 19, 2018 (14 pages).
Non-Final Office Action for U.S. Appl. No. 13/797,648 dated Jun. 17, 2016 (17 pages).
Non-Final Office Action for U.S. Appl. No. 14/415,325 dated Dec. 23, 2016 (14 pages).
Non-Final Office Action for U.S. Appl. No. 14/461,105 dated Mar. 20, 2017 (7 pages).
Non-Final Office Action for U.S. Appl. No. 14/461,105 dated Mar. 22, 2016 (8 pages).
Non-Final Office Action for U.S. Appl. No. 14/509,870 dated Jul. 12, 2016 (21 pages).
Non-Final Office Action for U.S. Appl. No. 14/661,786 dated Aug. 27, 2015 (19 pages).
Non-Final Office Action for U.S. Appl. No. 14/873,296 dated Aug. 17, 2017 (18 pages).
Non-Final Office Action for U.S. Appl. No. 15/179,735 dated Feb. 26, 2018 (12 pages).
Non-Final Office Action for U.S. Appl. No. 15/244,138 dated Jan. 22, 2018 (28 pages).
Non-Final Office Action for U.S. Appl. No. 15/643,133 dated Nov. 1, 2019 (9 pages).
Non-Final Office Action for U.S. Appl. No. 15/668,451 dated Dec. 7, 2017 (15 pages).
Non-Final Office Action for U.S. Appl. No. 15/717,675 dated Feb. 14, 2019 (17 pages).
Non-Final Office Action for U.S. Appl. No. 15/785,000 dated Jun. 1, 2018 (10 pages).
Non-Final Office Action for U.S. Appl. No. 15/828,971 dated Jul. 8, 2019 (11 pages).
Non-Final Office Action for U.S. Appl. No. 16/042,904 dated Jul. 12, 2019 (12 pages).
Non-Final Office Action for U.S. Appl. No. 16/184,086 dated Feb. 13, 2020 (10 pages).
Non-Final Office Action for U.S. Appl. No. 16/261,207 dated May 13, 2020 (20 pages).
Non-Final Office Action for U.S. Appl. No. 16/742,082 dated Jan. 11, 2021 (10 pages).
Non-Final Office Action for U.S. Appl. No. 16/742,150 dated Sep. 28, 2021 (18 pages).
Non-Final Office Action for U.S. Appl. No. 16/901,956 dated Mar. 18, 2021 (13 pages).
Non-Final Office Action Response U.S. Appl. No. 11/583,970 dated Jun. 24, 2009 (11 pages).
Non-Final Office Action Response for U.S. Appl. No. 11/583,970 dated Aug. 12, 2008 (12 pages).
Non-Final Office Action Response for U.S. Appl. No. 12/701,383 dated Aug. 25, 2011 (20 pages).
Notice of Acceptance for AU 2009246876 dated Mar. 19, 2015 (3 pages).
Notice of Acceptance for AU 2009274172 dated Aug. 3, 2015 (2 pages).
Notice of Acceptance for AU 2012216462 dated Apr. 10, 2015 (2 pages).
Notice of Allowability for U.S. Appl. No. 15/643,133 dated Sep. 4, 2020 (2 pages).
Notice of Allowability for U.S. Appl. No. 16/184,086 dated Nov. 5, 2020 (2 pages).
Notice of Allowability for U.S. Appl. No. 16/261,207 dated Dec. 23, 2020 (4 pages).

(56) References Cited

OTHER PUBLICATIONS

Notice of Allowance for U.S. Appl. No. 11/583,970 dated Aug. 29, 2014 (11 pages).
Notice of Allowance for U.S. Appl. No. 12/467,957 dated Nov. 26, 2014 (7 pages).
Notice of Allowance for U.S. Appl. No. 12/506,894 dated Jun. 16, 2015 (8 pages).
Notice of Allowance for U.S. Appl. No. 12/550,166 date Nov. 26, 2012 (9 pages).
Notice of Allowance for U.S. Appl. No. 12/550,166 dated Apr. 28, 2014 (5 pages).
Notice of Allowance for U.S. Appl. No. 12/701,383 dated May 22, 2015 (9 pages).
Notice of Allowance for U.S. Appl. No. 13/777,967 dated Jul. 14, 2014 (11 pages).
Notice of Allowance for U.S. Appl. No. 13/795,659 dated Mar. 1, 2016 (8 pages).
Notice of Allowance for U.S. Appl. No. 13/795,659 dated Sep. 29, 2015 (11 pages).
Notice of Allowance for U.S. Appl. No. 13/797,648 dated Dec. 6, 2018 (9 pages).
Notice of Allowance for U.S. Appl. No. 14/415,325 dated Jun. 9, 2017 (13 pages).
Notice of Allowance for U.S. Appl. No. 14/461,105 dated Jun. 2, 2017 (7 pages).
Notice of Allowance for U.S. Appl. No. 14/509,870 dated Jun. 22, 2017 (10 pages).
Notice of Allowance for U.S. Appl. No. 14/661,786 dated Apr. 25, 2016 (9 pages).
Notice of Allowance for U.S. Appl. No. 15/179,735 dated May 29, 2018 (10 pages).
Notice of Allowance for U.S. Appl. No. 15/244,138 dated Jun. 5, 2019 (8 pages).
Notice of Allowance for U.S. Appl. No. 15/643,133 dated May 15, 2020 (8 pages).
Notice of Allowance for U.S. Appl. No. 15/668,451 dated Aug. 10, 2018 (7 pages).
Notice of Allowance for U.S. Appl. No. 15/717,675 dated Sep. 17, 2019 (7 pages).
Notice of Allowance for U.S. Appl. No. 15/785,000 dated Sep. 26, 2018 (7 pages).
Notice of Allowance for U.S. Appl. No. 15/828,971 dated Nov. 1, 2019 (7 pages).
Notice of Allowance for U.S. Appl. No. 16/042,904 dated Dec. 11, 2019 (7 pages).
Notice of Allowance for U.S. Appl. No. 16/042,904 dated Mar. 20, 2020 (7 pages).
Notice of Allowance for U.S. Appl. No. 16/184,086 dated Aug. 26, 2020 (7 pages).
Notice of Allowance for U.S. Appl. No. 16/261,207 dated Nov. 16, 2020 (7 pages).
Notice of Allowance for U.S. Appl. No. 16/742,082 dated Apr. 14, 2021 (6 pages).
Notice of Defects for IL 224494 dated Apr. 23, 2017 (2 pages).
Notice of Defects for IL 232432 dated May 22, 2016.
Notice of Supplementary European Search Report for EP 06826025.6 dated Sep. 1, 2009 (3 pages).
Notification of Defects for IL 190946 dated May 14, 2015, English Translation Only (2 pages).
Notification of Defects for IL 190946 dated Jul. 3, 2012, English Translation Only (1 page).
Notification of Defects for IL 200919 dated Jan. 17, 2013 (4 pages).
Notification of Defects for IL 2053539 dated Jun. 26, 2016 (106576-0111).
Notification of Defects for IL 208810 dated Jan. 2, 2013, English Translation Only (4 pages).
Notification of Defects for IL 208810 dated Sep. 18, 2017 (106576-0111).
Notification of Defects for IL 209343 dated Aug. 14, 2012 (3 pages).
Notification of Defects for IL 209968 dated Aug. 21, 2012 (4 pages).
Notification of Defects for IL 236763 dated Sep. 17, 2018 (8 pages).
Notification of Defects for IL 241192 dated Dec. 1, 2019 (4 pages).
Notification of Defects for IL 24199 dated Nov. 29, 2017, English Translation Only (2 pages).
Notification of Defects for IL 249700 dated Nov. 18, 2018 (3 pages).
Notification of Defects for IL 249700 dated Nov. 23, 2017 (2 pages).
Notification of Defects for IL 265409 dated Jun. 22, 2020 (8 pages).
Notification of Defects for IL 266009 dated Dec. 25, 2019 (5 pages).
Notification of Defects for IL 272532 dated Jun. 8, 2020 (8 pages).
Notification of Defects for IL 272532 dated Nov. 15, 2020 (8 pages).
Notification of Defects IL 266009 dated Jun. 29, 2020 (3 pages).
Notification of Detects for IL 200919 dated Dec. 5, 2011, English Translation Only (2 pages).
Notification of Detects for IL 266867 dated Oct. 24, 2020 (3 pages).
Notification prior to Allowance for IL 209343 dated Apr. 7, 2014, English Translation Only (2 pages).
Notification Prior to Examination for IL 232432 dated May 15, 2014, English translation only (3 pages).
Notification Prior to Examination for IL 208810 dated Nov. 2, 2011, English Translation Only (3 pages).
Notification Prior to Examination for IL 209343 dated Nov. 2, 2011, English Translation Only (3 pages).
Notification Prior to Examination for IL 209968 dated Nov. 2, 2011, English Translation Only (3 pages).
Notification Prior to Examination for IL 241192 dated Dec. 13, 2015.
Notification Prior to Examination for IL 241299 dated Dec. 15, 2015.
Notification Prior to Examination for IL 264977 dated Feb. 16, 2020.
Notification Prior to Examination for IL 265409 dated Mar. 19, 2019.
Notification Prior to Examination for IL 266867 dated May 10, 2020.
Notification Prior to Examination for IL 272147 dated Nov. 1, 2020.
Notification Prior to Examination for IL 272532 dated Feb. 9, 2020.
Notification Prior to Examination for IL 278426 dated Nov. 4, 2020.
Notification Prior to Examination for IL 278426 dated Sep. 5, 2021.
Notification Prior to Examination for IL 280751 dated Feb. 11, 2021.
Notification Prior to Examination for IL 284998 dated Jul. 22, 2021.
Office Action for EU 201001762/28 dated Oct. 16, 2013, English Translation Only (1 page).
Office Action for IL 190946 dated Apr. 22, 2013, English Translation Only (1 page).
Office Action for IL 200919 dated May 19, 2014, English Translation Only (3 pages).
Office Action for IL 208810 dated Jan. 13, 2015, English Translation Only (3 pages).
Office Action for IL 208810 dated Jun. 27, 2018 (2 pages).
Office Action for IL 209968 dated Jan. 2, 2014, English Translation Only (2 pages).
Office Action for IL 232432 dated Mar. 8, 2015, English Translation Only (3 pages).
Office Action for IL 241192 dated Jul. 30, 2018 (6 pages).
Office Action for IL 256512 dated Jul. 29, 2018 (5 pages).
Office Action for KR 10-2008-7011791 dated Jan. 15, 2014 (6 pages).
Office Action for KR 10-2008-7011791 dated May 28, 2013 (6 pages).
Office Action for KR 10-2009-7021320 dated Jul. 29, 2011 (7 pages).
Office Action for KR 10-2009-7021320 dated Sep. 18, 2012 (11 pages).
Office Action for KR 10-2010-7028384 dated Aug. 18, 2016 (12 pages).
Office Action for KR 10-2013-7020078 dated Sep. 17, 2014 (8 pages).
Office Action for KR 10-2013-7028338 dated Jan. 15, 2014 (3 pages).
Office Action for MX MX/a/2015/012168 dated Aug. 31, 2018 (5 pages).

(56) References Cited

OTHER PUBLICATIONS

Okuyama, et al., "Abotosis and oncogenes", The Medical Frontline, vol. 49, No. 6, 2003, pp. 1096-1101 (13 pages).
Opferman et al., "Anti-apoptotic BCL-2 family members in development", Cell Death and Differentiation, vol. 25, 2018, pp. 37-45, DOI: 10.1038/ckk.2017.170 (9 pages).
Oral Proceedings Summons for EP 08743862.8 dated May 14, 2012 (6 pages).
Ouyang, et al., "Pathophysiology: the Mechanism of Disease and the Basis of Prevention and Treatment", Wuhan University Press, 1st Ed., pp. 128-129 (8 pages).
Pan et al., "Reprogramming human fibroblasts using HIV-1 TAT recombinant proteins OCT4, SOX2, KLF4 and c-MYC", Molecular Biology Reports, vol. 37, 2010, pp. 2117-2124, DOI: 10.1007/s11033-009-9680-6 (8 pages).
Partial Supplementary European Search Report for EP 13820331.0 dated Jun. 30, 2016 (6 pages).
Partial Supplementary European Search Report for EP 14778538.0 dated Jul. 8, 2016 (7 pages).
Patel et al., "The c-MYC Oncoprotein Is a Substrate of the Acetyltransferases hGCN5/PCAF and TIP60", Molecular and Cellular Biology, vol. 24, No. 24, Dec. 2004, pp. 10826-10834, DOI: 10.1128/MCB.24.24.10826-10834.2004 (9 pages).
Patent Examination Report No. 1 for AU 2006304392 dated Jul. 16, 2012 (3 pages).
Patent Examination Report No. 1 for AU 2009246876 dated Jan. 17, 2014 (6 pages).
Patent Examination Report No. 1 for AU 2009274172 dated Jul. 24, 2014 (3 pages).
Patent Examination Report No. 1 for AU 2012216462 dated Mar. 6, 2014 (3 pages).
Patent Examination Report No. 1 for AU 2014249202 dated Nov. 18, 2015 (2 pages).
Patent Examination Report No. 1 for AU 2015205879 dated Mar. 15, 2016 (9 pages).
Penuela et al., "Erythropoietin reduces storage lesions and decreases apoptosis indices in blood bank red blood cells", Brazilian Journal of Hematology and Hemotherapy, vol. 38, No. 1, 2016, pp. 15-20 (6 pages).
Pierelli et al., "Modulation of bcl-2 and p27 in human primitive proliferating hematopoietic progenitors by autocrine TGF-beta1 is a cell cycle-independent effect and influences their hematopoietic potential," Blood, vol. 95, 2000, pp. 3001-3010 (10 pages).
Pinto Do O et al., "Hematopoietic progenitor/stem cells immortalized by Lhx2 generate functional hematopoietic cells in vivo", Blood, vol. 99, No. 11, 2002, pp. 3939-3946 (9 pages).
Podsypanina et al., "Oncogene cooperation in tumor maintenance and tumor recurrence in mouse mammary tumors induced by Myc and mutant Kras", Proceedings of the National Academy of Sciences, vol. 105, No. 13, 2008, pp. 5242-5247 (6 pages).
Polenakovic et al., "Is Erythropoietin a Survival Factor for Red Blood Cells?" Journal of the American Society of Nephrology, vol. 7,, No. 8, 1996, pp. 1178-1182, DOI: 10.1681/ASN.V781178 (5 pages).
Pollock et al., "A conditionally immortal clonal stem cell line from human cortical neuroepithelium for the treatment of ischemic stroke", Experimental Neurology, vol. 199, No. 1, 2006, pp. 143-155, DOI: 10.1016/j.expneurol.2005.12.011 (13 pages).
Pre-Appeal Examination Report for JP 2014-108137 dated Dec. 7, 2016 (15 pages).
Prochownik et al., "Deregulated expression of c-myc by murine erythroleukaemia cells prevents differentiation", Nature, vol. 322, Aug. 28, 1986, pp. 848-850 (3 pages).
Qin et al., "Nuclear Factor kappaB Nuclear Translocation Upregulates c-Myc and p53 Expression during NMDA Receptor-Mediated Apoptosis in Rat Striatum", The Journal of Neuroscience, vol. 19, No. 10, May 15, 1999, pp. 4023-4033 (11 pages).
Rabbitts et al., "Metabolism of c-myc gene products: c-myc mRNA and protein expression in the cell cycle", The EMBO Journal, vol. 4, No. 8, 1985, pp. 2009-2015 (7 pages).
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270, DOI: 10.1158/0008-5472.CAN-05-3940 (7 pages).
Raymon et al., "Immortalized Human Dorsal Root Ganglion Cells Differentiate into Neurons with Nociceptive Properties", The Journal of Neuroscience, vol. 19, No. 13, 1999, pp. 5420-5428 (9 pages).
Re-Examination Report for AU 2009285547 dated Apr. 23, 2015 (3 pages).
Reason for Refusal for KR 10-2017-7017674 dated Oct. 23, 2017 (12 pages).
Reasons for Refusal for JP 2008-536713 dated Jul. 3, 2012 (6 pages).
Reasons for Refusal for JP 2009-553785 dated Jun. 19, 2012 (7 pages).
Reasons for Refusal for JP 2009-553785 dated Apr. 22, 2014 (10 pages).
Reasons for Refusal for JP 2011-520133 dated Feb. 5, 2014 (9 pages).
Reasons for Refusal for JP 2011-525258 dated Feb. 17, 2014 (8 pages).
Reasons for Refusal for JP 2012-221023 dated Apr. 22, 2014 (4 pages).
Reasons for Refusal for JP 2016-501117 dated Dec. 17, 2018 (4 pages).
Reasons for Refusal for JP 2017-123838 dated Jul. 18, 2018 (6 pages).
Reasons for Refusal for JP 2017-166334 dated Apr. 24, 2019 (6 pages).
Reasons for Refusal for JP 2017-166334 dated Oct. 22, 2018 (7 pages).
Reasons for Refusal for JP 2018-048138 dated Feb. 12, 2019 (6 pages).
Reasons for Refusal for JP 2018-153567 dated Jul. 25, 2019 (8 pages).
Reasons for Refusal for JP 2019-006759 dated Feb. 20, 2020 (5 pages).
Reasons for Refusal for JP 2019-138912 dated Jun. 15, 2020 (7 pages).
Reasons for Refusal for JP 2019-512193 dated May 13, 2020 (6 pages).
Reasons for Refusal for JP 2020-193475 dated Oct. 25, 2021 (4 pages).
Reasons for Rejection for JP 2014-108137 dated Aug. 18, 2015 (12 pages).
Reasons for Rejection for JP 2014-108137 dated Nov. 1, 2017 (13 pages).
Reasons for Rejection for JP 2015-075703 dated Dec. 8, 2016 (6 pages).
Reasons for Rejection for JP 2015-075703 dated May 11, 2016 (11 pages).
Reasons for Rejection for JP 2015-523297 dated Apr. 3, 2017 (8 pages).
Reasons for Rejection for JP 2015-523297 dated Jul. 19, 2017 (8 pages).
Reasons for Rejection for JP 2016-027812 dated Mar. 1, 2017 (9 pages).
Reasons for Rejection for JP 2016-501113 dated Dec. 28, 2017 (13 pages).
Reasons for Rejection for JP 2016-501117 dated Apr. 17, 2017 (11 pages).
Reasons for Rejection for JP 2016-501117 dated Nov. 15, 2017 (9 pages).
Reasons for Rejection for JP 2018-017287 dated Apr. 18, 2019 (13 pages).
Reasons for Rejection for JP 2019-006759 dated Aug. 6, 2020 (4 pages).
Reasons for Rejection for JP 2019-025374 dated Mar. 9, 2020 (8 pages).
Reasons for Rejection for JP 2019-138912 dated Oct. 21, 2020 (6 pages).
Reasons for Rejection for JP 2019-512193 dated Sep. 30, 2019 (8 pages).

(56) References Cited

OTHER PUBLICATIONS

Reasons for Rejection for JP 2019-529651 dated Jul. 15, 2020 (6 pages).
Reasons for Rejection for JP 2020-115359 dated Jul. 28, 2021 (6 pages).
Reasons for Rejection for JP 2020-119082 dated Aug. 23, 2021 (6 pages).
Reasons for Rejection for JP 2020-119610 dated Jul. 12, 2021 (6 pages).
Reasons of Refusal for JP 2012-221023 dated Jun. 24, 2014, English Translation Only (2 pages).
Reexamination Notification for CN 201380048261.4 dated May 11, 2021 (16 pages).
Refaeli et al., "The B Cell Antigen Receptor and Overexpression of MYC Can Cooperate in the Genesis of B-Cell Lymphomas", PLOS Biology, vol. 6, Issue 6, e152, 2008, pp. 1208-1225, DOI: 10.1371/journal.pbio.0060152 (18 pages).
Refaeli et al., "The protooncogene MYC can break B cell tolerance", Proceedings of the National Academy of Sciences, vol. 102, No. 11, Mar. 2005, pp. 4097-4102, DOI: 10.1073/pnas.0409832102 (6 pages).
Request for ReExamination for CN 200680045545.8 dated Oct. 12, 2012 (17 pages).
Response for EP 09800871.7 dated Feb. 6, 2013 (9 pages).
Response for EP 09800871.7 dated Jan. 20, 2012 (5 pages).
Response for EP 09800871.7 dated Jul. 10, 2012 (5 pages).
Response for EP 09810692.5 dated Jan. 31, 2012 (7 pages).
Response for EP 09810692.5 dated Jul. 30, 2012 (5 pages).
Response to Final Office Action for U.S. Appl. No. 11/583,970 dated Feb. 16, 2012 (14 pages).
Response to Final Office Action for U.S. Appl. No. 12/701,383 dated Feb. 15, 2012 (13 pages).
Response to First Office Action for CN 200680045545.8 dated Jul. 15, 2011 (22 pages).
Response to Office Action for JP 2008-536713 dated Oct. 3, 2012 (21 pages).
Response to Second Office Action for CN 200680045545.8 dated Jan. 30, 2012 (23 pages).
Restriction Requirement for U.S. Appl. No. 11/583,970 dated Nov. 13, 2007 (14 pages).
Restriction Requirement for U.S. Appl. No. 12/701,383 dated Jan. 25, 2011 (10 pages).
Richter et al., "Lhx2 expression in hematopoietic progenitor/stem cells in vivo causes a chronic myeloproliferative disorder and altered globin expression", Journal of Hematology, vol. 88, No. 12, 2003, pp. 1336-1347 (12 pages).
Roh et al., "Transgenic Mice for Cre-Inducible Overexpression of the Oncogenes c-MYC and Pim-1 in Multiple Tissues", Genesis: The Journal of Genetics and Development, vol. 44, 2006, pp. 447-453, DOI: 10.1002/dvg.20235 (7 pages).
Rosenwald et al., "Increased expression of eukaryotic translation initiation factors eIF-4E and eIF-2alpha in response to growth induction by c-myc", Proceedings of the National Academy of Sciences USA, vol. 90, 1993, pp. 6175-6178 (4 pages).
Rubinstein et al., "Ex Vivo Interleukin-12-Priming During CD8+ T Cell Activation Dramatically Improves Adoptive T Cell Transfer Antitumor Efficacy in a Lymphodepleted Host", Journal of the American College of Surgeons, vol. 214, No. 4, 2002, pp. 700-707 (8 pages).
Rudolph et al., "Expression of Mad1 in T cells leads to reduced thymic cellularity and impaired mitogen-induced proliferation", Oncogene, vol. 20, 2001, pp. 1164-1175 (12 pages).
Satoh et al, "Roles for c-Myc in Self-renewal of Hematopoietic Stem Cells", The Journal of Biological Chemistry, vol. 279, No. 24, 2004, pp. 24986-24993, DOI: 10.1074/jbc.M400407200 (9 pages).
Sauer, Brian "Inducible Gene Targeting in Mice Using the Cre/lox System", Methods: A Companion to Methods in Enzymology, vol. 14, No. ME980593, 1998, pp. 381-392 (12 pages).
Schiedlmeier et al., "High-level ectopic HOXB4 expression confers a profound in vivo competitive growth advantage on human cord blood CD34+ cells, but impairs lymphomyeloid differentiation", Blood, vol. 101, No. 5, Mar. 1, 2003, pp. 1759-1768, DOI: 10.1182/blood-2002-03-0767 (10 pages).
Schmidt et al., "Transgenic mice bearing the human c-myc gene activated by an immunoglobulin enhancer: A pre-B-cell lymphoma model", Proceedings of the National Academy of Sciences, vol. 85, Aug. 1988, pp. 6047-6051 (5 pages).
Schneider et al., "Pharmacologic shifting of a balance between protein refolding and degradation mediated by Hsp90", Proceedings of the National Academy of Sciences, Cell Biology, vol. 93, Dec. 1996, pp. 14536-14541 (6 pages).
Schroy et al., "A Simple Method for Freezing and Thawing Cultured Cells," Methods in Cell Science (formerly known as TCA Manual), vol. 2, No. 1, 1976, pp. 309-310 (2 pages).
Schwarze et al., "In vivo protein transduction: intracellular delivery of biologically active proteins, compounds and DNA", Trends in Pharmacological Sciences, vol. 21, Feb. 2000, pp. 45-48 (4 pages).
Schwarze et al., "Protein transduction: unrestricted delivery into all cells?" Trends in Cell Biology, vol. 10, Jul. 2000, pp. 290-295 (6 pages).
Search Report and Written Opinion for SG 10201700459X dated Mar. 9, 2021 (13 pages).
Search Report and Written Opinion for SG 11202000612T dated Jul. 29, 2021 (9 pages).
Search Report for SG 10201700459X dated Feb. 1, 2021 (4 pages).
Second Office Action for CN 200680045545.8 dated Sep. 15, 2011, English Translation Only (9 pages).
Second Office Action for CN 200880015602.7 dated Oct. 31, 2012 (10 pages).
Second Office Action for CN 200980126312.4 dated Aug. 28, 2012 (12 pages).
Second Office Action for CN 200980127166.7 dated Jun. 10, 2013, English Translation Only (1 page).
Second Office Action for CN 201410168106.2 dated May 26, 2016 (5 pages).
Second Office Action for CN 201410479865.2 dated Jul. 5, 2016 (6 pages).
Second Office Action for CN 201480026147.6 dated Apr. 20, 2017 (11 pages).
Second Office Action for CN 201480026500.0 dated Apr. 27, 2018 (5 pages).
Second Office Action for CN 201510760532.X dated Jan. 10, 2020 (14 pages).
Second Office Action for CN 201780082261.4 dated Feb. 26, 2021 (5 pages).
Seibutsugaku Jiten (Dictionary of Biology), Iwanami Shoten, The 4th edition, 1997, p. 1396 (2 pages).
Siebenlist et al., "E. coli RNA Polymerase Interacts Homologously with Two Different Promoters", Cell, vol. 20, Jun. 1980, pp. 269-281 (13 pages).
Silva et al., "Erythropoietin Can Promote Erythroid Progenitor Survival by Repressing Apoptosis Through Bcl-XL and Bcl-2", Blood, vol. 88, No. 5, Sep. 1, 1996, pp. 1576-1582 (8 pages).
Sipione et al., "Modeling Brain Pathologies Using Neural Stem Cells", Methods in Molecular Biology, vol. 198, 2002, pp. 245-262 (18 pages).
Snyder et al., "Regulation of NMDA receptor trafficking by amyloid-beta", Nature Neuroscience, 2005, vol. 8, No. 8, pp. 1051-1058, DOI: 10.1038/nn1503 (8 pages).
Soane et al., "TAT-mediated endocytotic delivery of the loop deletion Bcl-2 protein protects neurons against cell death", Journal of Neurochemistry, vol. 95, 2005, pp. 230-243, DOI: 10.1111/j.1471-4159.2005.03359.x (14 pages).
Song, "Cloning and expression of PTD-BDNF fusion gene and purification of expressed product", Bioengineering Pharmaceutical Research and Practice, Anhui Science and Technology Press, 1st Ed., Feb. 2009, pp. 200-201 (3 pages).
Stein et al., "TAT-MYC Recombinant Fusion Protein Enhances Hematopoietic Stem Cell Graft Performance and Immunne Cell Reconstitution after Transplantation," Blood, vol. 130, Suppl. 1, Dec. 7, 2017, pp. 3175 (2 pages).

(56) References Cited

OTHER PUBLICATIONS

Stevenson et al., "HIV-1 replication is controlled at the level of T cell activation and proviral integration", The EMBO Journal, vol. 9, No. 5, 1990, pp. 1551-1560 (10 pages).
Strasser et al., "Novel primitive lymphoid tumours induced in transgenic mice by cooperation between myc and bcl-2", Letters to Nature, vol. 348, 1990, pp. 331-333 (3 pages).
Sunyer, J. Oriol, "Evolutionary and Functional Relationships of B Cells from Fish and Mammals: Insights into their Novel Roles in Phagocytosis and Presentation of Particulate Antigen", Infectious Disorders—Drug Targets, vol. 12, No. 3, 2012, pp. 200-212 (24 pages).
Supplementary European Search Report for EP 08743862.8 dated Mar. 31, 2010 (1 page).
Taguchi et al., "Nuclear trafficking of macromolecules by an oligopeptide derived from Vpr of human immunodeficiency virus type-1", Biochemical and Biophysical Research Communications, vol. 320, No. 1, 2004, pp. 18-26 (10 pages).
Takahashi et al., Induction of Pluripotent Stem Cells from Mouse Embryonic and Adult Fibroblast Cultures by Defined Factors, Cell, vol. 126, Aug. 2006, pp. 663-676, DOI: 10.1016/j.cell.2006.07.024 (14 pages).
Theis et al., "Expression of the myc/His-Tagged Human Peptide Transporter hPEPT1 in Yeast for Protein Purification and Functional Analysis", Protein Expression and Purification, 2001, vol. 22, pp. 436-442 (7 pages).
Third Office Action for CN 200680045545.8 dated Feb. 15, 2015, English Translation Only (4 pages).
Third Office Action for CN 200880015602.7 dated May 9, 2013 (13 pages).
Third Office Action for CN 200980127166.7 dated Apr. 11, 2014 (6 pages).
Third Office Action for CN 201410168106.2 dated Nov. 28, 2016 (11 pages).
Third Office Action for CN 201480026147.6 dated Sep. 28, 2017 (5 pages).
Third Office Action for CN 201510760532.X Jul. 13, 2020 (12 pages).
Thomas et. al., "Progress and Problems with the Use of Viral Vectors for Gene Therapy", Nature, vol. 4, May 2003, pp. 346-358, DOI: 10.1038/nrg1066 (13 pages).
Trumpp et al., "c-Myc regulates mammalian body size by controlling cell number but not cell size", Nature, vol. 414, Dec. 2001, pp. 768-773 (6 pages).
Tsai et al., "Lymphohematopoietic progenitors immortalized by a retroviral vector harboring a dominant-negative retinoic acid receptor can recapitulate lymphoid, myeloid, and erythroid development", Genes & Development, vol. 8, 1994, pp. 2831-2841, DOI: 10.1101/gad.8.23.2831 (12 pages).
Varnum-Finney et al., "Pluripotent, cytokine-dependent, hematopoietic stem cells are immortalized by constitutive Notch1 signaling", Nature Medicine, vol. 6, No. 11, 2000, pp. 1278-1281 (4 pages).
Vaux et al., "Bcl-2 gene promotes hemopoietic cell survival and cooperates with c-myc to immortalize pre-B cells", Nature, vol. 335, Sep. 29, 1988, pp. 440-442 (3 pages).
Vaux et al., "Immunologic competence of B cells subjected to constitutive c-myc oncogene expression in immunoglobulin heavy chain enhancer myc transgenic mice", The Journal of Immunology, vol. 139, No. 11, Dec. 1987, pp. 3854-3860 (7 pages).
Wagner et al., "Myc-Mediated Apoptosis Is Blocked by Ectopic Expression of Bcl-2", Molecular and Cellular Biology, vol. 13, No. 4, Apr. 1993, pp. 2432-2440 (9 pages).
Wang et al., "Primitive Human Hematopoietic Cells Are Enriched in Cord Blood Compared With Adult Bone Marrow or Mobilized Peripheral Blood as Measured by the Quantitative In Vivo SCID-Repopulating Cell Assay", Blood, vol. 89, 1997, pp. 3919-3924 (6 pages).
Wang, Wei, "Instability, stabilization, and formulation of liquid protein pharmaceuticals", International Journal of Pharmaceutics, vol. 185, Issue 2, Aug. 20, 1999, pp. 129-188 (60 pages).

Wang, Wei, "Lyophilization and development of solid protein pharmaceuticals", International Journal of Pharmaceutics, vol. 203, Issues 1-2, Aug. 2000, pp. 1-60 (60 pages).
Watt et al., "Nucleotide sequence of cloned cDNA of human c-myc oncogene", Nature, vol. 303, 1983, pp. 725-728 (4 pages).
Wechsler et al., "MXI1, a Putative Tumor Suppressor Gene, Suppresses Growth of Human Glioblastoma Cells", Cancer Research, vol. 57, 1997, pp. 4905-4912 (8 pages).
Wilson et al., "c-Myc controls the balance between hematopoietic stem cell self-renewal and differentiation", Genes and Development, vol. 18, 2004, pp. 2747-2763, DOI: 10.1101/gad.313104 (18 pages).
Wu et al., "Fusion Protein Vectors to Increase Protein Production and Evaluate the Immunogenicity of Genetic Vaccines", Molecular Therapy, vol. 2, No. 3, Sep. 2000, pp. 288-297, DOI: 10.1006/mthe.2000.0126 (10 pages).
Wu et al., "Inhibition of c-myc Expression Induces Apoptosis of WEHI 231 Murine B Cells", Molecular and Cellular Biology, vol. 16, No. 9, Sep. 1996, pp. 5015-5025 (11 pages).
Wurm et al., "Large-scale transient expression of mammalian cells for recombinant protein production", Current Opinion in Biotechnology, vol. 10, 1999, pp. 156-159 (4 pages).
Xi et al., "In Vitro Large Scale Production of Human Mature Red Blood Cells from Hematopoietic Stem Cells by Coculturing with Human Fetal Liver Stromal Cells", BioMed Research International, vol. 2013, Article ID 807863, Jan. 30, 2013, DOI: 10.1155/2013/807863 (12 pages).
Xu Zhixiang, et al, "The Development of the Study on the Anti-Tumor Effect of Flt3 Ligand," Chinese Journal of Tumor Biological Therapy, vol. 7, No. 3, Sep. 30, 2000 (2 pages).
Yagihashi et al., "Detection of Anti-Survivin Antibody in Gastrointestinal Cancer Patients", Clinical Chemistry, vol. 47, No. 9, Sep. 2001, pp. 1729-1731, DOI: doi.org/10.1093/clinchem/47.9.1729 (3 pages).
Yakuzaigaku, Pharmaceutics, vol. 64, No. 3, 2004, pp. 164-167 (4 pages).
Yanai et al., "A novel stromal cell-dependent hematopoietic cell line established from temperature-sensitive SV40 T-antigen transgenic mice", Experimental Hematology, vol. 27, 1999, pp. 1087-1096 (10 pages).
Young et al., "B-cell receptor signaling in the genesis and maintenance of B-cell lymphoma", Future Oncology, vol. 4, No. 5, 2008, pp. 591-594, DOI: 10.2217/14796694.4.5.591 (4 pages).
Yu et al., "Oncology Clinical Bulletin", Shandong Science and Technology Press, 2004 (28 pages).
Zhang et al., "Cytokines regulating hematopoietic stem cell function", Current Opinion in Hematology, vol. 15, No. 4, Jul. 2008, pp. 307-311, DOI: 10.1097/MOH.0b013e3283007db5 (8 pages).
Zhang et al., "Reprogramming of somatic cells via TAT-mediated protein transduction of recombinant factors", Biomaterials, vol. 33, 2012, pp. 5047-5055, DOI: 10.1016/j.biomaterials.2012.03.061 (9 pages).
Zhuang et al., "C-MYC overexpression is required for continuous suppression of oncogene-induced senescence in melanoma cells", Oncogene, vol. 27, 2008, pp. 6623-6634 (12 pages).
Office Action issued in Canadian Application No. 2905296 dated Feb. 15, 2022.
European Communication pursuant to Article 94(3) issued in European Application No. 19157513.3 dated Mar. 3, 2022.
Notice of Reasons for Rejection issued in Japanese Application No. 2021-037508, dated Mar. 31, 2022, English Translation.
De Clercq, E., "New Nucleotide Analogues for the Treatment of Hemorrhagic Fever Virus Infections." Chem. Asian J., 2019, vol. 14, pp. 3962-3968.
Duraffour, et al., "How to treat Ebola virus infections? A lesson from the field." Current Opinion in Virology, 2017, vol. 24, pp. 9-15.
Fanale, et al., "Monoclonal Antibodies in the Treatment of Non-Hodgkin's Lymphoma." Drugs, 2007, vol. 3, pp. 333-350.
Foreign Action other than Search Report on CN 201910023181.2 dtd Sep. 15, 2022.
Foreign Action other than Search Report on CN 201910848417.6 dtd Nov. 3, 2022, 15 pages.

(56) References Cited

OTHER PUBLICATIONS

Foreign Action other than Search Report on EP 20212922.7 dtd Sep. 1, 2022.
Gibson, et al., "How we evaluate and treat neutropenia in adults." Blood, 2014, vol. 124, No. 8, pp. 1251-1258.
Jacobson, et al., "How I treat Burkitt lymphoma in adults." Blood, 2014, vol. 124, No. 19, pp. 2913-2920.
Namikawa, et al., "A case of ABO-incompatible blood transfusion treated by plasma exchange therapy and continuous hemodiafiltration." CEN Case Reports, 2018, vol. 7, pp. 114-120.
Yu, et al., "Chapter 1: Clinical Overview of Cancer," Clinical References for Cancers (Chinese), May 31, 2004, pp. 151 and 152.
Hann, et al., "The alternatively initiated c-Myc proteins differentially regulate transcription through a noncanonical DNA-binding site." Genes & Development, 1994, No. 8, pp. 2441-2452.
Non-Final Office Action on U.S. Appl. No. 16/635,383 dated Jun. 29, 2022.
Yu et al., "Molecular Biology" (in Chinese), Nanjing Normal University Press, Jul. 2007, pp. 158 and 159 (English Translation).
Zhu et al., "Modern Molecular Biology" (in Chinese), Higher Education Press, Mar. 1997, p. 422 (English Translation).

\* cited by examiner

| | CD86-PE AVG | | | |
|---|---|---|---|---|
| | Single Cell/ Lymphocytes/ CD4, SSC-A subset \| Count | Single Cell/ Lymphocytes/ CD4, SSC-A subset \| Freq. of Parent (%) | Single Cell/ Lymphocytes/ CD4, SSC-A subset \| Median (Comp-PE-A) | Single Cell/ Lymphocytes/ CD4, SSC-A subset/CD86, SSC-A subset \| Freq. of Parent (%) |
| 072418-47F PBMC - CD3-0 CD28-0 | 4317 | 42.4 | 136 | 7.505 |
| 072418-47F PBMC - CD3-6 CD28-0.62 | 3867 | 60.3 | 699 | 65.0 |
| 072418-47F PBMC - CD3-6 CD28-2.0 | 3624 | 59.3 | 655 | 60.6 |
| 072518-60M TBX3400 - CD3-0 CD28-0 | 7575 | 62.9 | 161 | 14.3 |
| 072518-60M TBX3400 - CD3-6 CD28-0.62 | 5556 | 58.1 | 448 | 41.0 |
| 072518-60M TBX3400 - CD3-6 CD28-2.0 | 5700 | 59.0 | 416 | 37.6 |

CD274-APC and CD25-PE AVG

| | Single Cell/ Lymphocytes/ CD4, SSC-A subset \| Count | Single Cell/ Lymphocytes/ CD4, SSC-A subset \| Freq. of Parent (%) | Single Cell/ Lymphocytes/ CD4, SSC-A subset \| Median (Comp-APC-A) | Single Cell/ Lymphocytes/ CD4, SSC-A subset \| Median (Comp-PE-A) | Single Cell/ Lymphocytes/ CD4, SSC-A subset/CD274, SSC-A subset \| Freq. of Parent (%) | Single Cell/ Lymphocytes/ CD4, SSC-A subset/CD25, SSC-A subset \| Freq. of Parent (%) | Single Cell/ Lymphocytes/ CD4, SSC-A subset/CD25, SSC-A subset \| Median (Comp-PE-A) |
|---|---|---|---|---|---|---|---|
| 072418-4FF PBMC - CD3-0 CD28-0 | 3189 | 47.6 | 117 | 190 | 5.19 | 6.81 | 2329 |
| 072418-4FF PBMC - CD3-3 CD28-0.02 | 3133 | 70.2 | 1312 | 19417 | 94.1 | 97.1 | 19973 |
| 072418-4FF PBMC - CD3-6 CD28-2.0 | 2909 | 68.7 | 1185 | 19166 | 92.4 | 96.2 | 19855 |
| 072518-92M TBX3400 - CD3-0 CD28-0 | 5499 | 57.2 | 148 | 229 | 14.4 | 3.60 | 2472 |
| 072518-92M TBX3400 - CD3-3 CD28-0.02 | 3766 | 63.0 | 1249 | 25793 | 84.5 | 85.2 | 30355 |
| 072518-92M TBX3400 - CD3-6 CD28-2.0 | 3258 | 55.2 | 1202 | 17895 | 84.5 | 82.3 | 22779 |

FIG. 3A

COMPOSITIONS AND METHODS FOR TREATING T CELL EXHAUSTION

CROSS-REFERENCE TO RELATED APPLICATIONS

This application is a national phase of International Application No. PCT/US2020/032702, filed May 13, 2020, which claims the benefit of priority to U.S. Provisional Patent Application No. 62/847,701, filed May 14, 2019, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jun. 30, 2020, is named 106417-0587 Sequence Listing.txt and is 22 KB in size.

BACKGROUND OF THE INVENTION

T cell exhaustion is a state of T cell dysfunction that arises during chronic infections and cancer. It is characterized by poor T cell effector function, sustained expression of inhibitory receptors, and a transcriptional state that is distinct from functional effector and memory T cells. Exhaustion negatively affects the immune system's ability to control infection and tumor growth and metastasis.

After an acute infection, naive antigen-specific CD8$^+$ T cells become activated, proliferate, acquire effector functions, and differentiate into effector CD8$^+$ T cells. Following clearance of the acute infection, most effector CD8$^+$ T cells will undergo apoptosis; however, about 5-10% differentiate into memory CD8$^+$ T cells. During chronic infection, severe defects in CD8$^+$ T cell responses can develop, and antigen-specific CD8$^+$ T cells often fail to differentiate into memory CD8$^+$ T cells. Loss of effector function (e.g., T-cell exhaustion) occurs in a hierarchical manner, with CD8$^+$ T cells progressively losing functions, such as IL-2 production proliferative capacity, and cytotoxicity. Chronic antigen exposure to tumor antigens produces a similar exhaustion phenomenon in CD8$^+$ T cells that recognize tumor antigens expressed by cancer cells.

T cell exhaustion can also occur during acute viral infections as well. For example, in certain instances of acute respiratory infections (ARIs), CD8$^+$ T cells often exhibit diminished production of cytokines and cytotoxic molecules and exhibit similar patterns of gene expression to that observed in exhausted T cells during chronic infection. In this context, the tendency of CD8$^+$ T cells to have significantly reduced functionality in the context of respiratory virus infection is called T cell impairment.

Currently, there is an unmet need for compositions and methods that can decrease and/or reverse T cell exhaustion/impairment and restore effector function after or during a chronic infection and for the treatment of cancer.

SUMMARY OF THE INVENTION

Provided herein are compositions and methods for treating T cell exhaustion, or T cell impairment, in a subject, by administering a PTD-MYC fusion protein (e.g., an HIV TAT-MYC fusion protein) or immune cells isolated from a donor subject and treated with a PTD-MYC fusion protein. In some embodiments, the T cell exhaustion is associated with a chronic microbial infection (e.g. bacterial, viral, fungal, protozoan or parasitic) or cancer. In some embodiments, the T cell exhaustion, or T cell impairment, is associated with an acute viral infection (e.g. acute respiratory virus infections, such as infection by influenza virus, respiratory syncytial virus (RSV), pneumonia virus, respiratory vaccinia virus, parainfluenza virus, respiratory adenoviruses, severe acute respiratory syndrome corona virus (SARS-CoV), Middle East respiratory syndrome corona virus (MFRS-CoV), or human metapneumovirus (HMPV)). In some embodiments, administration of the PTD-MYC fusion protein or PTD-MYC modified immune cells reduces T cell exhaustion, or T cell impairment, in the subject. For example, in some embodiments, administration of the PTD-MYC fusion protein or PTD-MYC modified immune cells reduces the number of exhausted cells (e.g., exhausted T cells) in the subject. In some embodiments, administration of the PTD-MYC fusion protein or PTD-MYC modified immune cells increases the immune response against a pathogen associated with a chronic microbial infection. In some embodiments, administration of the PTD-MYC fusion protein or PTD-MYC modified immune cells alleviate one or more symptoms of a chronic microbial infection.

Provided herein, in certain embodiments, are methods for treating T cell exhaustion, or T cell impairment, in a subject in need thereof, comprising administering an effective amount of one or more modified immune cells to the subject, wherein the one or more modified immune cells comprises a MYC fusion protein comprising (i) a protein transduction domain; and (ii) a MYC polypeptide sequence. In some embodiments, the subject is identified as having altered expression of at least one immune cell marker of T cell exhaustion, or T cell impairment, compared to expression of the at least one immune cell marker in a healthy control. In some embodiments, the immune cell marker is an immune checkpoint protein. In some embodiments, the subject has a microbial infection. In some embodiments, the microbial infection is a chronic microbial infection. In some embodiments, the microbial infection is a bacterial infection, a viral infection, a fungal infection, a protozoan infection, or parasitic infection. In some embodiments, the microbial infection is caused by a pathogen selected from the group consisting of *Mycobacterium tuberculosis, Mycobacterium leprae, Mycobacterium bovis, Helicobacter pylori, Staphylococcus aureus, Salmonella Typhi, Treponema pallidum, Escherichia coli, Hemophilus influenza, Pseudomonas aeruginosa, Plasmodium falciparum, Plasmodium vivax, Plasmodium ovale, Plasmodium malariae,* Human Immunodeficiency Virus (HIV), Herpesviruses, Herpes Simplex Virus (HSV), Hepatitis B Virus (HBV), Hepatitis C Virus (HCV), Measles Virus, Papovaviruses, Varicella-Zoster Virus, T-Cell Leukemia Viruses, Adenoviruses, Parvoviruses, Epstein-Barr Virus, Enterovirus, Mouse Hepatitis Virus (MHV), Cytomegalovirus (CMV), Papillomaviruses and Lymphocytic Choriomeningitis Virus (LCMV). In some embodiments, the T cell exhaustion, or T cell impairment, is associated with an acute viral infection, such as an acute respiratory virus infection, such as infection by influenza virus, respiratory syncytial virus (RSV), pneumonia virus, respiratory vaccinia virus, parainfluenza virus, respiratory adenoviruses, severe acute respiratory syndrome corona virus (SARS-CoV), Middle East respiratory syndrome corona virus (MERS-CoV), or human metapneumovirus (HMPV)). In some embodiments, the subject has cancer. In some embodiments, the cancer is melanoma. In some embodiments, the melanoma is relapsed refractory melanoma. In some embodiments, the one or more modified immune cells are derived from immune cells isolated from the subject. In some embodiments, the immune cells isolated from the subject are obtained from the peripheral blood of the subject. In some embodiments, the immune cells isolated from the subject are obtained from the lymph node, spleen, or tumor of the subject. In some embodiments, the one or more modified immune cells are prepared by contacting the immune cells in vitro with the MYC fusion protein. In some embodiments, the one or more modified immune cells are prepared by contacting a population of peripheral blood mononuclear cells from the subject in vitro with the MYC fusion protein. In some embodiments, the methods further comprise expanding the modified immune cells in vitro prior to and/or following contacting the modified immune cells with the MYC fusion protein. In some embodiments, the protein transduction domain sequence is a TAT protein transduction domain sequence. In some embodiments, the MYC fusion protein comprises SEQ ID NO: 1. In some embodiments, the MYC fusion protein translocates to the nucleus of one or more modified immune cells. In some embodiments, the MYC fusion protein exhibits a biological activity of MYC. In some embodiments, the altered expression comprises an increase in the cell surface expression of one or more immune cell receptors. In some embodiments, the one or more cell surface receptors comprises PD-1, LAG-3, CD160, 2B4, or any combination thereof. In some embodiments, the one or more modified immune cells are administered intravenously, intraperitoneally, subcutaneously, intramuscularly, or intratumorally. In some embodiments, the subject is a human or a non-human animal. In some embodiments, the one or more modified immune cells comprises one or more T cells. In some embodiments, the one or more modified immune cells comprises one or more CD8$^+$ T cells. In some embodiments, the one or more modified immune cells comprises one or more exhausted immune cells. In some embodiments, the one or more modified immune cells comprises one or more exhausted T cells. In some embodiments, the one or more modified immune cells comprises one or more exhausted CD8$^+$ T cells.

Provided herein, in certain embodiments, are methods for treating a chronic microbial infection in a subject in need thereof, comprising administering an effective amount of one or more modified immune cells to the subject, wherein the one or more modified immune cells comprise a MYC fusion protein comprising (i) a protein transduction domain; and (ii) a MYC polypeptide sequence. In some embodiments, the subject is identified as having altered expression of at least one immune cell marker of T cell exhaustion, or T cell impairment, compared to expression of the at least one immune cell marker in a healthy control. In some embodiments, the immune cell marker is an immune checkpoint protein. In some embodiments, the microbial infection is a bacterial infection, a viral infection, a fungal infection, a protozoan infection, or parasitic infection. In some embodiments, the microbial infection is caused by a pathogen selected from the group consisting of *Mycobacterium tuberculosis, Mycobacterium leprae, Mycobacterium bovis, Helicobacter pylori, Staphylococcus aureus, Salmonella Typhi, Treponema pallidum, Escherichia coli, Hemophilus influenza, Pseudomonas aeruginosa, Plasmodium falciparum, Plasmodium vivax, Plasmodium ovale, Plasmodium malariae,* Human Immunodeficiency Virus (HIV), Herpesviruses, Herpes Simplex Virus (HSV), Hepatitis B Virus (HBV), Hepatitis C Virus (HCV), Measles Virus, Papovaviruses, Varicella-Zoster Virus, T-Cell Leukemia Viruses, Adenoviruses, Parvoviruses, Epstein-Ban Virus, Enterovirus, Mouse Hepatitis Virus (MHV), Cytomegalovirus (CMV), Papillomaviruses and Lymphocytic Choriomeningitis Virus (LCMV). In some embodiments, the subject was previously vaccinated against the pathogen. In some embodiments, the one or more modified immune cells are derived from immune cells isolated from the subject. In some embodiments, the immune cells isolated from the subject are obtained from the peripheral blood of the subject. In some embodiments, the immune cells isolated from the subject are obtained from the lymph node, spleen, or tumor of the subject. In some embodiments, the one or more modified immune cells are prepared by contacting the T cells in vitro with the MYC fusion protein. In some embodiments, the methods further comprise expanding the cells in vitro prior to and/or following contacting the cells with the MYC fusion protein. In some embodiments, the protein transduction domain sequence is a TAT protein transduction domain sequence. In some embodiments, the MYC fusion protein comprises SEQ ID NO: 1. In some embodiments, the MYC fusion protein translocates to the nucleus of one or more immune cells in the immune cell population. In some embodiments, the MYC fusion protein exhibits a biological activity of MYC. In some embodiments, the altered expression comprises an increase in the cell surface expression of one or more immune cell receptors. In some embodiments, the one or more cell surface receptors comprises PD-1, LAG-3, CD160, 2B4, or any combination thereof. In some embodiments, the one or more modified immune cells are administered intravenously, intraperitoneally, subcutaneously, intramuscularly, or intratumorally. In some embodiments, the subject is a human or a non-human animal. In some embodiments, the one or more modified immune cells comprises one or more T cells. In some embodiments, the one or more modified immune cells comprises one or more CD8$^+$ T cells. In some embodiments, the one or more modified immune cells comprises one or more exhausted immune cells. In some embodiments, the one or more modified immune cells comprises one or more exhausted T cells. In some embodiments, the one or more modified immune cells comprises one or more exhausted CD8$^+$ T cells.

Provided herein, in certain embodiments, are methods for treating an acute respiratory infection associated with T cell impairment in a subject in need thereof, comprising administering an effective amount of one or more modified immune cells to the subject, wherein the one or more modified immune cells comprise a MYC fusion protein comprising (i) a protein transduction domain; and (ii) a MYC polypeptide sequence. In some embodiments, the subject is identified as having altered expression of at least one immune cell marker of T cell exhaustion, or T cell impairment, compared to expression of the at least one immune cell marker in a healthy control. In some embodiments, the immune cell marker is an immune checkpoint protein. In some embodiments, the acute respiratory virus infection is caused by a pathogen selected from the group consisting of influenza virus, respiratory syncytial virus (RSV), pneumonia virus, respiratory vaccinia virus, parainfluenza virus, respiratory adenoviruses, severe acute respiratory syndrome corona virus (SARS-CoV), Middle East respiratory syndrome corona virus (MERS-CoV), and human metapneumovirus (HMPV)). In some embodiments, the subject was previously vaccinated against the pathogen. In some embodiments, the one or more modified immune cells are derived from immune cells isolated from the subject. In some embodiments, the immune cells isolated from the subject are obtained from the peripheral blood of the subject. In some embodiments, the immune cells isolated from the subject are obtained from the lymph node, spleen, or tumor of the subject. In some embodiments, the one or more modified immune cells are prepared by contacting the T cells in vitro with the MYC fusion protein. In some embodiments, the methods further comprise expanding the cells in vitro prior to and/or following contacting the cells with the MYC fusion protein. In some embodiments, the protein transduction domain sequence is a TAT protein transduction domain sequence. In some embodiments, the MYC fusion protein comprises SEQ ID NO: 1. In some embodiments, the MYC fusion protein translocates to the nucleus of one or more immune cells in the immune cell population. In some embodiments, the MYC fusion protein exhibits a biological activity of MYC. In some embodiments, the altered expression comprises an increase in the cell surface expression of one or more immune cell receptors. In some embodiments, the one or more cell surface receptors comprises PD-1, LAG-3, CD160, 2B4, or any combination thereof. In some embodiments, the one or more modified immune cells are administered intravenously, intraperitoneally, subcutaneously, intramuscularly, or intratumorally. In some embodiments, the subject is a human or a non-human animal. In some embodiments, the one or more modified immune cells comprises one or more T cells. In some embodiments, the one or more modified immune cells comprises one or more CD8$^+$ T cells. In some embodiments, the one or more modified immune cells comprises one or more exhausted immune cells. In some embodiments, the one or more modified immune cells comprises one or more exhausted T cells. In some embodiments, the one or more modified immune cells comprises one or more exhausted CD8$^+$ T cells.

Also provided herein, in certain embodiments, are uses of one or more modified immune cells for treating T cell exhaustion, or T cell impairment, in a subject in need thereof, wherein the one or more modified immune cells comprise a MYC fusion protein comprising (i) a protein transduction domain; and (ii) a MYC polypeptide sequence.

Also provided herein, in certain embodiments, are uses of one or more modified immune cells for treating a chronic microbial infection or acute respiratory virus infection associated with T cell exhaustion, or T cell impairment, in a subject in need thereof, wherein the one or more modified immune cells comprise a MYC fusion protein comprising (i) a protein transduction domain; and (ii) a MYC polypeptide sequence.

BRIEF DESCRIPTION OF THE DRAWINGS

FIGS. 3A-3E illustrate the level of CD274 (PD-L1) expression (FIGS. 3A-3C) and CD25 (IL2RA) expression (FIGS. 3A and 3D-3E) in populations of immune cells isolated from donor subjects, following pre-treatment with the PTD-MYC fusion polypeptide or vehicle control, and activation under various conditions.

FIG. 4A shows flow cytometry histograms of PBMC samples labeled with fluorescent antibodies to CD279 that were collected from two relapsed refractory melanoma patients (101 and 103) before and after a one-hour treatment with Tat-MYC protein (TBX-3400). FIG. 4B is a set of flow cytometry diagrams showing intracellular staining results for two different tags on the Tat-MYC protein (His or V5) in PBMCs isolated from a patient enrolled in a relapsed refractory melanoma trial. The patient's PBMCs were either left untreated (left panels) or treated with Tat-MYC (TBX-4000) for one hour (right panels). FIG. 4C is a set of charts showing the results of a flow cytometry analysis of PBMC samples treated with Tat-MYC (TBX-4000) for one hour in a closed system. Samples were analyzed for intracellular levels of Tat-MYC by using fluorescent antibodies that bind to two different Tat-MYC tags (the His Tag and the V5 tag). The left-hand chart shows the results of cells stained for the protein on day zero (0 d) and on the following day (1 d). In the right-hand chart, Tat-MYC treated cells (TBX-3400; (+)) and untreated cells (PBMC-No Treatment; (−)) from the patient were activated with antibodies to CD3 and CD28. The expression levels of T cell activation marker, CD25, and the checkpoint markers, CD279 and CD152, were analyzed by flow cytometry.

DETAILED DESCRIPTION OF THE INVENTION

Figures 1A, 1B:
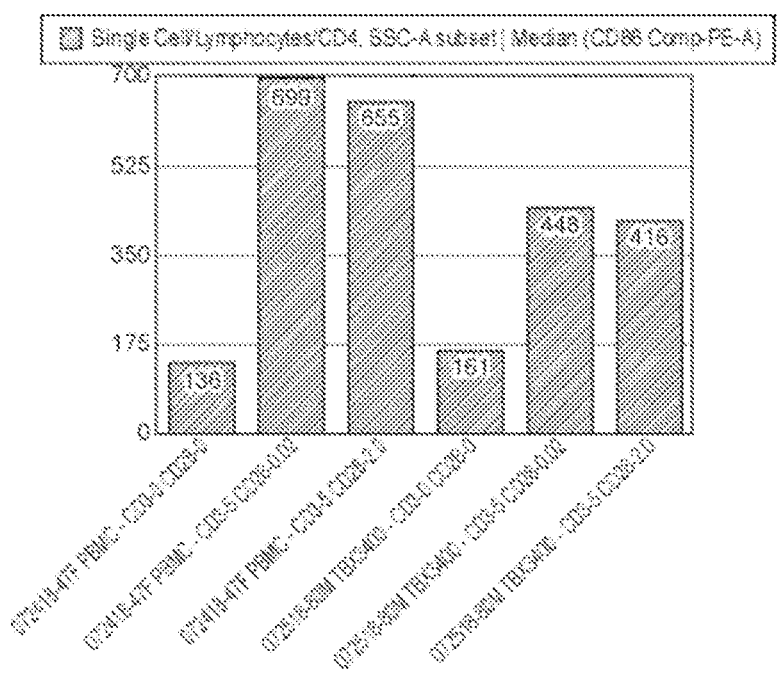
FIGS. 1A-1C illustrate the level of CD86 expression in populations of immune cells isolated from donor subjects, following pre-treatment with the PTD-MYC fusion polypeptide or vehicle control, and activation under various conditions.

It is to be appreciated that certain aspects, modes, embodiments, variations, and features of the present technology are described below in various levels of detail in order to provide a substantial understanding of the present technology.

I. Definitions

The definitions of certain terms as used in this specification are provided below. Unless defined otherwise, all technical and scientific terms used herein generally have the same meaning as commonly understood by one of ordinary skill in the art to which this present technology belongs.

As used herein, the singular forms "a", "an", and "the" are intended to include the plural forms as well, unless the context clearly indicates otherwise.

As used herein, the term "about" means that a value can vary +/−20%, +/−15%, +/−10% or +/−5% and remain within the scope of the present disclosure. For example, "a concentration of about 200 IU/mL" encompasses a concentration between 160 IU/mL and 240 IU/mL.

As used herein, the term "administration" of an agent to a subject includes any route of introducing or delivering the agent to a subject to perform its intended function. Administration can be carried out by any suitable route, including intravenously, intramuscularly, intraperitoneally, or subcutaneously. Administration includes self-administration and the administration by another.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "effective amount" or "therapeutically effective amount" refers to a quantity of an agent sufficient to achieve a desired therapeutic effect. In the context of therapeutic applications, the amount of a therapeutic protein administered to the subject can depend on the type and severity of the infection and on the characteristics of the individual, such as general health, age, sex, body weight and tolerance to drugs. It can also depend on the degree, severity and type of disease. The skilled artisan will be able to determine appropriate dosages depending on these and other factors.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

As used herein the term immune cell refers to any cell that plays a role in the immune response. Immune cells are of hematopoietic origin, and include lymphocytes, such as B cells and T cells; natural killer cells; myeloid cells, such as monocytes, macrophages, dendritic cells, eosinophils, neutrophils, mast cells, basophils, and granulocytes.

The term "lymphocyte" refers to all immature, mature, undifferentiated and differentiated white lymphocyte populations including tissue specific and specialized varieties. It encompasses, by way of non-limiting example, B cells, T cells, NKT cells, and NK cells. In some embodiments, lymphocytes include all B cell lineages including pre-B cells, progenitor B cells, early pro-B cells, late pro-B cells, large pre-B cells, small pre-B cells, immature B cells, mature B cells, plasma B cells, memory B cells, B-1 cells, and B-2 cell populations.

As used herein, the term T-cell includes naïve T cells, CD4+ T cells, CD8+ T cells, memory T cells, activated T cells, exhausted T cells, tolerant T cells, chimeric T cells, and antigen-specific T cells.

The term "B cell" or "B cells" refers to, by way of non-limiting example, a pre-B cell, progenitor B cell, early pro-B cell, late pro-B cell, large pre-B cell, small pre-B cell, immature B cell, mature B cell, naïve B cells, plasma B cells, activated B cells, exhausted B cells, tolerant B cells, chimeric B cells, antigen-specific B cells, memory B cell, B-1 cell, and B-2 cell populations.

As used herein "adoptive cell therapeutic composition" refers to any composition comprising cells suitable for adoptive cell transfer. In exemplary embodiments, the adoptive cell therapeutic composition comprises a cell type selected from a group consisting of a tumor infiltrating lymphocyte (TIL), TCR (i.e. heterologous T-cell receptor) modified lymphocytes and CAR (i.e. chimeric antigen receptor) modified lymphocytes. In another embodiment, the adoptive cell therapeutic composition comprises a cell type selected from a group consisting of T-cells, exhausted T-cells, CD8+ cells, CD4+ cells, NK-cells, delta-gamma T-cells, and regulatory T-cells. In another embodiment, TILs, T-cells, CD8+ cells, CD4+ cells, NK-cells, delta-gamma T-cells, regulatory T-cells or peripheral blood mononuclear cells form the adoptive cell therapeutic composition. In one embodiment, the adoptive cell therapeutic composition comprises T cells. In one embodiment, the adoptive cell therapeutic composition may be a composition comprising one or more primary immune cells isolated from a donor subject which have been contacted with a PTD-MYC fusion protein, comprising (i) a protein transduction domain; (ii) a MYC polypeptide sequence.

As used herein, the term "exhausted immune cell," "exhausted T cell," and "exhausted B cell" refer to dysfunctional T cells and B cells, and does not encompass anergic immune cells, anergic T cells, or anergic B cells. Exhausted immune cells, exhausted T cells, and exhausted B cells are characterized by progressive loss of effector functions during chronic infections or cancer with some functions that are exhausted early (e.g., IL-2, cytotoxicity, and proliferation), whereas others (e.g., IFN-γ) persist longer. Anergic immune cells, anergic T cells, or anergic B cells can arise when immune cells receive initial TCR signals in the absence of co-stimulation, leading to a state of hyporesponsiveness. Notably, anergy seems to be a state of nonresponsiveness that is molecularly distinct from exhaustion (Wherry, J. E. *Nature Immunology* 12:492-499 (2011); Wherry, J. E. et al. *Immunity* 27:670-684 (2007)).

The terms "MYC" and "MYC gene" are synonyms. They refer to a nucleic acid sequence that encodes a MYC polypeptide. A MYC gene comprises a nucleotide sequence of at least 120 nucleotides that is at least 60% to 100% identical or homologous, e.g., at least 60, 65%, 70%, 75%, 80%, 85%, 86%, 87%, 88%, 90%, 91%, 92%, 94%, 95%, 96%, 97%, 98%, or any other percent from about 70% to about 100% identical to sequences of NCBI Accession Number NM-002467. In some embodiments, the MYC gene is a proto-oncogene. In certain instances, a MYC gene is found on chromosome 8, at 8q24.21. In certain instances, a MYC gene begins at 128,816,862 bp from pter and ends at 128,822,856 bp from pter. In certain instances, a MYC gene is about 6 kb. In certain instances, a MYC gene encodes at least eight separate mRNA sequences—5 alternatively spliced variants and 3 unspliced variants.

The terms "MYC protein," "MYC polypeptide," and "MYC sequence" are synonyms and refer to the polymer of amino acid residues disclosed in NCBI Accession Number UniProtKB/Swiss-Prot:P01106.1 (MYC isoform 1) or NP_002458.2 (UniProtKB/Swiss-Prot:P01106.2; MYC isoform 2), and functional homologs, analogs or fragments thereof. The sequence of or UniProtKB/Swiss-Prot: P01106.1 is:

```
                                          (SEQ ID NO: 2)
mplnvsftnrnydldydsvqpyfycdeeenfyqqqqqselqppa psediwkkfellptpplspsrrsglcspsyvavtpfslrgdndg gggsfstadqlemvtellggdmvnqsficdpddetfikniiiqd cmwsgfsaaaklvseklasyqaarkdsgspnparghsvcstssl ylqdlsaaasecidpsvvfpyplndssspkscasqdssafspss dsllsstesspqgspeplvlheetppttssdseeeqedeeeidv vsvekrqapgkrsesgspsagghskpphsplvlkrchvsthqhn yaappstrkdypaakrvkldsvrvlrqisnnrkctsprssdtee nvkrrthnvlerqrrnelkrsffalrdqipelennekapkvvil kkatayilsvqaeeqkliseedllrkrreqlkhkleqlrnsca
```

The sequence of NP_002458.2 (UniProtKB/Swiss-Prot: P01106.2) is:

```
                                         (SEQ ID NO: 11)
mdffrvvenqqppatmplnysftnrnydldydsvqpyfycdeee nfyqqqqselqppapsediwkkfellptpplspsrrsglcsps yvavtpfslrgdndggggsfstadqlemytellggdmvnqsfic dpddetfikniiiqdcmwsgfsaaaklvseklasyqaarkdsgs pnparghsvcstsslylqdlsaaasecidpsyvfpyplndsssp kscasqdssafspssdsllsstesspqgspeplvlheetpptts sdseeeqedeeeidyysvekrqapgkrsesgspsagghskpphs plylkrchysthqhnyaappstrkdypaakrvkldsvrvlrqis nnrkctsprssdteenykrrthnvlerqrrnelkrsffalrdqi pelennekapkvvilkkatayilsvqaeeqkliseedllrkrre qlkhkleqlrnsca
```

In some embodiments, the MYC polypeptide is a complete MYC polypeptide sequence. In some embodiments, the MYC polypeptide is a partial MYC polypeptide sequence. In some embodiments, the MYC polypeptide comprises at least 400 consecutive amino acids of SEQ ID NO: 2 OR 11. In some embodiments, the MYC polypeptide comprises at least 400 consecutive amino acids of SEQ ID NO: 2 OR 11 and retains at least one MYC activity. In some embodiments, the MYC polypeptide comprises at least 400, at least 410, at least 420, at least 430, or at least 450 consecutive amino acids of SEQ ID NO: 2 OR 11. In some embodiments, the MYC polypeptide comprises at least 400, at least 410, at least 420, at least 430, or at least 450 consecutive amino acids of SEQ ID NO: 2 OR 11 and retains at least one MYC activity. In some embodiments, the MYC polypeptide is c-MYC. In some embodiments, the MYC polypeptide sequence comprises the sequence shown below:

```
                                          (SEQ ID NO: 3)
MDFFRVVENQQPPATMPLNVSFTNRNYDLDYDSVQPYFYCDEEE

NFYQQQQQSELQPPAPSEDIWKKFELLPTPPLSPSRRSGLCSPS

YVAVTPFSLRGDNDGGGGSFSTADQLEMVTELLGGDMVNQSFIC

DPDDETFIKNIIIQDCMWSGFSAAAKLVSEKLASYQAARKDSGS

PNPARGHSVCSTSSLYLQDLSAAASECIDPSVVFPYPLNDSSSP

KSCASQDSSAFSPSSDSLLSSTESSPQGSPEPLVLREETPPTTS

SDSEEEQEDEEELDVVSVEKRQAPGKRSESGSPSAGGHSKPPHS

PLVLKRCHVSTHQHNYAAPPSTRKDYPAAKRVKLDSVRVLRQIS

NNRKCTSPRSSDTEENVKRRTHNVLERQRRNELKRSFFALRDQI

PELENNEKAPKVVILKKATAYILSVQAEEQKLISEEDLLRKRRE

QLKIAKLEQLR.
```

In some embodiments, the MYC polypeptide sequence comprises the sequence shown below:

```
                                          (SEQ ID NO: 4)
PLNVSFTNRNYDLDYDSVQPYFYCDEEENFYQQQQQSELQPPAP

SEDIWKKFELLPTPPLSPSRRSGLCSPSYVAVTPFSLRGDNDGG

GGSFSTADQLEMVTELLGGDMVNQSFICDPDDETFIKNIIIQDC

MWSGFSAAAKLVSEKLASYQAARKDSGSPNPARGHSVCSTSSLY

LQDLSAAASECIDPSVVFPYPLNDSSSPKSCASQDSSAFSPSSD

SLLSSTESSPQGSPEPLVLREETPPTTSSDSEEEQEDEEEIDVV
```

```
SVEKRQAPGKRSESGSPSAGGHSKPPHSPLVLKRCHVSTHQHNY

AAPPSTRKDYPAAKRVKLDSVRVLRQISNNRKCTSPRSSDTEEN

VKRRTHNVLERQRRNELKRSFFALRDQIPELENNEKAPKVVILK

KATAYILSVQAEEQKLISEEDLLRKRREQLKIAKLEQLR.
```

In some embodiments, a MYC polypeptide comprises an amino acid sequence that is at least 40% to 100% identical, e.g., at least 40%, 45%, 50%, 55%, 60%, 65%, 70%, 75%, 80%, 81%, 82%, 83%, 84%, 85%, 86%, 87%, 88%, 90%, 91%, 92%, 94%, 95%, 96%, 97%, 98%, 99%, or any other percent from about 40% to about 100% identical to the sequence of NCBI Accession Number NP002458.2 or UniProtKB/Swiss-Prot Accession Number P01106.1. In some embodiments, MYC polypeptide refers to a polymer of 439 amino acids, a MYC polypeptide that has not undergone any post-translational modifications. In some embodiments, MYC polypeptide refers to a polymer of 439 amino acids that has undergone post-translational modifications. In some embodiments, the MYC polypeptide is 48,804 kDa. In some embodiments, the MYC polypeptide contains a basic Helix-Loop-Helix Leucine Zipper (bHLH/LZ) domain. In some embodiments, the bHLH/LZ domain comprises the sequence of: ELKRSFFALRDQIPELENNEKAPKVVILK-KATAYILSVQAEEQKLISEEDLLRKRREQLKH KLEQLR (SEQ ID NO: 5). In some embodiments, the MYC polypeptide is a transcription factor (e.g., Transcription Factor 64). In some embodiments, the MYC polypeptide contains an E-box DNA binding domain. In some embodiments, the MYC polypeptide binds to a sequence comprising CACGTG. In some embodiments, the MYC polypeptide promotes one or more of cell survival and/or proliferation. In some embodiments, a MYC polypeptide includes one or more of those described above, and includes one or more post-translational modifications (e.g., acetylation). In some embodiments, the MYC polypeptides comprise one or more additional amino acid residues at the N-terminus or C-terminus of the polypeptide. In some embodiments, the MYC polypeptides are fusion proteins. In some embodiments, the MYC polypeptides are linked to one or more additional peptides at the N-terminus or C-terminus of the polypeptide.

Proteins suitable for use in the methods described herein also includes functional variants, including proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. Where amino acid substitutions are made, the substitutions can be conservative amino acid substitutions. Among the common, naturally occurring amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al (1992), *Proc. Natl Acad. Sci. USA,* 89:10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

The phrases "E-box sequence" and "enhancer box sequence" are used interchangeably herein and mean the nucleotide sequence CANNTG, wherein N is any nucleotide. In certain instances, the E-box sequence comprises CACGTG. In certain instances, the basic helix-loop-helix domain of a transcription factor encoded by MYC binds to the E-box sequence. In certain instances, the E-box sequence is located upstream of a gene (e.g., p21, Bcl-2, or ornithine decarboxylase). In certain instances, the MYC polypeptide contains an E-box DNA binding domain. In certain instances, the E-box DNA binding domain comprises the sequence of KRRTHNVLERQRRN (SEQ ID NO: 6). In certain instances, the binding of the transcription factor encoded by MYC to the E-box sequence, allows RNA polymerase to transcribe the gene downstream of the E-box sequence.

The term "MYC activity" or "MYC biological activity" or "biologically active MYC" or "biological activity of MYC" includes one or more of enhancing or inducing cell survival, cell proliferation, and/or antibody production. By way of example and not by way of limitation, MYC activity includes enhancement of expansion of anti-CD3 and anti-CD28 activated T-cells and/or increased proliferation of long-term self-renewing hematopoietic stem cells. MYC activity also includes entry into the nucleus of a cell, binding to a nucleic acid sequence (e.g., binding an E-box sequence), and/or inducing expression of MYC target genes.

The terms "patient," "subject," "individual," and the like are used interchangeably herein, and refer to an animal, typically a mammal. In one embodiment, the patient, subject, or individual is a mammal. In one embodiment, the patient, subject or individual is a human. In some embodiments the patient, subject or individual is an animal, such as, but not limited to, domesticated animals, such as equine, bovine, murine, ovine, canine, and feline.

The terms "protein transduction domain (PTD)" or "transporter peptide sequence" (also known as cell permeable proteins (CPP) or membrane translocating sequences (MTS)) are used interchangeably herein to refer to small peptides that are able to ferry much larger molecules into cells independent of classical endocytosis. In some embodiments, a nuclear localization signal can be found within the protein transduction domain, which mediates further translocation of the molecules into the cell nucleus.

The terms "treating" or "treatment" as used herein covers the treatment of a disease in a subject, such as a human, and includes: (i) inhibiting a disease, i.e., arresting its development; (ii) relieving a disease, i.e., causing regression of the disease; (iii) slowing progression of the disease; and/or (iv) inhibiting, relieving, or slowing progression of one or more symptoms of the disease. With respect to a tumor, "treating" or "treatment" also encompasses regression of a tumor, slowing tumor growth, inhibiting metastasis of a tumor, inhibiting relapse or recurrent cancer and/or maintaining remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment can be a continuous prolonged treatment for a chronic disease or a single, or few time administrations for the treatment of an acute condition.

The term "therapeutic" as used herein means a treatment and/or prophylaxis. A therapeutic effect is obtained by suppression, remission, or eradication of a disease state.

II. Overview

The present disclosure relates to the treatment of T cell exhaustion, or T cell impairment, in a subject using a MYC fusion protein comprising a protein transduction domain and a MYC polypeptide sequence. In certain embodiments, the T cell exhaustion, or T cell impairment, results from chronic conditions, such as chronic viral infection or cancer. In certain embodiments, the T cell exhaustion, or T cell impairment, results from acute respiratory viral infection. In some embodiments, T cell exhaustion, or T cell impairment, occurs following vaccination. In some embodiments, T cell exhaustion, or T cell impairment, occurs during active infection in an individual that has been previously vaccinated.

The present disclosure is based, at least in part, on the discovery, that contacting T cells isolated from a donor subject with a PTD-MYC fusion polypeptide containing a MYC polypeptide and a protein transduction domain (PTD), such as the HIV TAT protein transduction domain, advantageously results in a decrease in the expression of cell surface immune checkpoint proteins, including but not limited to, Programmed cell death protein 1 (PD-1), also known as CD279 (cluster of differentiation 279), or cytotoxic T-lymphocyte-associated protein 4 (CTLA-4), also known as CD152 (cluster of differentiation 152). PD-1 and CTLA-4 are inhibitory receptors that promote T cell exhaustion during chronic microbial infection and in cancer. Additional co-receptors, such as LAG-3, CD244 (2B4), CD160, TIM-3 also contribute to this effect. Blocking receptor signaling from these receptors, for example, by using inhibitory antibodies that target and block these receptors, has been shown to substantially decrease T cell dysfunction and increase cytotoxic T cell responses. It is found herein that similar effects can be achieved using a MYC fusion protein to downregulate these receptors, thus decreasing the negative signaling pathways that result in T cell exhaustion, or T cell impairment. In some embodiments, a MYC fusion protein provided herein is employed to reverse immune cell exhaustion/impairment. In some embodiments, a MYC fusion protein provided herein is employed to prevent or ameliorate immune cell exhaustion/impairment.

In one aspect, the present disclosure provides a method for treating or preventing T cell exhaustion, or T cell impairment, in a subject in need thereof, wherein the method comprises administering an effective amount of one or more modified immune cells (e.g., T cells, such as, for example, $CD8^+$ T cells) to the subject, wherein the one or more modified immune cells comprise a PTD-MYC fusion protein comprising (i) a protein transduction domain; and (ii) a MYC polypeptide sequence. In some embodiments, the subject is identified as having altered expression of at least one or more immune cell markers associated with T cell exhaustion, or T cell impairment, compared to that observed in a healthy control. In some embodiments, the one or more modified immune cells are derived from immune cells isolated from the subject. In some embodiments, immune cells are isolated from an allogenic donor. The immune cells can be obtained from the peripheral blood, lymph node, spleen, or a tumor. In some embodiments, the immune cells comprise one or more lymphocytes. In some embodiments, the one or more lymphocytes comprise a T cell, a B cell, an NK cell, or any combination thereof. In some embodiments, the one or more lymphocytes comprise a T cell. In some embodiments, the one or more lymphocytes comprise a $CD8^+$ T cell. In some embodiments, the one or more lymphocytes comprise one or more exhausted lymphocytes from the subject (e.g. one or more exhausted T cells, for example, one or more exhausted CD8+ T cells). In some embodiments, the one or more lymphocytes do not comprise exhausted lymphocytes but are isolated from a subject having one or more exhausted lymphocytes.

In some embodiments, the one or more modified immune cells may be prepared by contacting a population of immune cells (e.g., $CD8^+$ T cells) in vitro with the MYC fusion protein following isolation from the subject. In some embodiments, the method may further include expanding the immune cells in vitro prior to contacting the cells with the MYC fusion protein. In some embodiments, the method may further include expanding the immune cells in vitro following contacting the primary immune cells with the MYC fusion protein.

In another aspect, the present disclosure provides a method for treating or preventing T cell exhaustion, or T cell impairment, in a subject in need thereof, wherein the method comprises administering an effective amount of a MYC fusion protein comprising (i) a protein transduction domain; and (ii) a MYC polypeptide sequence. In some embodiments, the subject is identified as having altered expression of at least one or more immune cell markers associated with T cell exhaustion, or T cell impairment, compared to that observed in a healthy control.

In some embodiments, the MYC fusion protein or one or more modified immune cells comprising the MYC fusion protein may be administered by any appropriate method, e.g., intravenously, intraperitoneally, subcutaneously, intramuscularly, or intratumorally.

Exemplary PTD-MYC fusion proteins for use in the methods are provided herein. The PTD-MYC fusion proteins provided are able to enter immune cells (e.g., T cell) and translocate to the nucleus, where the fusion protein can activate one or more MYC-responsive genes. In some embodiments, the protein transduction domain sequence of the MYC fusion protein comprises a TAT protein transduction domain sequence. In some embodiments, the MYC polypeptide portion of the MYC fusion protein comprises the amino sequence set forth in SEQ ID NO: 2 or 11. In some embodiments, the PTD-MYC fusion protein comprises the amino sequence set forth in SEQ ID NO: 1.

In some embodiments, subjects for treatment with a MYC fusion protein provided herein or a modified immune cell comprising a MYC fusion protein provided herein exhibit increased expression one or more immune cell markers, wherein increased or sustained expression of the immune cell marker is associated with T cell exhaustion, or T cell impairment, compared to that observed in a healthy control (e.g., a non-exhausted T cell). In some embodiments, the one or more immune cell markers that are increased is an immune checkpoint protein. In some embodiments, the one or more immune cell markers that are increased is selected from the group consisting of PD1, LAG3, CD160, 2B4 (CD244) and a combination of any two or more thereof.

In some embodiments, the one or more immune cell markers that are increased is selected from the group consisting of PD-1, CTLA-4, LAG-3, CD160, 2B4, IL-7ra, IL-15ra, KLRG-1, TIM-3, Eomes and a combination of any two or more thereof.

In some embodiments, the one or more immune cell markers that are increased in an exhausted T cell is selected from the group consisting of CD244, PDCD1, CTLA4, GP49B, PTGER4, CD160, LAG3, IL7R, IL15RA, HAVCR2, PTGER2, CD7, TNFRSF9, GLYCOP, VCAM1, TNFSF6, ITM2A, MOX2, ITGAV, CD9, CCL3, CXCR4, CCL4, CCRL2, SMAD1, RGS16, GPR56, TANK, DUSP1, GPR65, PTPN13, PRKWNK, IL6ST, ITPR5, JAK3, MAP3K1, SH2D2A, SOCS3, ACTN1, ISG20, G1P2, ICSBP1, SERPINA, TCRG-V4, TCRB-V1, PBX3, EOMES, ATF1, AHR, EGR2, HFATC1, ZFP91, HIST1H2, BCL2, CASP3, GAS2, CKS2, CAR2, PLSCR1, SLC12A2, ART3, GPD2, NDUFA5, CYP4V3, ENTPD1, P2RX4, C76628, SFRS7, MTV43, C79248, PENK1, COCH, NR4A2, A43010, IER5, SEPTIN, RCN, WBP5, PBEF1, PPM1B, DDIT4, KDT1, TRIM47, HRB, RNF11, NRIP1, TUBB2, SPP1, KLK6, LY75, SCL29A1, BUB1, NDFIP1, SPRED2, CBX4, and a combination of any two or more thereof.

In some embodiments, treatment with a MYC fusion protein provided herein or a modified immune cell comprising a MYC fusion protein results in a decrease of at least one or more immune cell markers selected from the group consisting of CD244, PDCD1, CTLA4, GP49B, PTGER4, CD160, LAG3, IL7R, IL15RA, HAVCR2, PTGER2, CD7, TNFRSF9, GLYCOP, VCAM1, TNFSF6, ITM2A, MOX2, ITGAV, CD9, CCL3, CXCR4, CCL4, CCRL2, SMAD1, RGS16, GPR56, TANK, DUSP1, GPR65, PTPN13, PRKWNK, IL6ST, ITPR5, JAK3, MAP3K1, SH2D2A, SOCS3, ACTN1, ISG20, G1P2, ICSBP1, SERPINA, TCRG-V4, TCRB-V1, PBX3, EOMES, ATF1, AHR, EGR2, HFATC1, ZFP91, HIST1H2, BCL2, CASP3, GAS2, CKS2, CAR2, PLSCR1, SLC12A2, ART3, GPD2, NDUFA5, CYP4V3, ENTPD1, P2RX4, C76628, SFRS7, MTV43, C79248, PENK1, COCH, NR4A2, A43010, IER5, SEPTIN, RCN, WBP5, PBEF1, PPM1B, DDIT4, KDT1, TRIM47, HRB, RNF11, NRIP1, TUBB2, SPP1, KLK6, LY75, SCL29A1, BUB1, NDFIP1, SPRED2, CBX4, and a combination of any two or more thereof, compared to that observed prior to administration.

In some embodiments, subjects for treatment with a MYC fusion protein provided herein or a modified immune cell comprising a MYC fusion protein provided herein exhibit decreased expression one or more immune cell markers, where decreased expression of the immune cell marker is associated with T cell exhaustion, or T cell impairment, compared to that observed in a healthy control (e.g., a non-exhausted T cell). In some embodiments, the one or more immune cell markers that is decreased is selected from the group consisting of IGSF10, SELPL, H2-Q8, FCGR2B, CD3D, ITGB2, ITGA1, ITGA4, KLRK1, SEMA4A, IL18R1, KLRD1, LY6C, KLRC1, EDG6, ITGB7, ITGAX, KLRG1, CKLFSF7, LSP1, CCR5, CCR2, H2-K1, H2-D1, H2-Q10, H2-Q7, SIAT10, LGALS10, RAC2, PIK3CD, ILK, MAP3K8, ARHGEF1, S100A6, STK38, LCK, ARHGAP1, S100A4, RASA3, JAK1, S100A1, HCPH, DGKA, PTK9L, IL18RAP, MAP1LC3, ACTB, IFNGR, TPP2, LYZS, CAPN2, CTSD, USP3, PRSS19, MUS, BZW1, RORA, KLF2, RUNX1, HOD, KLF3, SATB1, BNIP3L, ANXA2, ANXA6, ANXA1, VAMP3, SNX5, SNX10, CDC37, CDKN2D, PAK2, CDC34, HMGCS1, RPN2, NDUFB6, PDHA1, ARL6IP5, PSMD13, FXYD5, ARL2BP, UBE1X, APOBEC, KCTD10, SSR3, UGCG, MGC68, GARS, SDHA, HSPA8, RRM2, ATP5L, PFKP, HBB-B1, HBB-A1, TCEB2, EIF3S8, RPS16, EIF2S1, SFPQ, RPL10A, RPL36, EEF2, RPS7, PIGT, RPL27A, PPGB, TAGLN2, HINT1, LEF1, LSP1, TOB1, SDCBP, SEP15, MTVR2, GABARAPL2, PLD3, ETS1, DSTN, LBR, GOLPH2, WDR1, PLP2, NME2, KCNAB2, DIAP1, TXNDC5, SMFN, STARD10, CLIC1, TMSB10, IAP, GM2A, ATP6V0B, DNAJD1, SUPT4H, PTPRC, CRIP1, EMP1, PLAC8, and a combination of any two or more thereof.

In some embodiments, treatment with a MYC fusion protein provided herein or a modified immune cell comprising a MYC fusion protein results in an increase of at least one or more immune cell markers selected from the group consisting of IGSF10, SELPL, H2-Q8, FCGR2B, CD3D, ITGB2, ITGA1, ITGA4, KLRK1, SEMA4A, IL18R1, KLRD1, LY6C, KLRC1, EDG6, ITGB7, ITGAX, KLRG1, CKLFSF7, LSP1, CCR5, CCR2, H2-K1, H2-D1, H2-Q10, H2-Q7, SIAT10, LGALS10, RAC2, PIK3CD, ILK, MAP3K8, ARHGEF1, S100A6, STK38, LCK, ARHGAP1, S100A4, RASA3, JAK1, S100A1, HCPH, DGKA, PTK9L, IL18RAP, MAP1LC3, ACTB, IFNGR, TPP2, LYZS, CAPN2, CTSD, USP3, PRSS19, MUS, BZW1, RORA, KLF2, RUNX1, HOD, KLF3, SATB1, BNIP3L, ANXA2, ANXA6, ANXA1, VAMP3, SNX5, SNX10, CDC37, CDKN2D, PAK2, CDC34, HMGCS1, RPN2, NDUFB6, PDHA1, ARL6IP5, PSMD13, FXYD5, ARL2BP, UBE1X, APOBEC, KCTD10, SSR3, UGCG, MGC68, GARS, SDHA, HSPA8, RRM2, ATP5L, PFKP, HBB-B1, HBB-A1, TCEB2, EIF3S8, RPS16, EIF2S1, SFPQ, RPL10A, RPL36, EEF2, RPS7, PIGT, RPL27A, PPGB, TAGLN2, HINT1, LEF1, LSP1, TOB1, SDCBP, SEP15, MTVR2, GABARAPL2, PLD3, ETS1, DSTN, LBR, GOLPH2, WDR1, PLP2, NME2, KCNAB2, DIAP1, TXNDC5, SMFN, STARD10, CLIC1, TMSB10, IAP, GM2A, ATP6V0B, DNAJD1, SUPT4H, PTPRC, CRIP1, EMP1, PLAC8, and a combination of any two or more thereof, compared to that observed prior to administration. In some embodiments, treatment with a MYC fusion protein provided herein or a modified immune cell comprising a MYC fusion protein results in an increase in cytokine production in the subject compared to that observed prior to administration. In some embodiments, treatment with a MYC fusion protein provided herein or a modified immune cell comprising a MYC fusion protein results in an increase in production of IL-2, TNF, Granzyme B, and/or IFN gamma in the subject compared to that observed prior to administration.

In another aspect, the present disclosure provides a method for treating a chronic microbial infection in a subject in need thereof, wherein the method comprises administering an effective amount of one or more modified immune cells (e.g., CD8$^+$ T cells) to the subject, wherein the one or more modified immune cells comprise a PTD-MYC fusion protein comprising (i) a protein transduction domain; and (ii) a MYC polypeptide sequence. In another aspect, the present disclosure provides a method for treating a chronic microbial infection in a subject in need thereof, wherein the method comprises administering an effective amount a PTD-MYC fusion protein comprising (i) a protein transduction domain; and (ii) a MYC polypeptide sequence. In some embodiments, the subject is identified as having altered expression of at least one or more immune cell markers associated with T cell exhaustion, or T cell impairment, compared to that observed in a healthy control. In some embodiments, the one or more modified immune cells are derived from immune cells isolated from the subject.

In some embodiments, the chronic microbial infection is a bacterial infection, a viral infection, a fungal infection, a protozoan infection, or parasitic infection. In some embodiments, the chronic microbial infection is chronic or latent form of a viral infection. In some embodiments, the chronic microbial infection is caused by a pathogen selected from the group consisting of *Mycobacterium tuberculosis, Mycobacterium leprae, Mycobacterium bovis, Helicobacter pylori, Staphylococcus aureus, Salmonella Typhi, Treponema pallidum, Escherichia coli, Hemophilus influenza, Pseudomonas aeruginosa, Plasmodium falciparum, Plasmodium vivax, Plasmodium ovale, Plasmodium malariae*, Human Immunodeficiency Virus (HIV), Herpesviruses, Herpes Simplex Virus (HSV), Hepatitis B Virus (HBV), Hepatitis C Virus (HCV), Measles Virus, Papovaviruses, Varicella-Zoster Virus, T-Cell Leukemia Viruses, Adenoviruses, Parvoviruses, Epstein-Barr Virus, Enterovirus, Mouse Hepatitis Virus (MHV), Cytomegalovirus (CMV), Papillomaviruses and Lymphocytic Choriomeningitis Virus (LCMV). In some embodiments, the chronic microbial infection is an antibiotic resistant or antiviral resistant infection (e.g., antibiotic resistant tuberculosis (TB), Methicillin-resistant *Staphylococcus aureus* (MRSA), Enterovirus 68, Nipah virus, Middle East respiratory syndrome (MERS)).

In another aspect, the present disclosure provides a method for treating an acute respiratory viral infection in a subject in need thereof, wherein the method comprises administering an effective amount of one or more modified immune cells (e.g., CD8$^+$ T cells) to the subject, wherein the one or more modified immune cells comprise a PTD-MYC fusion protein comprising (i) a protein transduction domain; and (ii) a MYC polypeptide sequence. In another aspect, the present disclosure provides a method for treating an acute respiratory viral infection in a subject in need thereof, wherein the method comprises administering an effective amount a PTD-MYC fusion protein comprising (i) a protein transduction domain; and (ii) a MYC polypeptide sequence. In some embodiments, the subject is identified as having altered expression of at least one or more immune cell markers associated with T cell exhaustion, or T cell impairment, compared to that observed in a healthy control. In some embodiments, the one or more modified immune cells are derived from immune cells isolated from the subject.

In some embodiments, the subject has previously been administered one or more vaccines against the pathogen. In some embodiments, the subject exhibits T cell exhaustion, or T cell impairment, following vaccination against the pathogen. In some embodiments, the subject exhibits T cell exhaustion, or T cell impairment, during pathogenic infection, where the subject has been previously vaccinated against the pathogen.

In some embodiments, the subject having a chronic microbial infection, or acute respiratory viral infection, exhibits increased expression one or more immune cell markers, where increased expression of the immune cell marker is associated with T cell exhaustion, or T cell impairment, compared to that observed in a healthy control (e.g., a non-exhausted T cell). In some embodiments, the one or more immune cell markers that are increased is an immune checkpoint protein. In some embodiments, the one or more immune cell markers that are increased is selected from the group consisting of PD1, LAG3, CD160, 2B4 (CD244) and a combination of any two or more thereof. In some embodiments, the one or more immune cell markers that are increased is selected from the group consisting of PD-1, CTLA-4, LAG-3, CD160, 2B4, IL-7ra, IL-15ra, KLRG-1, TIM-3, Eomes and a combination of any two or more thereof. In some embodiments, the one or more immune cell markers that are increased is selected from the group consisting of CD244, PDCD1, CTLA4, GP49B, PTGER4, CD160, LAG3, IL7R, IL15RA, HAVCR2, PTGER2, CD7, TNFRSF9, GLYCOP, VCAM1, TNFSF6, ITM2A, MOX2, ITGAV, CD9, CCL3, CXCR4, CCL4, CCRL2, SMAD1, RGS16, GPR56, TANK, DUSP1, GPR65, PTPN13, PRKWNK, IL6ST, ITPR5, JAK3, MAP3K1, SH2D2A, SOCS3, ACTN1, ISG20, G1P2, ICSBP1, SERPINA, TCRG-V4, TCRB-V1, PBX3, EOMES, ATF1, AHR, EGR2, HFATC1, ZFP91, HIST1H2, BCL2, CASP3, GAS2, CKS2, CAR2, PLSCR1, SLC12A2, ART3, GPD2, NDUFA5, CYP4V3, ENTPD1, P2RX4, C76628, SFRS7, MTV43, C79248, PENK1, COCH, NR4A2, A43010, IER5, SEPTIN, RCN, WBP5, PBEF1, PPM1B, DDIT4, KDT1, TRIM47, HRB, RNF11, NRIP1, TUBB2, SPP1, KLK6, LY75, SCL29A1, BUB1, NDFIP1, SPRED2, CBX4, and a combination of any two or more thereof.

In some embodiments, the subject having a chronic microbial infection, or acute respiratory viral infection, exhibits decreased expression one or more immune cell markers, where decreased expression of the immune cell marker is associated with T cell exhaustion, or T cell impairment, compared to that observed in a healthy control (e.g., a non-exhausted T cell). In some embodiments, the one or more immune cell markers that is decreased is selected from the group consisting of IGSF10, SELPL, H2-Q8, FCGR2B, CD3D, ITGB2, ITGA1, ITGA4, KLRK1, SEMA4A, IL18R1, KLRD1, LY6C, KLRC1, EDG6, ITGB7, ITGAX, KLRG1, CKLFSF7, LSP1, CCR5, CCR2, H2-K1, H2-D1, H2-Q10, H2-Q7, SIAT10, LGALS10, RAC2, PIK3CD, ILK, MAP3K8, ARHGEF1, S100A6, STK38, LCK, ARHGAP1, S100A4, RASA3, JAK1, S100A1, HCPH, DGKA, PTK9L, IL18RAP, MAP1LC3, ACTB, IFNGR, TPP2, LYZS, CAPN2, CTSD, USP3, PRSS19, MUS, BZW1, RORA, KLF2, RUNX1, HOD, KLF3, SATB1, BNIP3L, ANXA2, ANXA6, ANXA1, VAMP3, SNX5, SNX10, CDC37, CDKN2D, PAK2, CDC34, HMGCS1, RPN2, NDUFB6, PDHA1, ARL6IP5, PSMD13, FXYD5, ARL2BP, UBE1X, APOBEC, KCTD10, SSR3, UGCG, MGC68, GARS, SDHA, HSPA8, RRM2, ATP5L, PFKP, HBB-B1, HBB-A1, TCEB2, EIF3S8, RPS16, EIF2S1, SFPQ, RPL10A, RPL36, EEF2, RPS7, PIGT, RPL27A, PPGB, TAGLN2, HINT1, LEF1, LSP1, TOB1, SDCBP, SEP15, MTVR2, GABARAPL2, PLD3, ETS1, DSTN, LBR, GOLPH2, WDR1, PLP2, NME2, KCNAB2, DIAP1, TXNDC5, SMFN, STARD10, CLIC1, TMSB10, IAP, GM2A, ATP6V0B, DNAJD1, SUPT4H, PTPRC, CRIP1, EMP1, PLAC8, and a combination of any two or more thereof.

In any of the methods provided here, subjects for treatment with a MYC fusion protein provided herein or a modified immune cell comprising a MYC fusion protein provided herein can be a human or a non-human animal.

In another aspect, the present disclosure provides a method for treating a cancer in a subject in need thereof, wherein the method comprises administering an effective amount of one or more modified immune cells (e.g., $CD8^+$ T cells) to the subject, wherein the one or more modified immune cells comprise a PTD-MYC fusion protein comprising (i) a protein transduction domain; and (ii) a MYC polypeptide sequence, where the subject is identified as having altered expression of at least one or more immune cell markers associated with T cell exhaustion, or T cell impairment, compared to that observed in a healthy control. In another aspect, the present disclosure provides a method for treating a cancer in a subject in need thereof, wherein the method comprises administering an effective amount a PTD-MYC fusion protein comprising (i) a protein transduction domain; and (ii) a MYC polypeptide sequence, where the subject is identified as having altered expression of at least one or more immune cell markers associated with T cell exhaustion, or T cell impairment, compared to that observed in a healthy control. In some embodiments, the one or more modified immune cells are derived from immune cells isolated from the subject. In some embodiments, the cancer is a metastatic cancer. In some embodiments, the cancer is a carcinoma, adenoma, adenocarcinoma, blastoma, sarcoma, or lymphoma. In some embodiments, the cancer is a basal cell carcinoma, biliary tract cancer, bladder cancer, breast cancer, cervical cancer, choriocarcinoma, CNS cancer, colon cancer, colorectal cancer, connective tissue cancer, cancer of the digestive system, endometrial cancer, esophageal cancer, eye cancer, gastric cancer, glial cell tumor, head and neck cancer, hepatoma, hepatic carcinoma, Hodgkin's lymphoma, Non-Hodgkin's lymphoma, intra-epithelial neoplasm, kidney cancer, larynx cancer, liver cancer, small-cell lung cancer, non-small cell lung cancer, melanoma, myeloma, neuroblastoma, oral cavity cancer, ovarian cancer, pancreatic cancer, prostate cancer, rectal cancer, renal cancer, cancer of the respiratory system, retinoblastoma, rhabdomyosarcoma, salivary gland carcinoma, squamous cell cancer, stomach cancer, testicular cancer, thyroid cancer, uterine cancer, cancer of the urinary system, or a vulvar cancer. In some embodiments, the immune cells are obtained from a donor subject having solid tumor where the subject is identified as having altered expression of at least one or more immune cell markers associated with T cell exhaustion, or T cell impairment, compared to that observed in a healthy control. In some embodiments, the solid tumor is a metastatic tumor.

III. Methods of Obtaining and Preparing Immune Cells for Transfer

Immune cells for use in the methods provided herein can be obtained using any suitable method known in the art. In some embodiments, the immune cells are primary immune cells. In some embodiments, the immune cells are lymphocytes, such as T and B cells. In some embodiments, the immune cells are natural killer (NK) cells. In some embodiments, the immune cells are a mixture of lymphocytes and NK cells. In some embodiments, the immune cells are obtained from the peripheral blood of a donor subject. In some embodiments, the immune cells are peripheral blood mononuclear cells (PBMC). In some embodiments, the immune cells are obtained from the spleen or lymph nodes of a donor subject.

In some embodiments, the immune cells are modified following isolation from a donor. For example, in some embodiments, the immune cells are CAR T cells.

In some embodiments, the immune cells are obtained from a subject that has a chronic infection. In some embodiments, the chronic infection is a bacterial infection, a viral infection, a fungal infection, a protozoan infection, or parasitic infection.

In some embodiments, the immune cells are obtained from a subject that has a tumor. In some embodiments, the immune cells are T cells that have infiltrated a tumor (e.g., tumor infiltrating lymphocytes). In some embodiments, the T cells are removed during surgery of a tumor. For example, in some embodiments, the T cells are isolated after removal of tumor tissue by biopsy.

In some embodiments, the T cells are isolated from a sample containing a population of cells, such as a blood, lymph, spleen or tissue biopsy sample. T cells can be isolated from a population of cells by any means known in the art. In one embodiment, the methods comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells can include, but are not limited to, any one or more of mechanically dissociating (e.g., mincing) the tumor, enzymatically dissociating (e.g., digesting) the tumor, and/or aspiration (e.g., as with a needle).

The bulk population of T cells obtained from a tumor sample can comprise any suitable type of T cell. Preferably, the bulk population of T cells obtained from a tumor sample comprises tumor infiltrating lymphocytes (TILs).

The population of immune cells can be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). The mammals can be non-human primates, e.g., of the order Primates, Ceboids, or Simoids (monkeys) or of the order Anthropoids (humans and apes). In some embodiments, the mammal can be a mammal of the order Rodentia, such as mice and hamsters. Preferably, the mammal is a non-human primate or a human. An exemplary mammal is a human.

In some embodiments, the subject to receive the immune cells is also the donor of the immune cells (i.e., autologous ACT). In some embodiments, the subject to receive the immune cells is different than the donor of the tumor sample (i.e. allogenic ACT).

T cells can be obtained from a number of sources, including peripheral blood mononuclear cells, bone marrow, lymph node tissue, spleen tissue, and tumors. In certain embodiments, T cells can be obtained from a unit of blood collected from a subject using any number of techniques known to the skilled artisan, such as Ficoll separation. In one embodiment, cells from the circulating blood of an individual are obtained by apheresis or leukopheresis. The apheresis product typically contains lymphocytes, including T cells, monocytes, granulocytes, B cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and can lack magnesium or can lack many if not all divalent cations. Initial activation steps in the absence of calcium lead to magnified activation. As those of ordinary skill in the art would readily appreciate, a washing step can be accomplished by methods known to those in the art, such as by using a semi-automated "flow-through" centrifuge (for example, the Cobe 2991 cell processor) according to the manufacturer's instructions. After washing, the cells can be resuspended in a variety of biocompatible buffers, such as, for example, Ca-free, Mg-free PBS. Alternatively, the undesirable components of the apheresis sample can be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times can be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. In one embodiment, the method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) can be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology can be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it can be desirable to significantly decrease the volume in which beads and cells are mixed together (i.e., increase the concentration of cells), to ensure maximum contact of cells and beads. For example, in one embodiment, a concentration of 2 billion cells/mL is used. In one embodiment, a concentration of 1 billion cells/mL is used. In a further embodiment, greater than 100 million cells/mL is used. In a further embodiment, a concentration of cells of 10, 15, 20, 25, 30, 35, 40, 45, or 50 million cells/mL is used. In yet another embodiment, a concentration of cells from 75, 80, 85, 90, 95, or 100 million cells/mL is used. In further embodiments, concentrations of 125 or 150 million cells/mL can be used. Using high concentrations can result in increased cell yield, cell activation, and cell expansion. Further, use of high cell concentrations allows more efficient capture of cells that can weakly express target antigens of interest, such as CD28− negative T cells, or from samples where there are many tumor cells present (e.g., leukemic blood, tumor tissue). Such populations of cells can have therapeutic value and would be desirable to obtain. For example, using high concentration of cells allows more efficient selection of CD8+ T cells that normally have weaker CD28 expression.

In a related embodiment, it can be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/mL. In other embodiments, the concentration used can be from about $1\times10^5$/ml to $1\times10^6$/mL, and any integer value in between. Thus, the concentration used may be from about $1\times10^5$/mL, about $1.1\times10^5$/mL, about $1.2\times10^5$/mL, about $1.3\times10^5$/mL, about $1.4\times10^5$/mL, about $1.5\times10^5$/mL, about $1.6\times10^5$/mL, about $1.7\times10^5$/mL, about $1.8\times10^5$/mL, about $1.9\times10^5$/mL, about $2\times10^5$/mL, about $2.2\times10^5$/mL, about $2.4\times10^5$/mL, about $2.6\times10^5$/mL, about $2.8\times10^5$/mL, about $3\times10^5$/mL, about $3.2\times10^5$/mL, about $3.4\times10^5$/mL, about $3.6\times10^5$/mL, about $3.8\times10^5$/mL, about $4\times10^5$/mL, about $4.2\times10^5$/mL, about $4.4\times10^5$/mL, about $4.6\times10^5$/mL, about $4.8\times10^5$/mL, about $5\times10^5$/mL, about $5.5\times10^5$/mL, about $6\times10^5$/mL, about $6.5\times10^5$/mL, about $7\times10^5$/mL, about $7.5\times10^5$/mL, about $8\times10^5$/mL, about $8.5\times10^5$/mL, about $9\times10^5$/mL, about $9.5\times10^5$/mL, about $1\times10^6$/mL, or any integer value in between.

T cells can also be frozen. The freeze and subsequent thaw step can provide a more uniform product by removing granulocytes and to some extent monocytes in the cell population. After a washing step to remove plasma and platelets, the cells can be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing can be used as well as uncontrolled freezing immediately at −20° C. or in liquid nitrogen.

In some embodiments, cells are directly labeled with an epitope-specific reagent for isolation and/or enrichment by flow cytometry followed by characterization of cell phenotypes. In some embodiments, immune cells are isolated by contacting the immune cell specific antibodies. Sorting of any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In one embodiment, the method further comprises expanding the numbers of T cells in the enriched cell population. Such methods are described in U.S. Pat. No. 8,637,307 and is hereby incorporated by reference in its entirety. The T cells can be expanded before or after treatment of the cells with the PTD-MYC fusion polypeptide. The numbers of T cells can be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000-fold, or most preferably at least about 100,000-fold. The numbers of T cells can be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells can be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal can be used in soluble form. Ligands can be attached to the surface of a cell, to an Engineered Multivalent Signaling Platform (EMSP), or immobilized on a surface. In a one embodiment both primary and secondary agents are co-immobilized on a surface, for example a bead or a cell. In one embodiment, the molecule providing the primary activation signal can be a CD3 ligand, and the co-stimulatory molecule can be a CD28 ligand or 4-1BB ligand. In some embodiments, the cells are expanded by stimulation with one or more antigens, such as a melanoma tumor antigen or antigens derived from the patient's tumor.

In some embodiments, the isolated immune cells are immediately treated with the PTD-MYC fusion polypeptide following isolation. In other embodiments, the isolated immune cells are stored in a suitable buffer and frozen prior to treatment with the PTD-MYC fusion polypeptide. In some embodiments, the isolated immune cells are immediately treated with the PTD-MYC fusion polypeptide following isolation and the treated cells are stored in a suitable buffer and frozen until needed for administration to the patient.

In certain embodiments, the isolated immune cells (e.g., a mixed population immune cells or isolated types, such as $CD8^+$ T cells) are contacted with a composition containing a PTD-MYC fusion polypeptide for a period of time sufficient to be taken up by the cells. In some embodiments, the immune cells are contacted with a composition containing a PTD-MYC fusion polypeptide for less than about 24 hours, less than about 23 hours, less than about 22 hours, less than about 21 hours, less than about 20 hours, less than about 19 hours, less than about 18 hours, less than about 17 hours, less than about 16 hours, less than about 15 hours, less than about 14 hours, less than about 13 hours, less than about 12 hours, less than about 11 hours, less than about 10 hours, less than about 9 hours, less than about 8 hours, less than about 7 hours, less than about 6 hours, less than about 5 hours, less than about 4 hours, less than about 3 hours, less than about 2 hours, or less than about 1 hour.

In certain embodiments, the immune cells are contacted with a composition containing a PTD-MYC fusion polypeptide for less than about 55 minutes, less than about 50 minutes, less than about 45 minutes, less than about 40 minutes, less than about 35 minutes, less than about 30 minutes, less than about 29 minutes, less than about 28 minutes, less than about 27 minutes, less than about 26 minutes, less than about 25 minutes, less than about 24 minutes, less than about 23 minutes, less than about 22 minutes, less than about 21 minutes, less than about 20 minutes, less than about 19 minutes, less than about 18 minutes, less than about 17 minutes, less than about 16 minutes, less than about 15 minutes, less than about 14 minutes, less than about 13 minutes, less than about 12 minutes, less than about 11 minutes, or less than about 10 minutes. In certain embodiments, the immune cells are contacted with a composition containing a PTD-MYC fusion polypeptide for about 1 hour.

In certain embodiments, the immune cells are contacted with a composition containing a PTD-MYC fusion polypeptide for 24 hours or longer. In certain embodiments, the immune cells are contacted with a composition containing a PTD-MYC fusion polypeptide for less than about 12 days, less than about 11 days, less than about 10 days, less than about 9 days, less than about 8 days, less than about 7 days, less than about 6 days, less than about 5 days, less than about 4 days, less than about 2 days, or less than about 1 day.

In certain embodiments that may be combined with any of the preceding embodiments, the cells are contacted with a PTD-MYC fusion polypeptide at a concentration of 0.5 μm/ml to 500 μg/ml. 0.5 μg/ml, at least 0.6 μm/ml, at least 0.7 μm/ml, at least 0.8 μm/ml, at least 0.9 μm/ml, at least 1 μg/ml, at least 2 μg/ml, at least 3 μg/ml, at least 4 μg/ml, at least 5 μg/ml, at least 6 μg/ml, at least 7 μg/ml, at least 8 μg/ml, at least 9 μg/ml, at least 10 μg/ml, at least 15 μg/ml, at least 20 μg/ml, at least 25 μg/ml, at least 30 μg/ml, at least 35 μg/ml, at least 40 μg/ml, at least 45 μg/ml, at least 50 μg/ml, at least 55 μg/ml, at least 60 μg/ml, at least 65 μg/ml, at least 70 μg/ml, at least 75 μg/ml, at least 80 μg/ml, at least 85 μg/ml, at least 90 μg/ml, at least 95 μg/ml, at least 100 μg/ml, at least 110 μg/ml, at least 120 μg/ml, at least 130 μg/ml, at least 140 μg/ml, at least 150 μg/ml, at least 160 μg/ml, at least 170 μg/ml, at least 180 μg/ml, at least 190 μg/ml, at least 200 μg/ml, at least 220 μg/ml, at least 240 μg/ml, at least 260 μg/ml, at least 280 μg/ml, at least 300

μg/ml, at least 320 μg/ml, at least 340 μg/ml, at least 360 μg/ml, at least 380 μg/ml, at least 400 μg/ml, at least 420 μg/ml, at least 440 μg/ml, at least 460 μg/ml, at least 480 μg/ml, at least 500 μg/ml.

In some embodiments, the immune cells that are contacted with a composition containing a PTD-MYC fusion polypeptide are T cells with genetically modified antigen receptors, including chimeric antigen receptor (CAR)-T cells. Various strategies can, for example, be employed to genetically modify T cells by altering the specificity of the T cell receptor (TCR), for example, by introducing new TCR α and β chains with selected peptide specificity (see, e.g., U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088, 379). Chimeric antigen receptors (CARs) can be used in order to generate immunoresponsive cells, such as T cells, specific for selected targets, such as malignant cells, with a wide variety of receptor chimera constructs having been described (see, e.g., U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Methods for the preparation of CART cells are known in the art and can be used in combination with the methods provided herein to generate modified CAR T cells comprising a Myc fusion polypeptide (e.g., PTD) as described herein. In some embodiments, PTD-MYC fusion polypeptide can improve the expansion of the CAR T cells prior to administration to the subject.

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

In some embodiments, the T cells expressing a desired CAR are selected through co-culture with γ-irradiated activating and propagating cells (AaPC), which co-express the antigen and co-stimulatory molecules. In some embodiments, the engineered CAR T-cells are expanded, for example by co-culture on AaPC in presence of soluble factors, such as IL-2 and IL-21. This expansion can for example be carried out so as to provide memory CAR+ T cells. In this way, CAR T cells can be provided that have specific cytotoxic activity against antigen-bearing cells (optionally in conjunction with production of desired chemokines such as interferon-γ).

In some embodiments, the CAR T-cells are contacted with a PTD-MYC fusion polypeptide provided herein in vitro to generation a modified CAR T cells for the treatment of a disease or condition associated with T cell exhaustion or T cell impairment (e.g., a chronic viral infection, cancer, or acute respiratory viral infection). The modified CAR T cells can be administered according any suitable method, including the methods for administration of the PTD-MYC fusion polypeptide-modified immune cells as described above.

IV. MYC Fusion Proteins

In some embodiments, the PTD-MYC fusion polypeptide comprises a protein transduction domain (PTD), a MYC polypeptide that promotes one or more of cell survival or proliferation, and optionally a protein tag domain, e.g., one or more amino acid sequences that facilitate purification of the fusion protein. In some embodiments, a cell contacted with MYC polypeptide exhibits increased survival time (e.g., as compared to an identical or similar cell of the same type that was not contacted with MYC), and/or increased proliferation (e.g., as compared to an identical or similar cell of the same type that was not contacted with MYC).

In some embodiments, the MYC fusion protein comprises (a) a protein transduction domain; and (b) a MYC polypeptide sequence. In some embodiments, the MYC fusion protein is a polypeptide of Formula (I):

protein transduction domain-MYC polypeptide sequence.

In some embodiments, a MYC fusion protein disclosed herein comprises (a) a protein transduction domain; (b) a MYC polypeptide sequence; and (c) one or more molecules that link the protein transduction domain and the MYC polypeptide sequence. In some embodiments, the MYC fusion protein is a polypeptide of Formula (II):

protein transduction domain-X-MYC polypeptide sequence, wherein —X— is a molecule that links the protein transduction domain and the MYC polypeptide sequence. In some embodiments, —X— is at least one amino acid.

In some embodiments, a MYC fusion protein disclosed herein comprises (a) a protein transduction domain; (b) MYC polypeptide sequence; (c) at least two protein tags; and (d) optionally linker(s). In some embodiments, the MYC fusion protein is a polypeptide of Formula (III-VI):

protein transduction domain-X-MYC polypeptide sequence-X-protein tag 1-X-protein tag 2 (Formula (III)), or protein transduction domain-MYC polypeptide sequence-X-protein tag 1-X-protein tag 2 (Formula (IV)), or protein transduction domain-MYC polypeptide sequence-protein tag 1-X-protein tag 2 (Formula (V)), or protein transduction domain-MYC polypeptide sequence-protein tag 1-protein tag 2 (Formula (VI)), wherein —X— is a linker. In some embodiments, —X— is one or more amino acids.

In some embodiments, a MYC fusion protein disclosed herein comprises (a) a protein transduction domain; (b) a MYC polypeptide sequence; (c) a 6-histidine tag; (d) a V5 epitope tag: and (e) optionally linker(s). In some embodiments, the MYC fusion protein is a polypeptide of Formula (VII-XIV):

protein transduction domain-X-MYC polypeptide sequence-X-6-histidine tag-X-V5 epitope tag (Formula (VII)), or protein transduction domain-MYC polypeptide sequence-X-6-histidine tag-X-V5 epitope tag (Formula (VIII)), or protein transduction domain-MYC polypeptide sequence-6-histidine tag-X-V5 epitope tag (Formula (IX)), or protein transduction domain-MYC polypeptide sequence-6-histidine tag-V5 epitope tag (Formula (X)), protein transduction domain-X-MYC polypeptide sequence-X-V5 epitope tag-X-6-histidine tag (Formula (XI)), or protein transduction domain-MYC polypeptide sequence-X-V5 epitope tag-X-6-histidine tag (Formula (XII)), or protein transduction domain-MYC polypeptide sequence-V5 epitope tag-X-6-histidine tag (Formula (XIII)), or
protein transduction domain-MYC polypeptide sequence-V5 epitope tag-6-histidine tag (Formula (XIV)),
wherein —X— is a linker. In some embodiments, —X— is one or more amino acids.

As noted above, in some embodiments, the MYC fusion protein comprises one or more linker sequences. The linker sequences can be employed to link the protein transduction domain, MYC polypeptide sequence, V5 epitope tag and/or 6-histidine tag of the fusion protein. In some embodiments, the linker comprises one or more amino acids. In some embodiments, the amino acid sequence of the linker comprises KGELNSKLE. In some embodiments, the linker comprises the amino acid sequence of RTG.

Protein Transduction Domain (PTD)

In some embodiments, the MYC fusion protein includes a protein transduction domain. Peptide transport provides an alternative for delivery of small molecules, proteins, or nucleic acids across the cell membrane to an intracellular compartment of a cell. One non-limiting example and well-characterized protein transduction domain (PTD) is a TAT-derived peptide. Frankel et al. (see, e.g., U.S. Pat. Nos. 5,804,604, 5,747,641, 5,674,980, 5,670,617, and 5,652,122) demonstrated transport of a cargo protein (β-galactosidase or horseradish peroxidase) into a cell by conjugating a peptide containing amino acids 48-57 of TAT to the cargo protein. In some embodiments, TAT comprises an amino acid sequence of MRKKRRQRRR (SEQ ID NO: 7).

Another non-limiting example of a PTD is penetratin. Penetratin can transport hydrophilic macromolecules across the cell membrane (Derossi et al., *Trends Cell Biol.*, 8:84-87 (1998) incorporated herein by reference in its entirety). Penetratin is a 16 amino acid peptide that corresponds to amino acids 43-58 of the homeodomain of Antennapedia, a *Drosophila* transcription factor which is internalized by cells in culture.

Yet another non-limiting example of a PTD is VP22. VP22, a tegument protein from Herpes simplex virus type 1 (HSV-1), has the ability to transport proteins and nucleic acids across a cell membrane (Elliot et al., *Cell* 88:223-233, 1997, incorporated herein by reference in its entirety). Residues 267-300 of VP22 are necessary but cannot be sufficient for transport. Because the region responsible for transport function has not been identified, the entire VP22 protein is commonly used to transport cargo proteins and nucleic acids across the cell membrane (Schwarze et al., *Trends Pharmacol Sci*, 21:45-48, 2000).

In some embodiments, the PTD-MYC fusion polypeptide includes a protein transduction domain. By way of example, but not by way of limitation, in some embodiments, the protein transduction domain comprises the protein transduction domain of one or more of TAT, penetratin, VP22, vpr, EPTD, R9, R15, VP16, and Antennapedia. In some embodiments, the protein transduction domain comprises the protein transduction domain of one or more of TAT, penetratin, VP22, vpr, and EPTD. In some embodiments, the protein transduction domain comprises the protein transduction domain of at least one of TAT, penetratin, VP22, vpr, EPTD, R9, R15, VP16, and Antennapedia. In some embodiments, the protein transduction domain comprises a synthetic protein transduction domain (e.g., polyarginine or PTD-5). In particular embodiments, the protein transduction domain comprises a TAT protein transduction domain. In some embodiments, the protein transduction domain is covalently linked to the MYC polypeptide. In some embodiments, the protein transduction domain is linked to the MYC polypeptide via a peptide bond. In some embodiments, the protein transduction domain is linked to the MYC polypeptide via a linker sequence. In some embodiments, the linker comprises a short amino acid sequence. By way of example, but not by way of limitation, in some embodiments, the linker sequence may be 1, 2, 3, 4, 5, 6, 7, 8, 9, or 10 amino acids in length.

The PTD-MYC fusion protein of the present technology can be arranged in any desired order. For example, in some embodiments, the MYC fusion protein can be arranged in order of a) the protein transduction domain linked in frame to the MYC polypeptide, b) the MYC polypeptide linked in frame to the V5 domain, and c) the V5 domain linked in frame to the 6-histidine epitope tag. In some embodiments, the MYC fusion protein has an order of components of a) the MYC polypeptide linked in frame to the protein transduction domain, b) the protein transduction domain linked in frame to the V5 domain, and c) the V5 domain linked in frame to the 6-histidine epitope tag. In some embodiments, additional amino acid sequences can be included between each of the sequences. In some embodiments, additional amino acids can be included at the start and/or end of the polypeptide sequences.

In some embodiments, the protein transduction domain is a TAT protein transduction domain. In some embodiments, the protein transduction domain is $TAT_{[48-57]}$. In some embodiments, the protein transduction domain is $TAT_{[57-48]}$.

Protein Tag Domains

In some embodiments, the MYC fusion protein comprises a protein tag domain that comprises one or more amino acid sequences that facilitate purification of the fusion protein. In some embodiments, the protein tag domain comprises one or more of a polyhistidine tag, and an epitope tag. By way of example, but not by way of limitation, exemplary tags include one or more of a V5, a histidine-tag (e.g., a 6-histidine tag), HA (hemagglutinin) tags, FLAG tag, CBP (calmodulin binding peptide), CYD (covalent yet dissociable NorpD peptide), Strepll, or HPC (heavy chain of protein C). In some embodiments, the protein tag domain comprises about 10 to about 20 amino acids in length. In some embodiments, the protein tag domain comprises 2 amino acids to 40 amino acids in length, for example 6-20 amino acids in length. In some embodiments, the protein tag domain comprises 2 amino acids, 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, 25 amino acids, 26 amino acids, 27 amino acids, 28 amino acids, 29 amino acids, 30 amino acids, 31 amino acids, 32 amino acids, 33 amino acids, 34 amino acids, 35 amino acids, 36 amino acids, 37 amino acids, 38 amino acids, 39 amino acids, or 40 amino acids. In some embodiments, two of the above listed tags (for example, V5 and the 6-histidine-tag) are used together to form the protein tag domain.

In some embodiments, the histidine tag is a 6-histidine tag. In some embodiments, the histidine tag comprises the sequence HHHHHH (SEQ ID NO: 8). In some embodiments, the MYC fusion protein disclosed herein comprises a V5 epitope tag. In some embodiments, the V5 tag comprises the amino acid sequence of: GKPIPNPLLGLDST (SEQ ID NO:9). In some embodiments, the V5 tag comprises the amino acid sequence of IPNPLLGLD (SEQ ID NO: 10).

The protein tags can be added to the fusion protein disclosed herein by any suitable method. By way of example, but not by way of limitation, in some embodiments, a TAT-MYC polypeptide sequence is cloned into an expression vector encoding one or more protein tags, e.g., a polyHis-tag and/or a V5 tag. In some embodiments, a polyhistidine tag and/or a V5 tag is added by PCR (i.e., the PCR primers comprise a polyhistidine sequence and/or V5 sequence).

Construction of PTD-MYC Fusion Polypeptides

PTD-MYC fusion polypeptides (e.g., TAT-MYC fusion polypeptide) disclosed herein can be constructed by methods well known in the art. By way of example, but not by way of limitation, a nucleotide sequence encoding a TAT-MYC fusion polypeptide can be generated by PCR. In some embodiments, a forward primer for a human MYC sequence comprises an in frame N-terminal 9-amino-acid sequence of the TAT protein transduction domain (e.g., RKKRRQRRR). In some embodiments, a reverse primer for a human MYC sequence is designed to remove the stop codon. In some embodiments, the PCR product is cloned into any suitable expression vector. In some embodiments, the expression vector comprises a polyhistidine tag and a V5 tag.

In some embodiments, a MYC fusion protein disclosed herein comprises (a) TAT, and (b) c-MYC. In some embodiments, a MYC fusion protein disclosed herein comprises (a) $TAT_{[48-57]}$, and (b) c-MYC. In some embodiments, a MYC fusion protein disclosed herein comprises (a) $TAT_{[57-48]}$, and (b) c-MYC.

In some embodiments, a MYC fusion protein disclosed herein comprises (a) TAT, (b) c-MYC, (c) linker(s), (d) V5 tag, and (e) 6-histidine tag. In some embodiments, a MYC fusion protein disclosed herein comprises (a) $TAT_{[48-57]}$, (b) c-MYC, (c) linker(s), (d) V5 tag, and (e) 6-histidine tag. In some embodiments, a MYC fusion protein disclosed herein comprises (a) $TAT_{[57-48]}$, (b) c-MYC, (c) linker(s), (d) V5 tag, and (e) 6-histidine tag.

In some embodiments, the PTD-MYC fusion polypeptide comprises SEQ ID NO: 1; in some embodiments, the PTD-MYC fusion polypeptide is SEQ ID NO: 1.

(SEQ ID NO: 1)
MRKKRRQRRRPLNVSFTNRNYDLDYDSVQPYFYCDEEEENFYQQQ

QQSELQPPAPSEDIWKKFELLPTPPLSPSRRSGLCSPSYVAVTP

FSLRGDNDGGGGSFSTADQLEMVTELLGGDMVNQSFICDPDDET

FIKNIIQDCMWSGFSAAAKLVSEKLASYQAARKDSGSPNPARG

HSVCSTSSLYLQDLSAAASECIDPSVVFPYPLNDSSSPKSCASQ

DSSAFSPSSDSLLSSTESSPQGSPEPLVLREETPPTTSSDSEEE

QEDEEEIDVVSVEKRQAPGKRSESGSPSAGGHSKPPHSPLVLKR

CHVSTHQHNYAAPPSTRKDYPAAKRVKLDSVRVLRQISNNRKCT

SPRSSDTEENVKRRTHNVLERQRRNELKRSFFALRDQIPELENN

EKAPKVVILKKATAYILSVQAEEQKLISEEDLLRKRREQLKEIK

LEQLRKGELNSKLEGKPIPNPLLGLDSTRTGHHHHHH.

The fusion protein can be modified during or after synthesis to include one or more functional groups. By way of example but not by way of limitation, the protein can be modified to include one or more of an acetyl, phosphate, acetate, amide, alkyl, and/or methyl group. This list is not intended to be exhaustive, and is exemplary only. In some embodiments, the protein includes at least one acetyl group.

A PTD-MYC fusion polypeptide can be generated by any suitable method known the art, e.g. by recombinant protein expression in a cell, such as a bacterial cell, an insect cell, or mammalian cell. In some embodiments, a PTD-MYC fusion polypeptide is recombinantly produced by microbial fermentation. In some embodiments microbial fermentation is performed in a fermentation volume of from about 1 to about 10,000 liters, for example, a fermentation volume of about 10 to about 1,000 liters. The fermentation can utilize any suitable microbial host cell and culture medium. In exemplary embodiments, E. coli is utilized as the microbial host cell. In alternative embodiments, other microorganisms can be used, e.g., S. cerevisiae, P. pastoris, Lactobacilli, Bacilli and Aspergilli. In an exemplary embodiment the microbial host cell is BL-21 Star™ E. coli strain (Invitrogen). In an exemplary embodiment the microbial host cell is BLR DE3 E. coli. strain.

In some embodiments the host cells are modified to provide tRNAs for rare codons, which are employed to overcome host microbial cell codon bias to improve translation of the expressed proteins. In exemplary embodiments, the host cells (e.g., E. coli) transformed with a plasmid, such as pRARE (CamR), which express tRNAs for AGG, AGA, AUA, CUA, CCC, GGA codons. Additional, suitable plasmids or constructs for providing tRNAs for particular codons are known in the art and can be employed in the methods provided.

Integrative or self-replicative vectors can be used for the purpose of introducing the PTD-MYC fusion polypeptide expression cassette into a host cell of choice. In an expression cassette, the coding sequence for the PTD-MYC fusion polypeptide is operably linked to promoter, such as an inducible promoter. Inducible promoters are promoters that initiate increased levels of transcription from DNA under their control in response to some change in culture conditions, e.g., the presence or absence of a nutrient or a change in temperature. In some embodiments, the nucleic acid encoding the PTD-MYC fusion polypeptide is codon optimized for bacterial expression.

Exemplary promoters that are recognized by a variety of potential host cells are well known. These promoters can be operably linked to PTD-MYC fusion polypeptide-encoding DNA by removing the promoter from the source DNA, if present, by restriction enzyme digestion and inserting the isolated promoter sequence into the vector. Promoters suitable for use with microbial hosts include, but are not limited to, the β-lactamase and lactose promoter systems (Chang et al. (1978) Nature, 275:617-624; Goeddel et al. (1979) Nature, 281: 544), alkaline phosphatase, a tryptophan (trp) promoter system (Goeddel (1980) Nucleic Acids Res. 8: 4057; EP 36,776), and hybrid promoters such as the tac promoter (deBoer et al. (1983) Proc. Natl. Acad. Sci. USA 80: 21-25). Any promoter for suitable for expression by the selected host cell can be used. Nucleotide sequences for suitable are published, thereby enabling a skilled worker operably to ligate them to DNA encoding PTD-MYC fusion polypeptide (see, e.g., Siebenlist et al. (1980) Cell 20: 269) using linkers or adaptors to supply any required restriction sites. In exemplary embodiments, promoters for use in bacterial systems can contain a Shine-Dalgarno (S.D.) sequence operably linked to the coding sequence. In some embodiments, the inducible promoter is the lacZ promoter, which is induced with Isopropyl β-D-1-thiogalactopyranoside (IPTG), as is well-known in the art. Promoters and expression cassettes can also be synthesized de novo using well known techniques for synthesizing DNA sequences of interest. In an exemplary embodiment, the expression vector for expression of the PTD-MYC fusion polypeptides herein is pET101/D-Topo (Invitrogen).

For expression of the PTD-MYC fusion polypeptides, the microbial host containing the expression vector encoding the PTD-MYC fusion polypeptide is typically grown to high density in a fermentation reactor. In some embodiments, the reactor has controlled feeds for glucose. In some embodiments, a fermenter inoculum is first cultured in medium supplemented with antibiotics (e.g., overnight culture). The fermenter inoculum is then used to inoculate the fermenter culture for expression of the protein. At an OD600 of at least about 15, usually at least about 20, at least 25, at least about 30 or higher, of the fermenter culture, expression of the recombinant protein is induced. In exemplary embodiments, where the inducible promoter is the lacZ promoter, IPTG is added to the fermentation medium to induce expression of the PTD-MYC fusion polypeptide. Generally, the IPTG is added to the fermenter culture at an OD600 which represents logarithmic growth phase.

In certain embodiments of the methods provided, induced protein expression is maintained for around about 2 to around about 5 hours post induction, and can be from around about 2 to around about 3 hours post-induction. Longer periods of induction may be undesirable due to degradation of the recombinant protein. The temperature of the reaction mixture during induction is preferably from about 28° C. to about 37° C., usually from about 30° C. to about 37° C. In particular embodiments, induction is at about 37° C.

The PTD-MYC fusion polypeptide is typically expressed as cytosolic inclusion bodies in microbial cells. To harvest inclusion bodies, a cell pellet is collected by centrifugation of the fermentation culture following induction, frozen at −70° C. or below, thawed and resuspended in disruption buffer. The cells are lysed by conventional methods, e.g., sonication, homogenization, etc. The lysate is then resuspended in solubilization buffer, usually in the presence of urea at a concentration effective to solubilize proteins, e.g., from around about 5M, 6M, 7M, 8M, 9M or greater. Resuspension may require mechanically breaking apart the pellet and stirring to achieve homogeneity. In some embodiments, the cell pellet is directly resuspended in urea buffer and mixed until homogenous. In some embodiments, the resuspension/solubilization buffer is 8M Urea, 50 mM Phosphate pH 7.5 and the suspension is passed through a homogenizer.

In some embodiments, the homogenized suspension is sulfonylated. For example, in some embodiments, the homogenized suspension is adjusted to include 200 mM Sodium Sulfite and 10 mM Sodium Tetrathionate. The solution is then mixed at room temperature until homogeneous. The mixed lysate is then mixed for an additional period of time to complete the sulfonylation (e.g., at 2-8° C. for ≥12 hours). The sulfonylated lysate was then centrifuged for an hour. The supernatant containing the sulfonylated PTD-MYC fusion polypeptides is then collected by centrifugation and the cell pellet discarded. The supernatant is then passed through a filter, e.g., 0.22 μm membrane filter to clarify the lysate.

The solubilized protein is then purified. Purification methods may include affinity chromatography, reversed-phase chromatography, gel exclusion chromatography, and the like. In some embodiments, affinity chromatography is used. For example, the protein is provided with an epitope tag or 6-histidine-tag for convenient purification. In the present methods, exemplary PTD-MYC fusion polypeptides comprise a 6-histidine-tag for purification using Ni affinity chromatography using Ni-resin.

In exemplary embodiments, the Ni-resin column is equilibrated in a buffer containing urea. In some embodiments, the equilibration buffer is 6M Urea, 50 mM Phosphate, 500 mM NaCl, and 10% Glycerol solution. The sulfonylated and clarified supernatant comprising the PTD-MYC fusion polypeptide is then loaded onto the Ni-resin column. The column is then washed with a wash buffer, e.g., 6M Urea, 50 mM Phosphate, 10% Glycerol, 500 mM NaCl, pH 7.5. The column was then washed with sequential wash buffers with decreasing salt concentration. For example, exemplary subsequent washed can include 6M Urea, 50 mM Phosphate, 10% Glycerol, and 2M NaCl, pH 7.5, followed another wash of 6M Urea, 50 mM Phosphate, 10% Glycerol, 50 mM NaCl, and 30 mM Imidazole, pH 7.5.

Following sequential application of the wash buffers the PTD-MYC fusion polypeptide is eluted from the column by addition of elution buffer, e.g., 6M Urea, 50 mM Phosphate, 10% Glycerol, and 50 mM NaCl, pH 7.5 with a gradient from 100 to 300 mM Imidazole, and collecting fractions. The protein containing fractions to be pooled are then filtered through a 0.22 μm membrane. Assessment of protein yield can be measured using any suitable method, e.g., spectrophotometry at UV wavelength 280.

In some embodiments, one or more additional purification methods can be employed to further purify the isolated PTD-MYC fusion polypeptides. In exemplary embodiments, the pooled fractions from the Ni-Sepharose chromatography step are further purified by anion exchange chromatography using a Q-Sepharose resin. In some embodiments, the pool is prepared for loading onto the Q-Sepharose column by diluting the samples to the conductivity of the Q Sepharose buffer (17.52+/−1 mS/cm) with the second wash buffer (e.g., 6M Urea, 50 mM Phosphate, 10% Glycerol, 2M NaCl, pH 7.5) from the Ni Sepharose chromatography step. The diluted pool is then loaded onto the Q-Sepharose column, followed by two chase steps using a chase buffer (e.g., 6M Urea, 50 mM Phosphate, 300 mM NaCl, and 10% Glycerol), with further sequential applications of the chase buffer until the UV trace reaches baseline, indicating that the protein has eluted from the column.

V. Administration of the PTD-MYC Fusion Proteins and PTD-MYC Modified Immune Cells to a Subject As provided previously, the present disclosure provides a method for treating an T cell exhaustion, or T cell impairment, in a subject in need thereof, wherein the method comprises administering an effective amount of a MYC fusion protein comprising (i) a protein transduction domain; and (ii) a MYC polypeptide sequence or one or more immune cells comprising the MYC fusion protein. In some embodiments, the methods comprise administering an effective amount of modified immune cell comprising the MYC fusion protein.

Any method known to those in the art for contacting a cell, organ or tissue with one or more PTD-MYC fusion polypeptides disclosed herein may be employed. Suitable methods include in vitro, ex vivo, or in vivo methods. In vivo methods typically include the administration of one or more PTD-MYC fusion polypeptides to a mammal, suitably a human. In vitro or ex vivo methods typically include the administration of one or more modified immune cells that have been treated with a PTD-MYC fusion polypeptides to a mammal, suitably a human. The one or more PTD-MYC fusion polypeptides or PTD-MYC modified immune cells described herein are administered to the subject in effective amounts (i.e., amounts that have desired therapeutic effect). The dose and dosage regimen will depend upon the degree of the disease state of the subject, the characteristics of the particular PTD-MYC fusion polypeptide used, e.g., its therapeutic index, and the subject's history.

The effective amount may be determined during pre-clinical trials and clinical trials by methods familiar to physicians and clinicians. An effective amount of one or more PTD-MYC fusion polypeptides or PTD-MYC modified immune cells useful in the methods disclosed herein may be administered to a mammal in need thereof by any of a number of well-known methods for administering pharmaceutical compounds and cells. The PTD-MYC fusion polypeptides or PTD-MYC modified immune cells may be administered systemically or locally.

For the administration of the PTD-MYC modified immune cell compositions, any suitable method for administration of cells to a subject may be employed. For example, suitable methods for adoptive cell therapy typically involve systemic infusion (e.g., intravenous or intraperitoneal infusion) of the modified immune cells together with a pharmaceutically acceptable carrier, diluent or excipient. In some embodiments, the PTD-MYC modified immune cells are administered locally, for example, intratumorally or at the site of infection.

In some embodiments, the one or more PTD-MYC fusion polypeptides described herein can be incorporated into pharmaceutical compositions for administration, singly or in combination, to a subject for the treatment or prevention of a microbial infection. In some embodiments, the one or more PTD-MYC fusion polypeptides or modified immune cells described herein can be incorporated into pharmaceutical compositions for administration, singly or in combination, to a subject for the treatment or prevention of immune cell exhaustion. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having one or more PTD-MYC fusion polypeptides disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of PTD-MYC fusion polypeptides described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic agent is encapsulated in a liposome while maintaining the agent's structural integrity. One skilled in the art would appreciate that there are a variety of methods to prepare liposomes. (See Lichtenberg, et al, *Methods Biochem. Anal.,* 33:337-462 (1988); Anselem, et al., *Liposome Technology,* CRC Press (1993)). Liposomal formulations can delay clearance and increase cellular uptake (See Reddy, *Ann. Pharmacother.,* 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.,* 34(7-8):915-923 (2000)). A polymer formulation for human growth hormone (hGH) has been used in clinical trials. (See Kozarich and Rich, *Chemical Biology,* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods,* 4(3): 201-9 (1994); and Gregoriadis, "Engineering Liposomes for Drug Delivery: Progress and Problems," *Trends Biotechnol.,* 13(12):527-37 (1995). Mizguchi, et al., *Cancer Lett.,* 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the one or more PTD-MYC fusion polypeptides disclosed herein sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight.

In one embodiment, one or more PTD-MYC fusion polypeptides concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of one or more PTD-MYC fusion polypeptides may be defined as a concentration of inhibitor at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

VI. Combination Therapies

In some embodiments, the PTD-MYC fusion polypeptides or the PTD-MYC modified immune cells are administered with an additional therapeutic agent. Suitable therapeutic agents for combination therapy can be selected based on the condition or disease to be treated. In some embodiments, additional therapeutic agent is administered prior to, simultaneously with, intermittently with, or following treatment with the PTD-MYC fusion polypeptides or the PTD-MYC modified immune cells. In some embodiments, the additional therapeutic agent is an immunomodulator, such as an interleukin (e.g. IL-2, IL-7, IL-12), a cytokine, a chemokine, or and immunomodulatory drug. In some embodiments, the additional therapeutic agent is an anticancer agent (e.g., chemotherapy, radiation therapy, oncolytic agent, immunotherapy, monoclonal antibodies, anti-cancer nucleic acids or proteins, anti-cancer viruses or microorganisms, and any combinations thereof), an antibacterial agent or an antiviral agent.

VII. Kits

Kits according to this embodiment can comprise a carrier means, such as a box, carton, tube, having in close confinement therein one or more containers, such as vials, tubes, ampoules, bottles, syringes, or bags. The kits can also comprise associated instructions for using the PTD-MYC fusion polypeptides and/or PTD-MYC fusion polypeptide-modified immune cells of the present technology. In some embodiments, the kit comprises an effective amount of an adoptive cell therapy, such as MYC-fusion polypeptide-modified immune cells. In some embodiments, the kit comprises one for more reagents for the detection of the administered MYC-fusion polypeptides and/or MYC-fusion polypeptide-modified immune cells.

EXAMPLES

The present technology is further illustrated by the following Examples, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology.

Example 1: Isolated Immune Cells Express Decreased Levels of Immune Checkpoint Receptors PD-1 and CTLA-4 after Treatment with TAT-MYC A whole blood sample was isolated from a donor subject and mixed with the blood anticoagulant, ethylenediaminetetraacetic acid (EDTA). After allowing the cells to incubate at least 24 hours at 37° C., 5% $CO_2$, the whole blood sample is then separated into peripheral blood mononuclear cells (PBMCs; immune cells), which include lymphocytes (e.g., T cells, B cells, NK cells) and monocytes, and waste (i.e., red blood cells, platelets, plasma, etc.) using a density-gradient solution (DGS) on a SEPAX-100 cell processing system (Biosafe America Inc., Houston, TX). The PBMCs were washed twice during the cell separation process with a 2.5% (w/v) HSA (Human Serum Albumin) solution in saline. Following the wash step, the immune cells were resuspended in the 2.5% (w/v) HSA solution at a concentration of $1 \times 10^6$ cells/ml to provide a cell suspension.

Following the cell separation process, samples of the immune cells were treated with DPBS (negative control) or TAT-MYC fusion protein (25 μg/mL for $10^6$ cells) and incubated at room temperature for 1 hour. The treated immune cells (called TBX-3400) were then re-washed on the SEPAX-100, and excess TAT-MYC was washed off of the cells with the 2.5% (w/v) HSA solution. Following the final wash step, the TBX-3400 were resuspended in in the 2.5% (w/v) HSA solution at a concentration of $1 \times 10^6$ cells/ml.

Figure 1C:
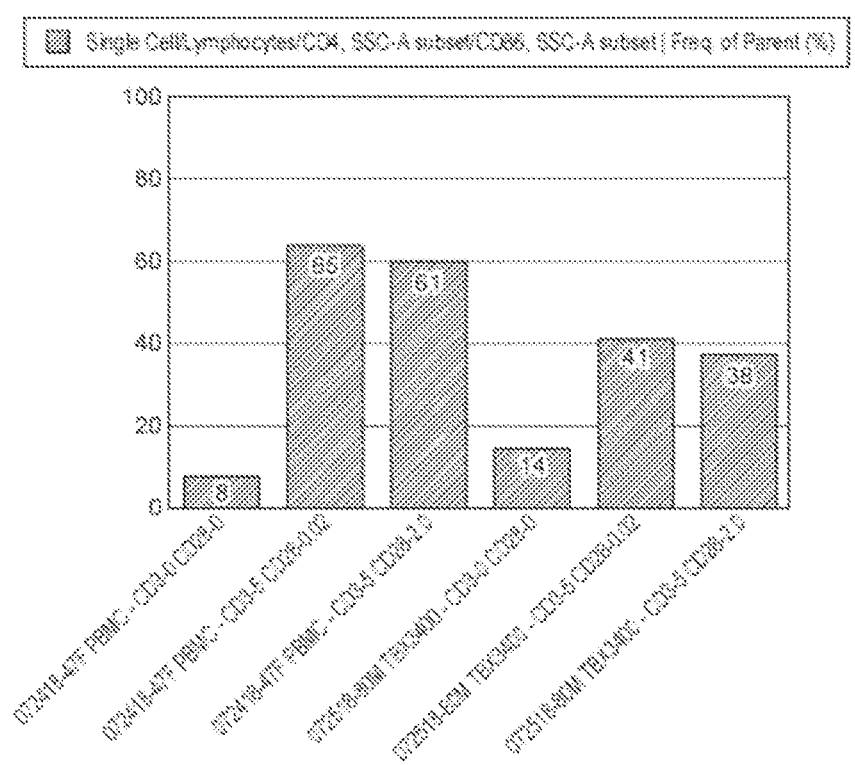
Figures 2A, 2B:
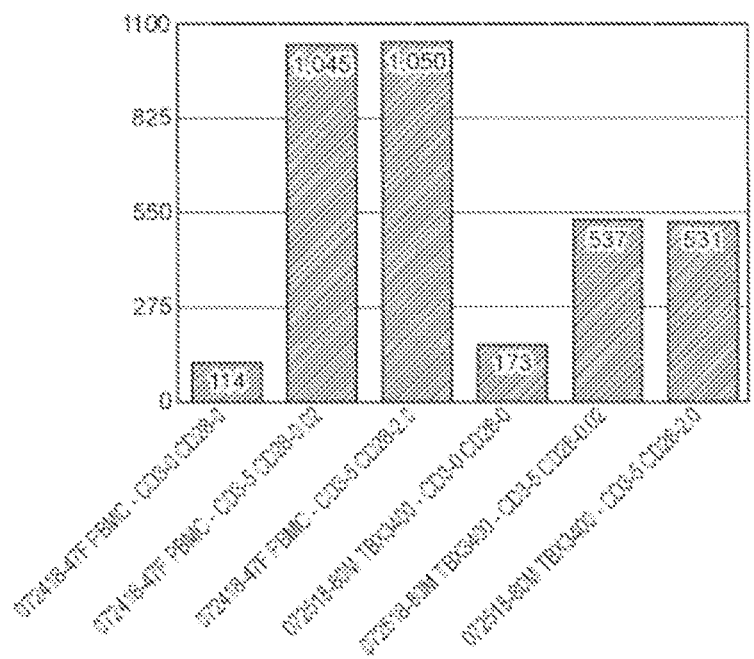
FIGS. 2A-2E illustrate the level of CD279 (PD-1) expression (FIGS. 2A-2C) and CD152 (CTLA-4) expression (FIGS. 2A and 2D-2E) in populations of immune cells isolated from donor subjects, following pre-treatment with the PTD-MYC fusion polypeptide or vehicle control, and activation under various conditions.
Figure 2C:
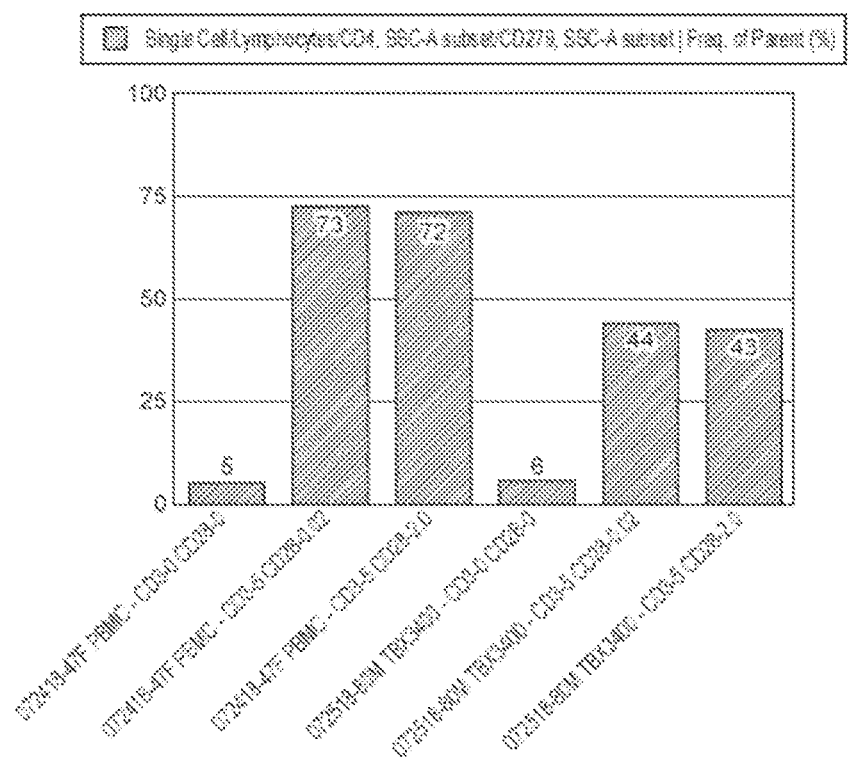
Figure 2D:
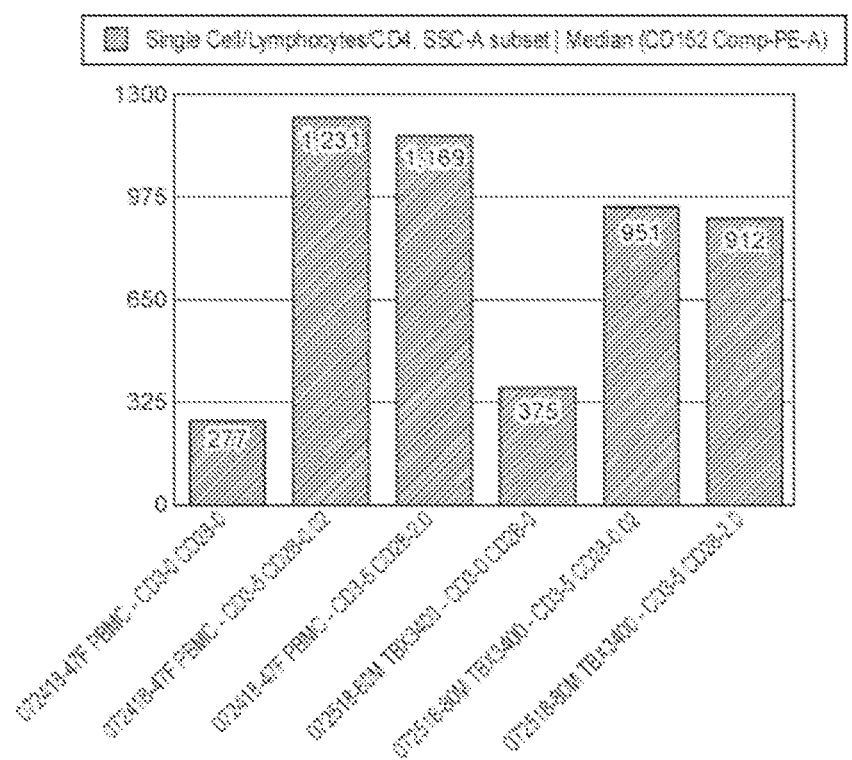
Figure 2E:
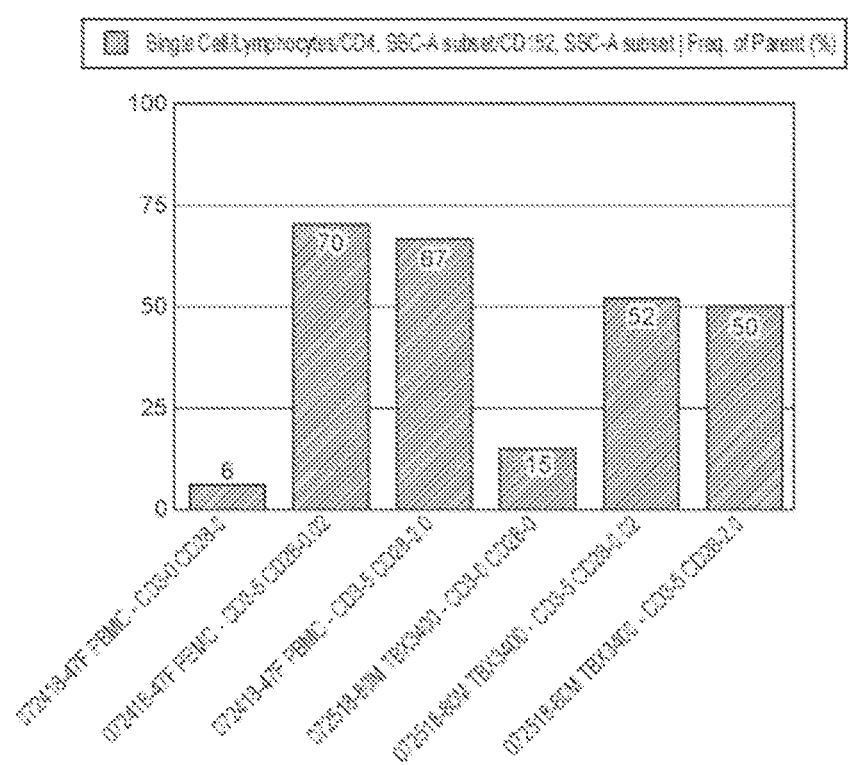
Figure 3B:
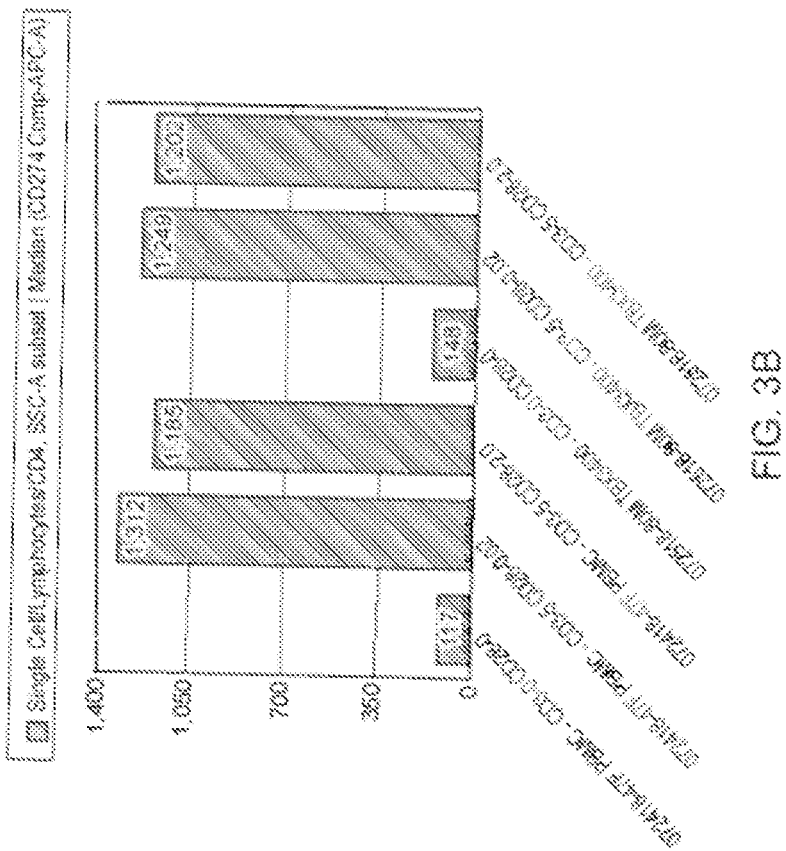
Figure 3C:
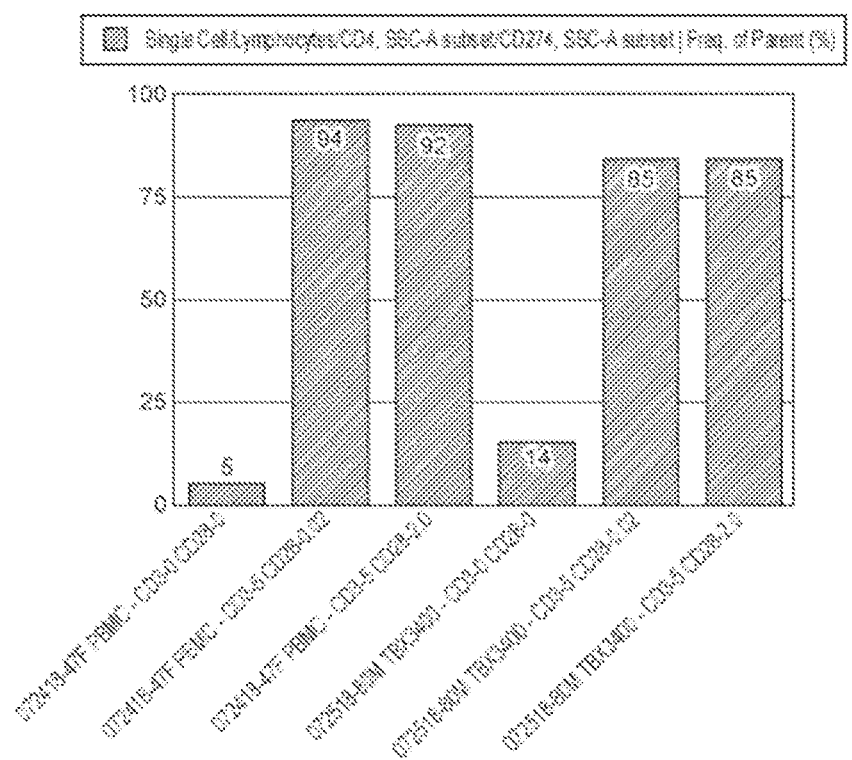
Figure 3D:
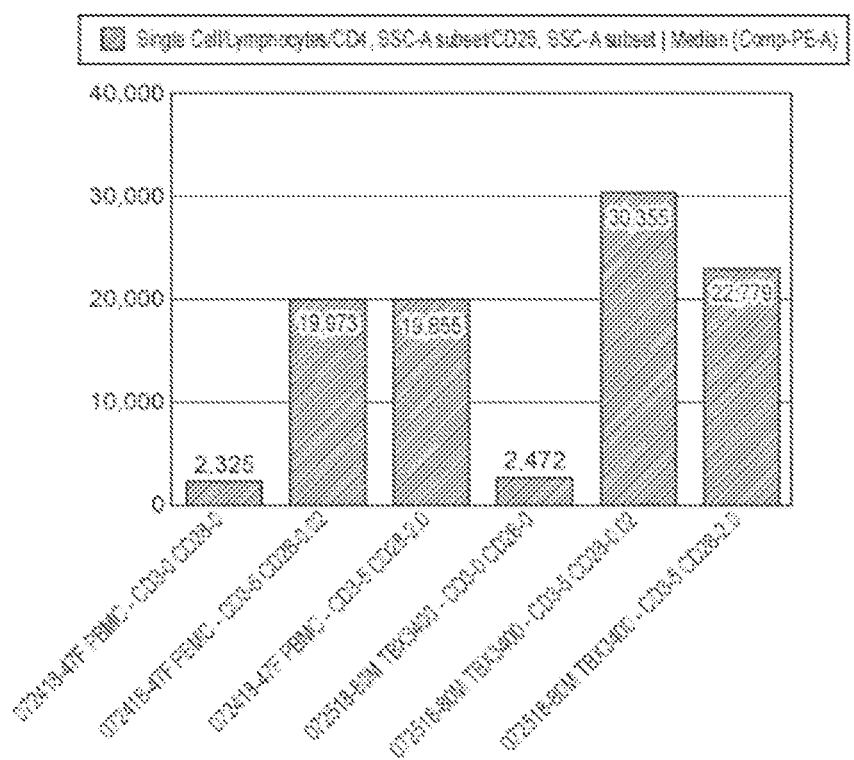
Figure 3E:
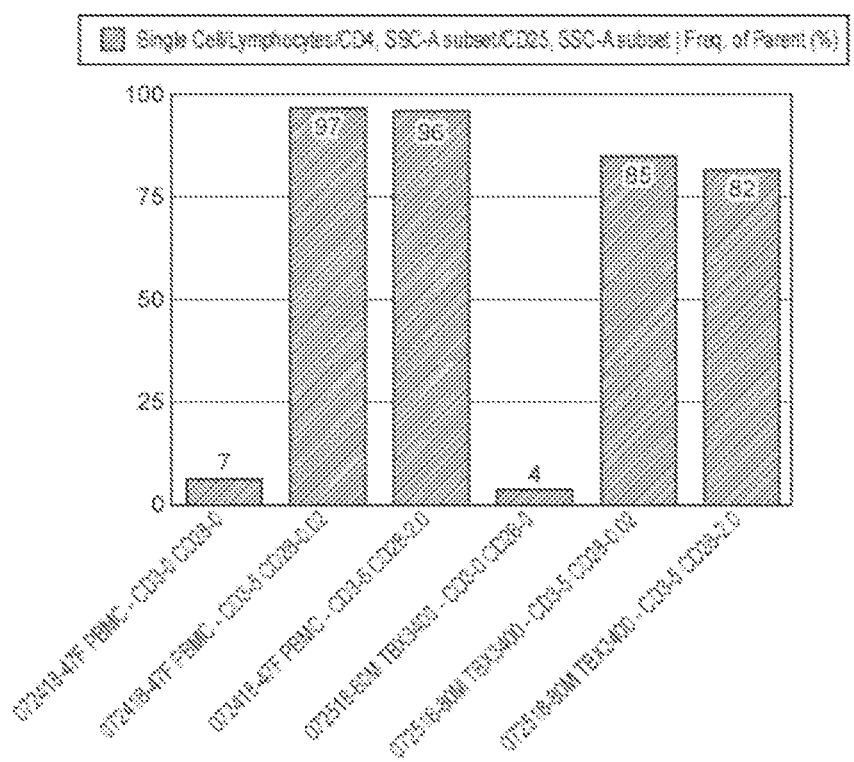

A 24-well plate was coated with a solution of an anti-CD3e antibody (500 μL, 5 μg/mL; BD Biosciences) in sterile DPBS. For control wells, only 500 μL of DPBS was added. The plates were allowed to incubated overnight at 4° C. prior to removing the solutions. Each well was then washed twice with 2 mL of sterile DPBS. Cells were then resuspended in complete RPMI medium (cRPMI) at a concentration of $2 \times 10^6$ cells/mL, and subsequently washed with 1 mL of DPBS. Next, 1.0 mL of the cell suspension was added to each well according to the plate layout. Next, a solution of an anti-CD28 antibody (100 μL, 200 μg/mL; BD Biosciences) was prepared in cRPMI and serially diluted 10-fold to make two stock solutions of the CD28 antibody in cRPMI (20 μg/mL, and 2 μg/mL). Next, 10 μL of the appropriate CD28 antibody solution or DPBS (controls or singly activated cells) was added to the designated wells. Assay plates were then incubated at 37° C., 5% $CO_2$ for 48 or 72 hours, followed by staining with the appropriate antibodies (anti-human CD25-PE, anti-human CD274-APC, anti-human CD279-APC, anti-human CD152-PE, and anti-human CD86-PE; BD Biosciences) for visualization of the magnitude of cell surface expression of immune checkpoint proteins by FACS analysis (FIGS. 1-3). FIGS. 2A-2E illustrate that the TBX-3400 demonstrates decreased expression levels of PD-1 and CTLA-4, compared to control immune cells, as determined by flow cytometry after cell activation.

Accordingly, these results demonstrate that the PTD-MYC fusion proteins disclosed herein are useful in methods for decreasing immune checkpoint proteins expressed on T cells and ameliorating and/or reversing T cell exhaustion in a subject in need thereof.

Example 2: Isolated Immune Cells Express Decreased Expression of Immune Cell Markers of Dysfunction after Treatment with TAT-MYC Peripheral blood mononuclear cells (PBMCs) are prepared as described above. Following the cell separation process, samples of the immune cells are treated with DPBS (negative control) or TAT-MYC fusion protein (25 µg/mL for $10^6$ cells) and incubated at room temperature for 1 hour. The treated immune cells (called TBX-3400) are then re-washed on the SEPAX-100, and excess TAT-MYC is washed off of the cells with the 2.5% (w/v) HSA solution. Following the final wash step, the TBX-3400 are resuspended in in the 2.5% (w/v) HSA solution at a concentration of $1\times10^6$ cells/ml.

A 24-well plate is coated with a solution of an anti-CD3e antibody (500 µL, 5 µg/mL; BD Biosciences) in sterile DPBS. For control wells, only 500 µL of DPBS was added. The plates were allowed to incubate overnight at 4° C. prior to removing the solutions. Each well is then washed twice with 2 mL of sterile DPBS. Cells are then resuspended in complete RPMI medium (cRPMI) at a concentration of $2\times10^6$ cells/mL, and subsequently washed with 1 mL of DPBS. Next, 1.0 mL of the cell suspension is added to each well according to the plate layout. Next, a solution of an anti-CD28 antibody (100 µL, 200 µg/mL; BD Biosciences) is prepared in cRPMI and serially diluted 10-fold to make two stock solutions of the CD28 antibody in cRPMI (20 µg/mL, and 2 µg/mL). Next, 10 µL of the appropriate CD28 antibody solution or DPBS (controls or singly activated cells) is added to the designated wells. Assay plates are then incubated at 37° C., 5% $CO_2$ for 48 or 72 hours, followed by staining with the antibodies to LAG3, CD160, 2B4, IL-7ra, IL-15ra, KLRG-1, TIM-3, and Eomes for visualization of the magnitude of cell surface expression of these immune cell markers of immune cell dysfunction proteins by FACS analysis. It is expected that TAT-MYC treated cells (TBX-3400) exhibit decreased expression levels of LAG3, CD160, 2B4, IL-7ra, IL-15ra, KLRG-1, TIM-3, and Eomes, compared to control immune cells, as determined by flow cytometry after cell activation.

Accordingly, these results will demonstrate that the PTD-MYC fusion proteins disclosed herein are useful in methods for decreasing cell surface expression of immune cell markers of immune cell dysfunction expressed on T cells and ameliorating and/or reversing T cell exhaustion, or T cell impairment in a subject in need thereof.

Example 3: Mice Treated with TAT-MYC Exhibit Decreased Expression of Immune Cell Markers of Dysfunction after Chronic Viral Infection In this example, mice will be treated with the PTD-MYC fusion protein of the present technology to determine whether the T cells in mice can be rescued from T cell exhaustion characterized by the increased expression of immune cell markers of T cell dysfunction after a chronic viral infection. Briefly, $2\times10^5$ plaque-forming units (PFU) of mouse hepatitis virus (MEW), cytomegalovirus (CMV), hepatitis C virus (HEPC) or lymphocytic choriomeningitis virus (LCMV), are injected i.v. into the mice to initiate chronic infection. At a pre-determined time point post-infection (e.g. 1-10 weeks post infection), the mice are separated into two groups and are treated with 50 ug/kg PTD-MYC fusion protein (e.g., daily, weekly or biweekly) or not treated (NT; control group) via s.c. tail vein injection.

Immune cells isolated from mouse hepatitis virus (MEW), cytomegalovirus (CMV), or lymphocytic choriomeningitis virus (LCMV) infected mice and control mice are then stained with the appropriate fluorochrome-labeled antibodies for visualization of the magnitude of cell surface expression of immune checkpoint proteins by FACS analysis. It is anticipated that mice which exhibit a chronic microbial infection (NT; control group) will demonstrate elevated levels of immune cell markers of dysfunction including, but not limited to, PD-1, CTLA-4, and KLRG-1. Further, it is expected that mice treated with the PTD-MYC fusion protein of the present technology will demonstrated decreased levels of immune cell markers of dysfunction.

Accordingly, it is expected that these results will demonstrate that the PTD-MYC fusion proteins disclosed herein are useful in methods for treating chronic viral infection, characterized by an increase in immune checkpoint proteins, a decrease cell surface expression of cell markers of immune cell dysfunction, and ameliorating and/or reversing immune cell exhaustion in a subject in need thereof. Further, it is expected that treatment with a MYC fusion protein results in an increase in cytokine production (e.g., IL-2, TNF), Granzyme B, and/or IFN gamma expression in the subject compared to no treatment.

Example 4: Mice Treated with TAT-MYC-Treated Immune Cells for Treatment of Chronic Viral Infection In this example, mice having a chronic viral infection are treated with immune cells isolated from the lymph node or spleen and treated with the PTD-MYC fusion protein (e.g., TBX-3400). Briefly, $2\times10^5$ plaque-forming units (PFU) of mouse hepatitis virus (MHV), cytomegalovirus (CMV), hepatitis C virus (HEPC) or lymphocytic choriomeningitis virus (LCMV), are injected i.v. into the mice to initiate chronic infection. At a pre-determined time points post-infection (e.g. 1-10 weeks post infection), the mice are separated into groups. Immune cells isolated from the lymph node or spleen that have been treated with the PTD-MYC fusion protein (e.g. TBX-3400) are administered to the mice intravenously via tail vein injection either during the initial wave of infection (to prevent chronic disease) or after the viral spike has passed and T cell function begins to decline (to treat chronic disease). The mice are assayed for expression of one or more immune checkpoint proteins and/or markers of immune cell exhaustion.

It is expected that mice treated with TBX-3400 will exhibit decreased viral titers and/or a decrease in one or more symptoms of chronic viral infection compared to control mice that are not treated with TBX-3400. Accordingly, it is expected that the treated mice will exhibit an increase in one or more immune checkpoint proteins, a decrease cell surface expression of cell markers of immune cell dysfunction, and amelioration and/or reversal of immune cell exhaustion compared to control mice that are not treated with TBX-3400. Further, it is expected that treatment with TBX-3400 results in an increase in cytokine production (e.g., IL-2, TNF), Granzyme B, and/or IFN gamma expression in the subject compared to no treatment.

Example 5: Mice Treated with TAT-MYC Exhibit Decreased Expression of Immune Cell Markers of Dysfunction after Microbial Vaccination In this example, mice will be treated with the PTD-MYC fusion protein of the present technology to determine whether the T cells in mice can be rescued from the increased expression of immune cell markers of dysfunction after microbial vaccination. Briefly, BALB\c mice are vaccinated with *M. bovis* bacille Calmette-Guérin (BCG) either via intranaseal (i.n.) vaccination or subcutaneous (s.c.) vaccination. The i.n. vaccination is carried out by applying a total of 30 mL of the BCG vaccine suspension containing $1\times10^6$ CFU drop-wise to the external nares using a micropipette and allowing the mouse to inhale the suspension into the lungs naturally. For s.c. vaccination, 50 mL of a BCG suspension is injected into the both, the right and left flanks, using a needle to deliver a total of $1\times10^6$ CFU. The vaccine diluent-administered or naïve mice serve as controls. BCG-vaccinated and control mice are separated into two groups and are treated with 50 ug/kg PTD-MYC fusion protein or not injected (NT-BCG-vaccinated; control group) via s.c. tail vein injection. At a pre-determined time point post-infection (e.g. 1-10 weeks post infection), the mice are challenged by the airway i.n. route to deliver $5\times10^4$ CFU of Mtb Erdman.

Lung or spleen cells harvested from BCG-vaccinated and control mice are then stained with the appropriate fluorochrome-labeled antibodies for visualization of cell surface expression levels of immune checkpoint proteins by FACS analysis. It is anticipated that NT-BCG-vaccinated mice will have elevated levels of immune cell markers of dysfunction including but not limited to, PD-1, CTLA-4, and KLRG-1. Further, it is expected that mice treated with the PTD-MYC fusion protein of the present technology will demonstrated decreased levels of immune cell markers of dysfunction.

Accordingly, it is anticipated that these results will demonstrate that the PTD-MYC fusion proteins disclosed herein are useful in methods for maintaining T-cell function in response to a microbial vaccine by increasing the expression of immune checkpoint proteins, decreasing cell surface expression of cell markers of immune cell dysfunction, and ameliorating and/or reversing T cell exhaustion in a subject in need thereof. Further, it is expected that treatment with a MYC fusion protein results in an increase in cytokine production (e.g., IL-2, TNF), Granzyme B, and/or IFN gamma expression in the subject compared to no treatment.

Example 6: Mice Treated with TAT-MYC-Treated Immune Cells for Treatment of Chronic Microbial Infection In this example, mice having a chronic microbial infection are treated with immune cells isolated from the lymph node or spleen and treated with the PTD-MYC fusion protein (e.g., TBX-3400). Briefly, mice are infected with a microbial pathogen (e.g., *M. bovis* bacille Calmette-Guérin (BCG)) to initiate chronic infection. At a pre-determined time points post-infection (e.g. 1-10 weeks post infection), the mice are separated into groups. Immune cells isolated from the lymph node or spleen that have been treated with the PTD-MYC fusion protein (e.g. TBX-3400) are administered to the mice intravenously via tail vein injection either during the initial wave of infection (to prevent chronic disease) or after the initial spike of infection has passed and T cell function begins to decline (to treat chronic disease). The mice are assayed for expression of one or more immune checkpoint proteins and/or markers of immune cell exhaustion.

It is expected that mice treated with TBX-3400 will exhibit decreased CFU and/or a decrease in one or more symptoms of chronic microbial infection compared to control mice that are not treated with TBX-3400. Accordingly, it is expected that the treated mice will exhibit an increase in one or more immune checkpoint proteins, a decrease cell surface expression of cell markers of immune cell dysfunction, and amelioration and/or reversal of immune cell exhaustion compared to control mice that are not treated with TBX-3400. Further, it is expected that treatment with TBX-3400 results in an increase in cytokine production (e.g., IL-2, TNF), Granzyme B, and/or IFN gamma expression in the subject compared to no treatment.

Example 7: Mice Treated with TAT-MYC Exhibit Decreased Expression of Immune Cell Markers of Dysfunction after Acute Respiratory Viral Infection In this example, mice will be treated with the PTD-MYC fusion protein of the present technology to determine whether the T cells in mice can be rescued from T cell impairment characterized by the increased expression of immune cell markers of T cell dysfunction after a chronic viral infection. Briefly, about $2\times10^5$ plaque-forming units (PFU) of a respiratory virus (e.g., influenza virus, respiratory syncytial virus (RSV), pneumonia virus, respiratory vaccinia virus, parainfluenza virus, respiratory adenoviruses, severe acute respiratory syndrome corona virus (SARS-CoV), Middle East respiratory syndrome corona virus (MFRS-CoV), or human metapneumovirus (HMPV)) are administered the mice to initiate viral infection. At a pre-determined time point post-infection (e.g. 1-10 weeks post infection), the mice are separated into two groups and are treated with 50 ug/kg PTD-MYC fusion protein (e.g., daily, weekly or biweekly) or not treated (NT; control group) via s.c. tail vein injection.

Immune cells isolated from virus-infected mice and control mice are then stained with the appropriate fluorochrome-labeled antibodies for visualization of the magnitude of cell surface expression of immune checkpoint proteins by FACS analysis. It is anticipated that mice which exhibit T-cell impairment during an acute respiratory viral infection (NT; control group) will demonstrate elevated levels of immune cell markers of dysfunction including, but not limited to, PD-1, CTLA-4, and KLRG-1. Further, it is expected that mice treated with the PTD-MYC fusion protein of the present technology will demonstrated decreased levels of immune cell markers of dysfunction.

Accordingly, it is anticipated that these results will demonstrate that the PTD-MYC fusion proteins disclosed herein are useful in methods for treating chronic viral infection, characterized by an increase in immune checkpoint proteins, a decrease cell surface expression of cell markers of immune cell dysfunction, and amelioration and/or reversal of immune cell exhaustion/impairment in a subject in need thereof. Further, it is expected that treatment with TBX-3400 results in an increase in cytokine production (e.g., IL-2, TNF), Granzyme B, and/or IFN gamma expression in the subject compared to no treatment.

Example 8: Mice Treated with TAT-MYC Exhibit Decreased Expression of Immune Cell Markers of Dysfunction after Acute Respiratory Viral Infection In this example, mice will be treated with the PTD-MYC fusion protein of the present technology to determine whether the T cells in mice can be rescued from T cell impairment characterized by the increased expression of immune cell markers of T cell dysfunction after a chronic viral infection. Briefly, about $2\times10^5$ plaque-forming units (PFU) of a respiratory virus (e.g., influenza virus, respiratory syncytial virus (RSV), pneumonia virus, respiratory vaccinia virus, parainfluenza virus, respiratory adenoviruses, severe acute respiratory syndrome corona virus (SARS-CoV), Middle East respiratory syndrome corona virus (MERS-CoV), or human metapneumovirus (HMPV)) are administered the mice to initiate infection. At a pre-determined time point post-infection (e.g. 1-10 weeks post infection), the mice are separated into groups. Immune cells isolated from the lymph node or spleen that have been treated with the PTD-MYC fusion protein (e.g. TBX-3400) are administered to the mice intravenously via tail vein injection. The mice are assayed for expression of one or more immune checkpoint proteins and/or markers of immune cell exhaustion.

It is expected that mice treated with TBX-3400 will exhibit decreased viral titers and/or a decrease in one or more symptoms of viral infection compared to control mice that are not treated with TBX-3400. Accordingly, it is expected that the treated mice will exhibit an increase in one or more immune checkpoint proteins, a decrease cell surface expression of cell markers of immune cell dysfunction, and amelioration and/or reversal of immune cell exhaustion compared to control mice that are not treated with TBX-3400. Further, it is expected that treatment with TBX-3400 results in an increase in cytokine production (e.g., IL-2, TNF), Granzyme B, and/or IFN gamma expression in the subject compared to no treatment.

Example 9: Isolated Immune Cells from Patients with Relapsed Refractory Melanoma Express Decreased Levels of Immune Checkpoint Receptors PD-1 and CTLA-4 after Treatment with TAT-MYC This Example demonstrates that Tat-MYC fusion protein treatment of peripheral blood mononuclear cells (PBMCs) isolated from patients with relapsed refractory melanoma results in decreased surface expression levels of CD279 (PD-1) and CD152 (CTLA-4) on cells treated with Tat-MYC fusion protein.

Human PBMCs are obtained from peripheral blood by Ficoll-Hypaque gradient centrifugation. The cells are washed twice in 0.9% saline supplemented with 5% human serum albumin (HSA). The cells are then incubated for 1 hour with 50 µg/mL of Tat-MYC protein in 0.9% saline and 5% HSA, at room temperature. After the incubation, the cells are washed in protein in 0.9% saline and 5% HSA three times and resuspended in that buffer for further analysis and clinical use.

Some of the cells are centrifuged and resuspended in lymphocyte growth medium. This medium consists of RPMI medium supplemented with 10% human serum, penicillin/streptomycin, L-glutamine, non-essential amino acids and 2β-mercaptoethanol. The cells are activated using plate bound anti-human CD3 antibody and soluble anti-CD28 antibodies for 4-6 days. Once the cells have been activated, they are collected, washed, and stained for flow cytometric analysis. The FACS analysis relies on the use of monoclonal antibodies directly conjugated to fluorochromes.

Figure 4A:
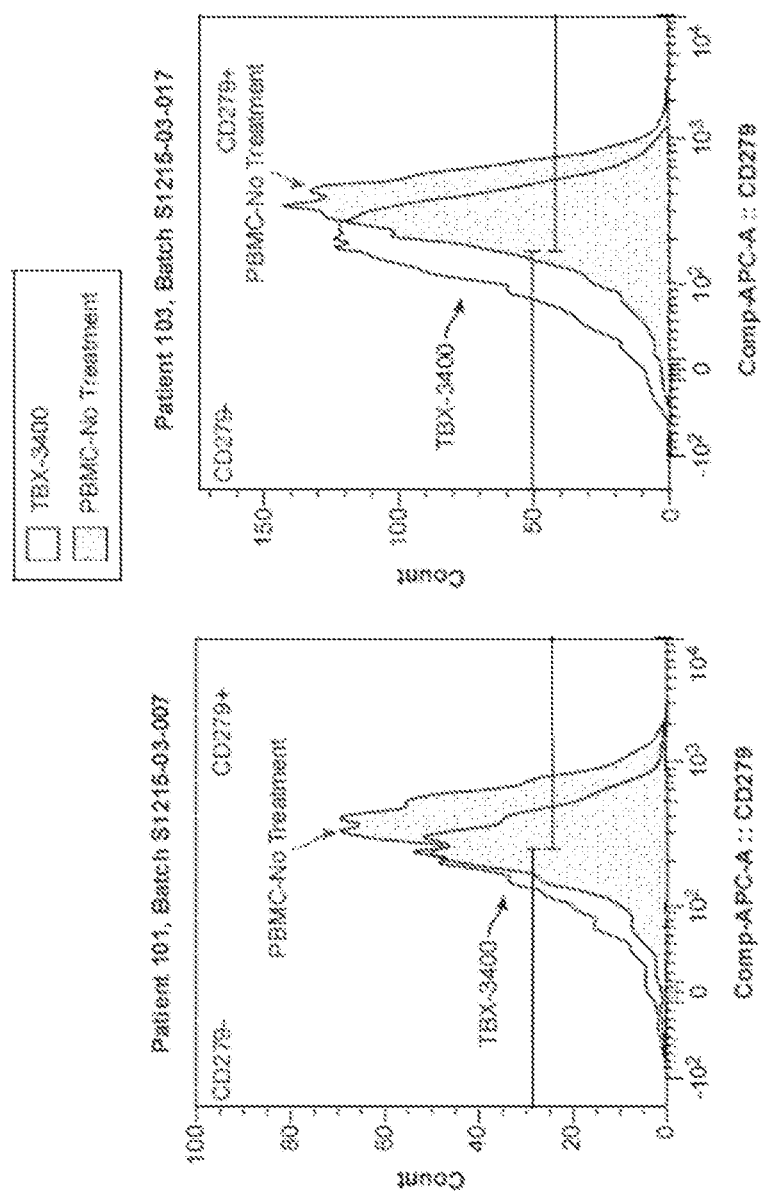
FIGS. 4A-4C illustrate the level of CD279 (PD-1) and CD152 (CTLA-4) expression in peripheral blood mononuclear cells (PBMCs) isolated from patients enrolled in a relapsed refractory melanoma clinical study.

FIG. 4A shows the results from an analysis of blood collected from two patients (101 and 103) enrolled in a clinical study for relapsed refractory melanoma. As described above, the collected blood was processed to remove red blood cells and purify PBMCs. A sample was taken of the PBMCs before and after a one-hour treatment with the Tat-MYC protein. The cells were washed and cultured with CD3 and CD28 antibodies for T cell activation. The activated T cells were labeled with fluorescent antibodies to CD279 (PD-1) and analyzed by flow cytometry. As shown in FIG. 4A, in both patients, there was a measurable downregulation of CD279 (PD-1) in the Tat-MYC treated cells (TBX-3400) compared with the untreated cells (PBMC-No treatment). Accordingly, treatment with Tat-MYC fusion protein reduces CD279 (PD-1) expression in immune cells isolated from melanoma patients.

Figure 4B:
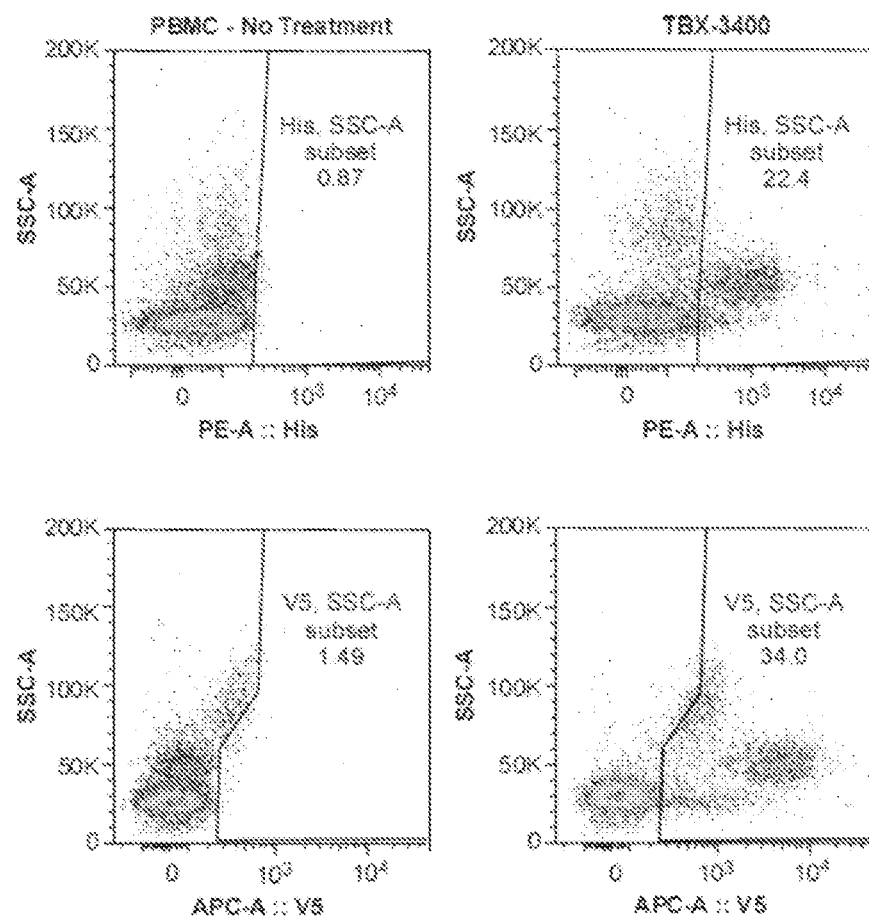

FIG. 4B shows the results of a study of PBMCs purified from a patient enrolled in the relapsed refractory melanoma trial. The patient's PBMCs were either left untreated (left panels) or treated with Tat-MYC (TBX-4000) for one hour (right panels). The diagrams show the intracellular staining results for the His or V5 tags. As shown in FIB. 4B, more than 20% of the cells treated with protein (TBX-3400) have internalized the protein.

Figure 4C:
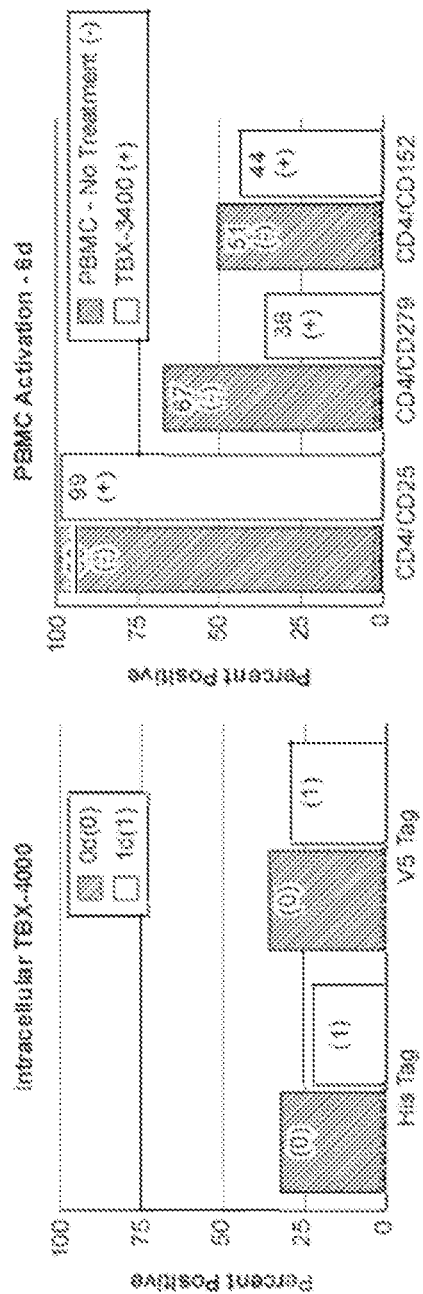

FIG. 4C shows the results of a study on PBMCs treated with Tat-MYC (TBX-4000) for one hour in a closed system. Samples were analyzed by flow cytometry for intracellular levels of the protein by using fluorescent antibodies that bind to two different tags encoded in Tat-MYC (His Tag and V5 Tag). As shown in FIG. 4C (left panel), over 25% of the cells stained positive for the protein on day zero (0 d) and similar levels were detected the following day (1 d). Tat-MYC treated cells (TBX-3400) and untreated cells (PBMC-No Treatment) isolated from the patient were activated with antibodies to CD3 and CD28, and the expression levels of the T cell activation marker, CD25, and the checkpoint markers, CD279 (PD-1) and CD152 (CTLA-4), were analyzed by flow cytometry. As shown in FIG. 4C (right panel), Tat-MYC treated cells had similar levels of CD25 yet lower levels of both checkpoint markers when compared with untreated cells.

Accordingly, these results demonstrate that the PTD-MYC fusion proteins disclosed herein are useful in methods for decreasing immune checkpoint proteins expressed on T cells and ameliorating and/or reversing T cell exhaustion and are useful in methods for treating T cell exhaustion in a subject in need thereof The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization;* Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.* Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics,* Second Edition. (John Wiley and Sons, Inc., NY, 1999)).

What is claimed is:

1. A method for treating T cell exhaustion in a subject having a microbial infection, wherein the subject does not have melanoma, comprising administering an effective amount of one or more modified immune cells to the subject, wherein the immune cells are lymphocytes, natural killer cells, myeloid cells, or combinations thereof, and wherein the one or more modified immune cells comprises a MYC fusion protein comprising (i) a protein transduction domain; and (ii) a MYC polypeptide, wherein the MYC fusion protein comprises the sequence of SEQ ID: NO: 1.

2. The method of claim 1, wherein the subject is identified as having altered expression of at least one immune cell marker of T cell exhaustion compared to expression of the at least one immune cell marker in a healthy control.

3. The method of claim 2, wherein the immune cell marker is an immune checkpoint protein.

4. The method of claim 1, wherein the one or more modified immune cells are derived from immune cells isolated from the subject.

5. The method of claim 1, wherein the immune cells isolated from the subject are obtained from the peripheral blood, the lymph node, spleen, or tumor of the subject.

6. The method of claim 1, wherein the one or more modified immune cells are prepared by contacting the immune cells in vitro with the MYC fusion protein.

7. The method of claim 2, wherein the altered expression comprises an increase in the cell surface expression of one or more immune cell receptors.

8. The method of claim 1 wherein the microbial infection is a chronic microbial infection.

9. The method of claim 1, wherein the microbial infection is caused by a pathogen selected from the group consisting of *Mycobacterium tuberculosis, Mycobacterium leprae, Mycobacterium bovis, Helicobacter pylori, Staphylococcus aureus, Salmonella Typhi, Treponema pallidum, Escherichia coli, Hemophilus influenza, Pseudomonas aeruginosa, Plasmodium falciparum, Plasmodium vivax, Plasmodium ovale, Plasmodium malariae,* Human Immunodeficiency Virus (HIV), Herpesviruses, Herpes Simplex Virus (HSV), Hepatitis B Virus (HBV), Hepatitis C Virus (HCV), Measles Virus, Papovaviruses, Varicella-Zoster Virus, T-Cell Leukemia Viruses, Adenoviruses, Parvoviruses, Epstein-Barr Virus, Enterovirus, Mouse Hepatitis Virus (MHV), Cytomegalovirus (CMV), Papillomaviruses, Lymphocytic Choriomeningitis Virus (LCMV) influenza virus, respiratory syncytial virus (RSV), pneumonia virus, respiratory vaccinia virus, parainfluenza virus, respiratory adenoviruses, severe acute respiratory syndrome corona virus (SARS-Co V), Middle East respiratory syndrome corona virus (MERS-COV), and human metapneumovirus (HMPV).

* * * * *

SEQUENCE LISTING

```
<160> NUMBER OF SEQ ID NOS: 13

<210> SEQ ID NO 1
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Arg Lys Lys Arg Arg Gln Arg Arg Pro Leu Asn Val Ser Phe
1               5                   10                  15

Thr Asn Arg Asn Tyr Asp Leu Asp Tyr Asp Ser Val Gln Pro Tyr Phe
                20                  25                  30

Tyr Cys Asp Glu Glu Glu Asn Phe Tyr Gln Gln Gln Gln Ser Glu
            35                  40                  45

Leu Gln Pro Pro Ala Pro Ser Glu Asp Ile Trp Lys Lys Phe Glu Leu
    50                  55                  60

Leu Pro Thr Pro Pro Leu Ser Pro Ser Arg Arg Ser Gly Leu Cys Ser
65                  70                  75                  80

Pro Ser Tyr Val Ala Val Thr Pro Phe Ser Leu Arg Gly Asp Asn Asp
                85                  90                  95

Gly Gly Gly Gly Ser Phe Ser Thr Ala Asp Gln Leu Glu Met Val Thr
            100                 105                 110

Glu Leu Leu Gly Gly Asp Met Val Asn Gln Ser Phe Ile Cys Asp Pro
        115                 120                 125

Asp Asp Glu Thr Phe Ile Lys Asn Ile Ile Ile Gln Asp Cys Met Trp
    130                 135                 140
```

Ser Gly Phe Ser Ala Ala Ala Lys Leu Val Ser Glu Lys Leu Ala Ser
145                 150                 155                 160

Tyr Gln Ala Ala Arg Lys Asp Ser Gly Ser Pro Asn Pro Ala Arg Gly
                165                 170                 175

His Ser Val Cys Ser Thr Ser Ser Leu Tyr Leu Gln Asp Leu Ser Ala
            180                 185                 190

Ala Ala Ser Glu Cys Ile Asp Pro Ser Val Val Phe Pro Tyr Pro Leu
        195                 200                 205

Asn Asp Ser Ser Ser Pro Lys Ser Cys Ala Ser Gln Asp Ser Ser Ala
    210                 215                 220

Phe Ser Pro Ser Ser Asp Ser Leu Leu Ser Ser Thr Glu Ser Ser Pro
225                 230                 235                 240

Gln Gly Ser Pro Glu Pro Leu Val Leu His Glu Glu Thr Pro Pro Thr
                245                 250                 255

Thr Ser Ser Asp Ser Glu Glu Glu Gln Glu Asp Glu Glu Glu Ile Asp
            260                 265                 270

Val Val Ser Val Glu Lys Arg Gln Ala Pro Gly Lys Arg Ser Glu Ser
        275                 280                 285

Gly Ser Pro Ser Ala Gly Gly His Ser Lys Pro Pro His Ser Pro Leu
    290                 295                 300

Val Leu Lys Arg Cys His Val Ser Thr His Gln His Asn Tyr Ala Ala
305                 310                 315                 320

Pro Pro Ser Thr Arg Lys Asp Tyr Pro Ala Ala Lys Arg Val Lys Leu
                325                 330                 335

Asp Ser Val Arg Val Leu Arg Gln Ile Ser Asn Asn Arg Lys Cys Thr
            340                 345                 350

Ser Pro Arg Ser Ser Asp Thr Glu Glu Asn Val Lys Arg Arg Thr His
        355                 360                 365

Asn Val Leu Glu Arg Gln Arg Arg Asn Glu Leu Lys Arg Ser Phe Phe
    370                 375                 380

Ala Leu Arg Asp Gln Ile Pro Glu Leu Glu Asn Asn Glu Lys Ala Pro
385                 390                 395                 400

Lys Val Val Ile Leu Lys Lys Ala Thr Ala Tyr Ile Leu Ser Val Gln
                405                 410                 415

Ala Glu Glu Gln Lys Leu Ile Ser Glu Glu Asp Leu Leu Arg Lys Arg
            420                 425                 430

Arg Glu Gln Leu Lys His Lys Leu Glu Gln Leu Arg Lys Gly Glu Leu
        435                 440                 445

Asn Ser Lys Leu Glu Gly Lys Pro Ile Pro Asn Pro Leu Leu Gly Leu
    450                 455                 460

Asp Ser Thr Arg Thr Gly His His His His His His
465                 470                 475

<210> SEQ ID NO 2
<211> LENGTH: 439
<212> TYPE: PRT
<213> ORGANISM: Homo sapiens

<400> SEQUENCE: 2

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp

```
                35                  40                  45
Ile Trp Lys Lys Phe Glu Leu Leu Pro Thr Pro Pro Leu Ser Pro Ser
 50                  55                  60

Arg Arg Ser Gly Leu Cys Ser Pro Ser Tyr Val Ala Val Thr Pro Phe
 65                  70                  75                  80

Ser Leu Arg Gly Asp Asn Asp Gly Gly Gly Ser Phe Ser Thr Ala
                 85                  90                  95

Asp Gln Leu Glu Met Val Thr Glu Leu Leu Gly Gly Asp Met Val Asn
                100                 105                 110

Gln Ser Phe Ile Cys Asp Pro Asp Glu Thr Phe Ile Lys Asn Ile
                115                 120                 125

Ile Ile Gln Asp Cys Met Trp Ser Gly Phe Ser Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ser Glu Cys Ile Asp Pro Ser
                180                 185                 190

Val Val Phe Pro Tyr Pro Leu Asn Asp Ser Ser Ser Pro Lys Ser Cys
    195                 200                 205

Ala Ser Gln Asp Ser Ser Ala Phe Ser Pro Ser Ser Asp Ser Leu Leu
210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
                260                 265                 270

Pro Gly Lys Arg Ser Glu Ser Gly Ser Pro Ser Ala Gly Gly His Ser
                275                 280                 285

Lys Pro Pro His Ser Pro Leu Val Leu Lys Arg Cys His Val Ser Thr
290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
                340                 345                 350

Asn Val Lys Arg Arg Thr His Asn Val Leu Glu Arg Gln Arg Arg Asn
                355                 360                 365

Glu Leu Lys Arg Ser Phe Phe Ala Leu Arg Asp Gln Ile Pro Glu Leu
                370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Glu Gln Leu Lys His Lys Leu Glu
                420                 425                 430

Gln Leu Arg Asn Ser Cys Ala
                435

<210> SEQ ID NO 3
```

```
<211> LENGTH: 450
<212> TYPE: PRT
<213> ORGANISM: Homo sapiens

<400> SEQUENCE: 3

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
```

```
                385                 390                 395                 400
Asn Asn Glu Lys Ala Pro Lys Val Val Ile Leu Lys Lys Ala Thr Ala
                    405                 410                 415
Tyr Ile Leu Ser Val Gln Ala Glu Glu Gln Lys Leu Ile Ser Glu Glu
                    420                 425                 430
Asp Leu Leu Arg Lys Arg Glu Gln Leu Lys His Lys Leu Glu Gln
                    435                 440                 445
Leu Arg
    450

<210> SEQ ID NO 4
<211> LENGTH: 434
<212> TYPE: PRT
<213> ORGANISM: Homo sapiens

<400> SEQUENCE: 4

Pro Leu Asn Val Ser Phe Thr Asn Arg Asn Tyr Asp Leu Asp Tyr Asp
1               5                   10                  15
Ser Val Gln Pro Tyr Phe Tyr Cys Asp Glu Glu Asn Phe Tyr Gln
                20                  25                  30
Gln Gln Gln Gln Ser Glu Leu Gln Pro Pro Ala Pro Ser Glu Asp Ile
                35                  40                  45
Trp Lys Lys Phe Glu Leu Leu Pro Thr Pro Pro Leu Ser Pro Ser Arg
    50                  55                  60
Arg Ser Gly Leu Cys Ser Pro Ser Tyr Val Ala Val Thr Pro Phe Ser
65                  70                  75                  80
Leu Arg Gly Asp Asn Asp Gly Gly Gly Gly Ser Phe Ser Thr Ala Asp
                    85                  90                  95
Gln Leu Glu Met Val Thr Glu Leu Leu Gly Gly Asp Met Val Asn Gln
                100                 105                 110
Ser Phe Ile Cys Asp Pro Asp Asp Glu Thr Phe Ile Lys Asn Ile Ile
                115                 120                 125
Ile Gln Asp Cys Met Trp Ser Gly Phe Ser Ala Ala Ala Lys Leu Val
    130                 135                 140
Ser Glu Lys Leu Ala Ser Tyr Gln Ala Ala Arg Lys Asp Ser Gly Ser
145                 150                 155                 160
Pro Asn Pro Ala Arg Gly His Ser Val Cys Ser Thr Ser Ser Leu Tyr
                165                 170                 175
Leu Gln Asp Leu Ser Ala Ala Ala Ser Glu Cys Ile Asp Pro Ser Val
                180                 185                 190
Val Phe Pro Tyr Pro Leu Asn Asp Ser Ser Ser Pro Lys Ser Cys Ala
                195                 200                 205
Ser Gln Asp Ser Ser Ala Phe Ser Pro Ser Ser Asp Ser Leu Leu Ser
    210                 215                 220
Ser Thr Glu Ser Ser Pro Gln Gly Ser Pro Glu Pro Leu Val Leu His
225                 230                 235                 240
Glu Glu Thr Pro Pro Thr Thr Ser Ser Asp Ser Glu Glu Gln Glu
                245                 250                 255
Asp Glu Glu Glu Ile Asp Val Val Ser Val Glu Lys Arg Gln Ala Pro
                260                 265                 270
Gly Lys Arg Ser Glu Ser Gly Ser Pro Ser Ala Gly Gly His Ser Lys
                275                 280                 285
Pro Pro His Ser Pro Leu Val Leu Lys Arg Cys His Val Ser Thr His
    290                 295                 300
```

```
Gln His Asn Tyr Ala Ala Pro Pro Ser Thr Arg Lys Asp Tyr Pro Ala
305                 310                 315                 320

Ala Lys Arg Val Lys Leu Asp Ser Val Arg Val Leu Arg Gln Ile Ser
            325                 330                 335

Asn Asn Arg Lys Cys Thr Ser Pro Arg Ser Ser Asp Thr Glu Glu Asn
            340                 345                 350

Val Lys Arg Arg Thr His Asn Val Leu Glu Arg Gln Arg Arg Asn Glu
        355                 360                 365

Leu Lys Arg Ser Phe Phe Ala Leu Arg Asp Gln Ile Pro Glu Leu Glu
    370                 375                 380

Asn Asn Glu Lys Ala Pro Lys Val Val Ile Leu Lys Lys Ala Thr Ala
385                 390                 395                 400

Tyr Ile Leu Ser Val Gln Ala Glu Glu Gln Lys Leu Ile Ser Glu Glu
                405                 410                 415

Asp Leu Leu Arg Lys Arg Arg Glu Gln Leu Lys His Lys Leu Glu Gln
                420                 425                 430

Leu Arg
```

<210> SEQ ID NO 5
<211> LENGTH: 67
<212> TYPE: PRT
<213> ORGANISM: Homo sapiens

<400> SEQUENCE: 5

```
Glu Leu Lys Arg Ser Phe Phe Ala Leu Arg Asp Gln Ile Pro Glu Leu
1               5                   10                  15

Glu Asn Asn Glu Lys Ala Pro Lys Val Val Ile Leu Lys Lys Ala Thr
            20                  25                  30

Ala Tyr Ile Leu Ser Val Gln Ala Glu Glu Gln Lys Leu Ile Ser Glu
        35                  40                  45

Glu Asp Leu Leu Arg Lys Arg Arg Glu Gln Leu Lys His Lys Leu Glu
    50                  55                  60

Gln Leu Arg
65
```

<210> SEQ ID NO 6
<211> LENGTH: 14
<212> TYPE: PRT
<213> ORGANISM: Unknown
<220> FEATURE:
<223> OTHER INFORMATION: Description of Unknown:
      E-box DNA binding domain

<400> SEQUENCE: 6

```
Lys Arg Arg Thr His Asn Val Leu Glu Arg Gln Arg Arg Asn
1               5                   10
```

<210> SEQ ID NO 7
<211> LENGTH: 10
<212> TYPE: PRT
<213> ORGANISM: Human immunodeficiency virus 1

<400> SEQUENCE: 7

```
Met Arg Lys Lys Arg Arg Gln Arg Arg Arg
1               5                   10
```

<210> SEQ ID NO 8
<211> LENGTH: 6
<212> TYPE: PRT
<213> ORGANISM: Artificial Sequence -continued

```
<220> FEATURE:
<223> OTHER INFORMATION: Description of Artificial Sequence: Synthetic
      6xHis tag

<400> SEQUENCE: 8

His His His His His His
1               5

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Lys Pro Ile Pro Asn Pro Leu Leu Gly Leu Asp Ser Thr
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Pro Asn Pro Leu Leu Gly Leu Asp
1               5

<210> SEQ ID NO 11
<211> LENGTH: 454
<212> TYPE: PRT
<213> ORGANISM: Homo sapiens

<400> SEQUENCE: 11

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
        130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
```

```
                    180                 185                 190
Leu Gln Asp Leu Ser Ala Ala Ser Glu Cys Ile Asp Pro Ser Val
            195                 200                 205

Val Phe Pro Tyr Pro Leu Asn Asp Ser Ser Pro Lys Ser Cys Ala
        210                 215                 220

Ser Gln Asp Ser Ser Ala Phe Ser Pro Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Gly Glu Leu Asn Ser Lys Leu Glu
1               5

<210> SEQ ID NO 13
<211> LENGTH: 9
<212> TYPE: PRT
<213> ORGANISM: Human immunodeficiency virus 1

<400> SEQUENCE: 13

Arg Lys Lys Arg Arg Gln Arg Arg Arg
1               5
```